(12) United States Patent
Dobak et al.

(10) Patent No.: US 8,404,750 B2
(45) Date of Patent: *Mar. 26, 2013

(54) METHODS FOR ADMINISTRATION AND FORMULATIONS FOR THE TREATMENT OF REGIONAL ADIPOSE TISSUE

(75) Inventors: John Daniel Dobak, La Jolla, CA (US); Kenneth Walter Locke, Carlsbad, CA (US)

(73) Assignee: Lithera, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/284,741

(22) Filed: Oct. 28, 2011

(65) Prior Publication Data

US 2012/0046257 A1 Feb. 23, 2012

Related U.S. Application Data

(63) Continuation of application No. 12/788,190, filed on May 26, 2010.

(60) Provisional application No. 61/181,627, filed on May 27, 2009, provisional application No. 61/251,624, filed on Oct. 14, 2009, provisional application No. 61/289,972, filed on Dec. 23, 2009.

(51) Int. Cl.
*A61K 31/137* (2006.01)
*A61K 31/167* (2006.01)
*A61K 31/56* (2006.01)

(52) U.S. Cl. .................. 514/651; 514/629; 514/171

(58) Field of Classification Search .................. None
See application file for complete search history.

(56) References Cited

U.S. PATENT DOCUMENTS

| | | | |
|---|---|---|---|
| 4,525,359 A | 6/1985 | Greenway | |
| 4,800,079 A | 1/1989 | Boyer | |
| 4,826,879 A | 5/1989 | Yamamoto et al. | |
| 5,126,147 A | 6/1992 | Silvestri et al. | |
| 5,314,916 A | 5/1994 | York et al. | |
| 5,496,803 A | 3/1996 | Meier et al. | |
| 5,709,884 A | 1/1998 | Trofast et al. | |
| 5,972,919 A | 10/1999 | Carling | |
| 6,030,604 A | 2/2000 | Trofast | |
| 6,066,675 A | 5/2000 | Wen et al. | |
| 6,110,974 A | 8/2000 | Aberg et al. | |
| 6,316,443 B1 | 11/2001 | Baldwin et al. | |
| 6,537,983 B1 | 3/2003 | Biggadike et al. | |
| 6,643,212 B1 | 11/2003 | Jones, Jr. et al. | |
| 6,656,508 B2 | 12/2003 | Goldenberg et al. | |
| 6,869,942 B2 | 3/2005 | Trofast et al. | |
| 7,172,752 B2 | 2/2007 | Watanabe et al. | |
| 7,253,156 B2 | 8/2007 | Currie et al. | |
| 7,267,813 B2 | 9/2007 | Watanabe et al. | |
| 7,348,362 B2 | 3/2008 | Banerjee et al. | |
| 7,354,913 B2 | 4/2008 | Trofast et al. | |
| 7,638,508 B2 | 12/2009 | Biggadike et al. | |
| 7,662,815 B2 | 2/2010 | McKinnell et al. | |
| 7,723,392 B2 | 5/2010 | Aberg et al. | |
| 7,829,544 B2 | 11/2010 | Sawa | |
| 2002/0032149 A1 | 3/2002 | Kensey | |
| 2002/0042404 A1 | 4/2002 | Bauer | |
| 2003/0022856 A1 | 1/2003 | Richardson et al. | |
| 2003/0095925 A1 | 5/2003 | Dugger | |
| 2003/0161207 A1 | 8/2003 | Jones, Jr. et al. | |
| 2003/0236238 A1 | 12/2003 | Trofast et al. | |
| 2004/0037875 A1 | 2/2004 | Metselaar et al. | |
| 2004/0065325 A1 | 4/2004 | Trofast et al. | |
| 2004/0171597 A1 | 9/2004 | Biggadike et al. | |
| 2004/0208833 A1 | 10/2004 | Hovey et al. | |
| 2004/0208910 A1 | 10/2004 | Ashton et al. | |
| 2004/0235922 A1 | 11/2004 | Baile et al. | |
| 2004/0247628 A1 | 12/2004 | Lintz et al. | |
| 2005/0048127 A1 | 3/2005 | Brown et al. | |
| 2005/0069591 A1 | 3/2005 | Bernstein et al. | |
| 2005/0113456 A1 | 5/2005 | Aberg | |
| 2005/0141293 A1 | 6/2005 | Ha | |
| 2005/0207989 A1 | 9/2005 | Trofast et al. | |
| 2005/0222108 A1 | 10/2005 | Bhatarah et al. | |
| 2005/0244339 A1 | 11/2005 | Jauernig et al. | |
| 2005/0267080 A1 | 12/2005 | Kolodney et al. | |
| 2006/0051299 A1 | 3/2006 | Chaudry | |
| 2006/0188579 A1 | 8/2006 | Rogueda | |
| 2006/0189587 A9 | 8/2006 | Bauer | |
| 2007/0014843 A1 | 1/2007 | Dobak | |
| 2007/0178051 A1 | 8/2007 | Pruitt | |
| 2007/0178166 A1 | 8/2007 | Bernstein et al. | |
| 2008/0157409 A1 | 7/2008 | Reens | |

(Continued)

FOREIGN PATENT DOCUMENTS

| | | |
|---|---|---|
| CA | 2615173 | 1/2007 |
| CA | 2666564 | 6/2008 |

(Continued)

OTHER PUBLICATIONS

Ryall et al., Journal of Applied Physiology, 2008, vol. 105, pp. 165-172.*

Arner et al., "Human fat cell lipolysis: biochemistry, regulation and clinical role," Best Practice & Research Clinical Endocrinology & Metabolism 19:471-482 (2005).

Arner, et al. "Adrenergic Regulation of Lipolysis In Situ at Rest and during Exercise," J. Clin. Invest., vol. 85, pp. 893-898 (1990).

(Continued)

*Primary Examiner* — Savitha Rao
*Assistant Examiner* — Gregg Polansky
(74) *Attorney, Agent, or Firm* — Wilson, Sonsini, Goodrich & Rosati

(57) ABSTRACT

Provided herein are pharmaceutical formulations, methods, and systems for treating regional fat deposits and fat-related conditions and indications. Methods comprise administering a pharmaceutical formulation consisting essentially of a long-acting beta-2 adrenergic receptor agonist, for example, salmeterol, suitable for subcutaneous administration. Methods further comprise administering a pharmaceutical formulation that is suitable for subcutaneous injection comprising: (a) a lipophilic long-acting selective beta-2 adrenergic receptor agonist and/or glucocorticosteroid, or a salt, optical isomer, racemate, solvate, or polymorph thereof; and (b) at least one subcutaneously acceptable inactive ingredient.

22 Claims, 8 Drawing Sheets

U.S. PATENT DOCUMENTS

| | | |
|---|---|---|
| 2008/0249017 A1 | 10/2008 | Loughrey et al. |
| 2008/0300229 A1 | 12/2008 | Wilcox et al. |
| 2009/0123550 A1 | 5/2009 | Phillips |
| 2010/0093693 A1 | 4/2010 | Shen et al. |
| 2010/0119609 A1 | 5/2010 | Dobak |
| 2010/0137267 A1 | 6/2010 | Dobak |
| 2011/0105446 A1 | 5/2011 | Dobak |
| 2011/0130373 A1 | 6/2011 | Dobak et al. |
| 2011/0166202 A1 | 7/2011 | Banerjee |
| 2011/0224176 A1 | 9/2011 | Dobak et al. |
| 2012/0015918 A1 | 1/2012 | Dobak |
| 2012/0046256 A1 | 2/2012 | Dobak |
| 2012/0178819 A1 | 7/2012 | Dobak |

FOREIGN PATENT DOCUMENTS

| | | |
|---|---|---|
| CN | 1640390 | 7/2005 |
| EP | 0120165 | 10/1984 |
| EP | 1153614 | 11/2001 |
| EP | 1867334 | 12/2007 |
| GB | 1471326 | 4/1977 |
| GB | 2443287 A | 4/2008 |
| GB | 2453188 A | 4/2009 |
| GB | 2470818 | 12/2010 |
| GB | 2477030 | 7/2011 |
| JP | 61-31043 | 2/1986 |
| JP | 11106334 | 4/1999 |
| JP | 2004-513340 | 4/2004 |
| KR | 2009-0112590 | 10/2009 |
| WO | WO-98-41232 | 9/1998 |
| WO | WO-98-48810 | 11/1998 |
| WO | WO-01-19373 | 3/2001 |
| WO | WO-01-28535 | 4/2001 |
| WO | WO-03-033000 | 4/2003 |
| WO | WO-2004-028545 | 4/2004 |
| WO | WO-2004-091574 | 10/2004 |
| WO | WO-2004-103057 | 12/2004 |
| WO | WO-2004-103379 | 12/2004 |
| WO | WO-2005-007145 | 1/2005 |
| WO | WO-2005-072745 | 8/2005 |
| WO | WO-2006-122165 | 11/2006 |
| WO | WO-2007-011743 | 1/2007 |
| WO | WO-2007-117661 | 10/2007 |
| WO | WO-2008-048770 | 4/2008 |
| WO | WO-2008-066775 | 6/2008 |
| WO | WO-2008-067060 | 6/2008 |
| WO | WO-2008-157409 | 12/2008 |
| WO | WO-2009-000473 | 12/2008 |
| WO | WO-2010-138770 | 12/2010 |
| WO | WO-2011-088413 | 7/2011 |

OTHER PUBLICATIONS

Arner, et al., "In Vivo Interactions between Beta-1 and Beta-2 Adrenoceptors Regulate Catecholamine Tachyphylaxia in Human Adipose Tissue," Journ. Pharm. Exper. Therap., vol. 259, No. 1, pp. 317-322 (1991).

Arner, et al., "Adrenergic Receptor Function in Fat Cells1-3," Am. J. Clin. Nutr. 55:228S-36S (1992).

Barbe, et al., "In situ assessment of the role of the $\beta$1-, $\beta$2- and $\beta$3 adrenoceptors in the control of lipolysis and nutritive blood flow in human subcutaneous adipose tissue," British Journ. Pharma. (1996) 11 (7 pgs.).

Barbe, et al., "In Vivo Increase in $\beta$-Adrenergic Lipolytic Response in Subcutaneous Adipose Tissue of Obese Subject Submitted to a Hypocaloric Diet," Journ. Clin. Endocrin. and Metab., vol. 82, No. 1, pp. 63-69 (1997).

Barnes, "Scientific rationale for inhaled combination therapy with long-acting $\beta$2-agonists and corticosteroids," Eur Respir Journ, 19:182-191 (2002).

Bartalena et al., "Management of Graves' Ophthalmopathy: Reality and Perspectives," Endocrine Reviews 21(2): 168-199 (2000).

Bartley, "The Epidemiologic Characteristics and Clinical Course of Ophthalmopathy Associated with Autoimmune Thyroid Disease in Olmstead County, Minnesota," Th. Am. Ophth. Soc., vol. XCII, (112 pgs.)(1994).

Bartley et al, "Clinical Features of Graves' Ophthahnopathy in an Incidence Cohort," Amer. Journ. Ophthalmology, 121:284-290 (1996).

Basadonna et al., "Plantar Fat Pad Atrophy After Corticosteroid Injection for an Interdigital Neuroma," Amer. Journ. Phys. Med. Rehabil. 1999; 78:283-285.

Benovic et al.. "Regulation of adenylyl cyclase-coupled $\beta$-adrenergic receptors." Ann Rev Cell Biol 1988; 4: 405-428.

Benzon et al., "Comparison of the Particle Sizes of Different Steroids and the Effect of Dilution," Anesthesiology, 106:331-8 (2007).

Bordaberry et al., "Repeated Peribulbar Injections of Triamcinolone Acetonide: a Successful and Safe Treatment for Moderate to Severe Graves' Ophthalmopathy," ACTA Ophthalmologica 2009; 87:58-64.

Bousquet-Melou, "beta-Adrenergic control of lipolysis in primate white fat cells: a comparative study with nonprimate mammals," Am J Physiol Regulatory Integrative Comp Physiol 267:115-123 (1994).

Carpene et al., "Adrenergic lipolysis in guinea pig is not a beta 3-adrenergic response: comparison with human adipocytes," Am J Physiol Regulatory Integrative Comp Physiol 266:905-913 (1994).

Caruso et al. "An evaluation of mesotherapy solutions for inducing . . . " J Plast Reconstr Aesthet Surg. 61(11):1321-4, Epub2007 (2008).

Clauser et al., "Rationale of Treatment in Graves Ophthalmopathy," Plastic and Reconstructive Surgery, vol. 108, pp. 1880-1894 Dec. 2001.

Collins et al., "Learning new tricks from old dogs: $\beta$-adrenergic receptors teach new lessons on firing up adipose tissue metabolism," Molecular Endocrinology First published Jul. 8, 2004 as doi:10. 1210/me.2004-0193 (22 pgs.) (2004).

De Ponte et al,, "New Approach to the Surgical Treatment of Severe Exophthalmos in Graves Disease," J. Craniofacial Surgery, vol. 9, No. 4, pp. 394-399 (1998).

Farias-Silva et al., "Stress-induces alteration in the lipolytic response to $\beta$-adrenoceptor agonists in rat white adipocytes," Journal of Lipid Research, vol. 40, 1719-1727 (1999).

Flechtner-Mors et al., "In Vivo $\alpha$1-Adrenergic Lipolytic Activity in Subcutaneous Adipose Tissue of Obese Subjects," Journ. of Pharm. and Exper. Therap., vol. 301, No. 1, pp. 229-233 (2002).

Galitzky et al., "Coexistence of $\beta$1-, $\beta$2-, and $\beta$3-adrenoceptors in dog fat cells and their differential activation by catecholamines," The Amer. Physiol. Society pp. E403-E412 (1993).

Galitzky et al., "Differential activation of $\beta$1-, $\beta$2-, and $\beta$3-adrenoceptors by catecholamines in white and brown adipocytes," Fundam. Clin. Pharmacol 9, 324-331 (1995).

Germack et al., "$\beta$-Adrenoceptor subtype expression and function in rat white adipocytes," British Journ. Pharma. 120, 201-210 (1997).

Gettys et al., "Age-Dependent Changes in $\beta$-Adrenergic Receptor Subtypes and Adenylyl Cyclase Activation in Adipocytes from Fischer 344 Rats," Endocrinology, vol. 136, No. 5, pp. 2022-2032 (1995).

Giudicelli et al., Eur J Biochem 99(3):457-62 (1979).

GreenWay et al., "Topical Fat Reduction," Obesity Research, vol. 3 Suppl. 561S-568S (1995).

Kendail-Taylor, et al, "Intravenous methylpredinisolone in the treatment of Graves; ophthalmopathy" BMJ 297(6663) 1574-1578 (1988).

Heine et al., "Increased adipose tissue in male and female estrogen receptor-$\alpha$ knockout mice,"PNAS, vol. 97, No. 23 12729-72734 (2000).

Hickey et al., Biomaterials 23:1649-1656, 2002.

January et al., "Salmeterol-induced desensitization, internalization and phosphorylation of the human $\beta$2-adrenoceptor." British Journal of Pharmacology, 123:701-711 (1998).

Jockers et al., "Desensitization of the $\beta$-Adrenergic Response in Human Brown Adipocytes," Endocrinology, vol. 139, No. 6, pp. 2676-2684 (1998).

Johnson, "Interactions between Corticosteroids and $\beta$2-Agonists in Asthma and Chronic Obstructive Pulmonary Disease," Proc Am Thorac Sou, vol. 1, pp. 200-206 (2004).

Johnson et al. "The pharmacology of salmeterol." Life Sci 1993: 52: 2131-2143.

Kazim et al., "Reversal of dysthyroid optic neuropathy following orbital fat decompression," Br. J. Ophthalmol. 84:600-605 (2000).

Kolata "Calorie-burning fat? Studies say you have it" The New York Times, (Apr. 8, 2009).

Kumar et al., "Evidence for Enhanced Adipogenesis in the Orbits of Patients with Graves' Ophthalmopathy," Journ. Clin. Endocrin. & Metab. 89(2):930-935 (2004).

Lafontan. "Fat Cells: Afferent and efferent messages define new approaches to treat obesity." Ann Rev Pharmacol Toxicol 45: 119-146, (2005).

Lafontan and Berlan "Fat cell adrenergic receptors and the control of white and brown fat cell function" J Lipid Res 34:1057-1091 (1993).

Lai et al., "Dexamethasome Regulates the β-Adrenergic Receptor Subtype Expressed by 3T3-L1 Preadipocytes and Adipocytes," Journ. Biol. Chem. vol. 257, No. 12, pp. 6691-6696 (1982).

Lonnqvist et al., "Lipolytic Catecholamine Resistance Due to Decreased β2-Adrenoceptor Expression in Fat Cells," J. Clin. Invest., vol. 90, pp. 2175-2186 (1992).

Mattson "Does brown fat protect against diseases of aging?" Ageing Res Rev 9(1):69-76 (2010).

Mauriege et al., "Human fat cell beta-adrenergic receptors: beta-agonist-dependent lipolytic responses and characterization of beta-adrenergic binding sites on human fat cell membranes with highly selective beta1-antagonists," Journ. Lipid Research, vol. 29, pp. 587-601 (1988).

Mori et al. "Rapid desensitization of lipolysis in the visceral and subcutaneous adipocytes of rats." Lipids 2007; 42(4). 307-314.

Murano, "Selection of Treatment Methods for Basedow's disease" Modern Physician 23 Ed 7, pp. 1103-1111 (2003).

Ng et al., "Combined orbital irradiation and systemic steroids compared with systemic steroids alone in the management of moderate-to-severe Graves' ophthalmopathy: a preliminary study," Hong Kong Med. J., vol. 11, No. 5, pp. 322-330 (2005).

Ohkawara et al., "Glucocorticoid-Induced Alteration of Beta-Adrenergic Adenylate Cyclase Response of Epidermis," Arch Dermatol Res 277:88-92 (1985).

Ohtsuka et al., "Effect of Steroid Pulse Therapy With and Without Orbital Radiotherapy on Graves' Ophthalmopathy," Am J Ophthalmol 135:285-290 (2003).

Papadopoulos et al., "The Clinical Picture: Soft Tissue Atrophy After Corticosteroid Injection," Cleveland Clinic Journ, Med., 2009; vol. 76 (6)373-374.

Sharma et al., "β-Adrenergic Receptor Blockers and Weight Gain a Systemic Analysis," Hypertension 37:250-254 (2001).

Taouis et al., "Characterization of Dog Fat Cell Adrenoceptors: Variations in Alpha-2 and Beta Adrenergic Receptors Distribution According to the Extent of the Fat Deposits and the Anatomical Location," Journ. Pharma. and Exper. Therap., vol. 242, No. 3. pp. 1041-1049 (1987).

GB 0804401.8 search report dated Apr. 15, 2009.

PCT/US10/36484 IPRP mailed Nov. 29, 2011 with Written Opinion.

EP06787329.9 Extended European search rpt dated Mar. 12, 2010.

EP 11180982 Search Report mailed Nov. 21, 2011.

PCT/US2011/021424 International Search Report mailed Sep. 21, 2011.

IL 198184 Exam Report mailed Dec. 4, 2011.

GB 1100628.5 Examination Report mailed Feb. 6, 2012.

GB 1008885.4 Examination Report mailed Nov. 18, 2011.

MX 200800570 Office Action mailed Nov. 18, 2011.

U.S. Appl. No. 12/760,258, filed Apr. 14, 2010.

U.S. Appl. No. 13/204,423, filed Aug. 5, 2011.

U.S. Appl. No, 13/303,045, filed Nov. 22, 2011.

U.S. Appl. No. 13/303,046, filed Nov. 22, 2011.

FDA 2002, pp. 1-2 (Update on Illegal Compounding of Clenbuterol Veterinary Drug Products).

Mamani-Matsuda et al., Long-acting beta2-adrenergic formoterol and salmeterol incude the apoptosis of B-Chronic lymphocytic leukemia cells, BR J. Haematol. Jan. 2004;124(2), printed from http://www.ncbi.nlm.nih.gov/pubmed/14687023, Abstract only, 2 pages.

Mcrea et al., "Salmeterol, a long-acting beta 2-adrenoceptor agonist mediating cyclic AMP accumulation in a neuronal cell line," Br. J. Pharmacol. Oct. 1993;110(2), printed rom http://www.ncbi.nlm.nih.gov/pubmed/7902176, Abstract only, 2 pages.

Sato et al., "Predition for effectiveness of steroid pulse therapy in the orbits of patients with Graves' ophthalmopathy," Nihon Naibunpi Gakkai Zasshi. Mar. 20, 1992;68(3), printed from http://www.ncbi.nln.nih.gov/pubmed/1582520, Abstract only, 2 pages.

Dobak, Formulations and Methods for Activating Brown Adipose Tissue , U.S. Appl. No. 12/760,258, filed Apr. 14, 2010.

Boulet et al., "Influence of obesity on response to fluticasone with or without salmeterol in moderate asthma," Respiratory Medicine (2007) 101, 2240-2247.

CN 200680031397.4 Office Action dated Feb. 14, 2012.

CN 20078004674 .1 Office Action dates Feb. 22, 2012.

EP11180982.8 Exam Report dated Mar. 14, 2012.

GB 1008885.4 Exam Report dated Apr. 4, 2012.

GB 1100628.5 Exam Report dated Feb. 6, 2012.

IL 198183 translation of Office Action dated Dec. 4, 2011.

U.S. Appl. No. 13/204,423 Office Action dated May 1, 2012.

U.S. Appl. No. 12/760,258 Office Action dated Apr. 2, 2012.

U.S. Appl. No. 12/763,030 Office Action dated May 7, 2012.

U.S. Appl. No. 13/007,518 Office Action dated Sep. 12, 2012.

McRea et al., "Salmeterol, a long-acting beta 2-adrenoceptor agonist mediating cyclic AMP accumulation in a neuronal cell line," Br. J. Pharmacol, Oct. 1993; 110(2), printed rom http://www.ncbi.nlm.nih.gov/pubmed/7902176, Abstract only, 2 pages.

Sato et al., "Predition for effectiveness of steroid pulse therapy in the orbits of patients with Graves' ophthalmopathy," Nihon Naibunpi Gakkai Zasshi. Mar. 20, 1992; 68(3), printed from http://www.ncbi.nlm.nih.gov/pubmed/1582520, Abstract only, 2 pages.

AU 2010253864 First Examiner's Report dated Jun. 15, 2012.

GB 1207749 Exam Report dated May 15, 2012.

GB 1008885.4 Exam Report dated Jul. 31, 2012.

KR 10-2009-70099772 Office Action dated Apr. 25, 2012 (English translation).

PCT/US2011/061972 Search report dated Jun. 15, 2012.

PCT/US2011/021424 International Preliminary Report on Patentability and Written Opinion dated Jul. 17, 2012.

PCT/US06/027405 Search rpt mailed Aug. 28, 2007.

U.S. Appl. No. 12/445,570 Office Action dated May 22, 2012.

U.S. Appl. No. 12/788,190 Office Action dated Jul. 16, 2012.

U.S. Appl. No. 13/096,895 Office Action dated Jun. 26, 2012.

U.S. Appl. No. 13/284,741 Office Action dated May 17, 2012.

Dobak, Formulations and Methods for Activating Brown Adipose Tissue ,' U.S. Appl. No. 12/760,258 filed Apr. 14, 2010.

Dobak, "Formulations for Treatment of Adipose Tissue, Cutaneous Tissue and Disorders, and Muscular Tissue." U.S. Appl. No. 12/445,571, filed Jan. 22, 2010.

Dobak, "Methods, Compositions, and Formulations for the Treatment of Thyroid Eye Disease." U.S. Appl. No. 12/445,570, filed Jan. 12, 2010.

Adcock "Molecular interactions between glucocorticoids and . . . " J Allergy Clin Immunol 110(6Suppl):S261-8 (2002).

Beers, et al. "The Merck Manual" 706-707 (1999).

Brodde et al. "Terbutaline-induced desensitization of Human . . . " J Clin Invest 76(3):1096-101 (1985).

Bronnegard et al. "Effect of Glucocorticosteroid treatment on glucocoritcoid receptor . . . " J Clin Endocrinol Metab 80(12):63608-12 (1995).

Burns, et al. "Regulation of lipolysis . . . " Lancet 1 (7441): 797-798 (1966).

Bujalska et al. "Characterisation of 11β-hydroxysteroid . . . " J Endocrinol 192(2):279-88 (2007).

Caruso et al. "Topical fat reduction from the waist" Diabetes Obesity Metabolism 9(3):300-303 (2007).

Chung "The complementary role of glucocorticosteroids and . . . " Allergy 53(42 Suppl): 7-13 (1998).

Cuirong, Study on the Effect of Hyaluronidase on Orbital Fibroblast, Chinese M.M. thesis, 2006, p. 2.

De Mazancourt et al. "Correction by dexamethasome treatment of the altered . . . " Horm Metab Red 22(1):22-4 (1990).

Farias-Silva et al. "Glucocorticoid receptor and Beta-adrenoceptor expression in . . . " Ann NY Acad Sci 1018:328-32 (2004).

Fries "Thyroid dysfunction: managing the ocular complications . . . " Geriatrics 47(2):58-60, 63-4, 70 (1992).

Fuller et al. "Fluticasone propionate—an update on . . . " Respir Med 89 Suppl A:3-18 (1995).

Gibaud et al. "Poly(e-caprolactone) and Eudragit microparticles containing . . . " Int J Pharm 28; 269(2):491-508 (2004).

Gittoes and Franklyn "Hyperthyroidism. Current treatment guidelines" Drugs 55(4):543-53 (1998).
Goodman "Permissive effects of hormones . . . " Endocrinology 86 (5):1064-1074 (1970).
Gronnenberg "Effects of Local . . . " Allergy 51(10):685-692 (1996).
Hadcock and Malbon "Regulation of β-adrenergic receptors by "permissive" hormones . . . " Proc Natl Acad Sci USA 85(22):8415-9 (1988).
Hiromatsu Basedow's Ophthalmopathy Japanese Publication New Regional Sales, No. 1, Syndromes, (2006).
Johnson "The β-Adrenoceptor" Am J Resp Crit Care Med 158:S146-S153 (1998).
Johnson The β-2-Adrenoceptors: mechanisms of action . . . Ped Resp Rev 2:57-62 (2001).
Kendall-Taylor et al. "Intravenous metylprednisolone in the treatment of . . . " BMJ 297(663):1574-8 (1988).
Lacasa et al "Permissive action of glucocorticoids on catecholamine-induced lipolysis . . . " Biochem Biophys Res Commun 153(2):489-97 (1988).
Langley et al. "Perioperative management of the thyrotoxic patient" Endocrinol Metab Clin North Am 32(2):519-34 (2003).
Laurent and Scopes "Hyaluronidase in the treatment . . . " 269 Edition No. 6889 pp. 537-538 (1955).
Louis, et al. "Role of β-Adrenergic Receptor . . . " Cardiovascular Drugs and Therapy 14(6):565-577 (2000).
Mak et al "Protective effects of a glucocorticoid on downregulation of . . . " J Clin Invest 96(1):99-106 (1995).
Marcocci et al. "Orbital cobalt irradiation combined with retrobulbar or systemic . . . " Clin Endocrinol (Oxf)27(1):33-42 (1987).
Mersmann "Beta-Adrenergic receptor modulation . . . " J. Animal Science 80:E24-E29 (2002).
Mirkin "Albuterol for weight control" www.DrMirkin.com (2009).
Nakai, et al. "Hypothyroid Grave's Disease concurring with . . . " Industrial Medical University agazine 25(3):333-3399 (2003).
Page et al. "β-Adrenergic receptor agonists increase apoptosis of adipose tissue in mice" Domes Anim Endocrinol 26(1):23-31 (2004).
Pederson et al. "Anti-glucocorticoid effects of progesterone in vivo . . . " Steroids 68:543-550 (2003).
Reynisdottir et al. "Effect of glucocorticosteroid treatment on beta-adrenoceptor . . . " Clin Sci 85(2):237-44 (1993).
Risse-Sundermann "The treatment of alopecia areata by intradermal injections of . . . " Dtsch med Wochenschr 85(15):584-586 (1960) (English Abstract Only).
Seco et al. "Acute and chronic treatment with glueocorticosteroids, modifying the beta . . . " Lung 173(5):321-8 (1995).
Shishiba "Selection of Treatment Methods for Basedow's Disease" Modern Physician 23rd edition 7, pp. 1103-1111 (2003).
West "Solid state chemistry and its applications" Wiley New York pp. 358-365 (1988).
Wiersinga and Prummel Graves' ophthalmopathy: a rational approach to treatment: Trends Endocrinol Metab 13(7)280-7 (2002).
Yip, et al, "Growth hormones and dexamethasone . . . " Endicrinology 140(3):1219-1227 (1999).
Yokoyama "Basedow's Disease Diagnosis and Treatment" 93rd edition No. 7 pp. 1077-1081 (2005).
AU 2006270165 Examiner's first rpt dated Dec. 24, 2009.
CN 200780046741.1 Office Action dated Nov. 20, 2012.
EA 201270683/26 Office Action dated Dec. 5, 2012.
EP06787329.9 Office Action mailed Jan. 31, 2011.
EP07843370 Search Rpt mailed Mar. 11, 2010.
EP07871172 Supplementary European search rpt dated Mar. 1, 2010.
GB 0718905.3 Search rpt dated Nov. 27, 2008 claims 31-13.
GB 0718905.3 Combined search and examination rpt dated Jan. 28, 2008.
GB 0718905.3 Examlnation rpt dated Nov. 27, 2008.
GB 0718905.3 Search rpt dated Nov. 27, 2008 claims 34-37 and 44.
GB 1100628.5 Examination report dated Feb. 6, 2012.
GB 1120090.4 Search and Examination Report mailed Dec. 9, 2011.
GB 1120091.2 Search and Examination Report mailed Dec. 9, 2011.
GB1008885.4 Examination report dated Nov. 18, 2011.
KR 10-2009-7009972 Office Action dated Apr. 26, 2012.
PCT/US07/079740 Search rpt mailed Jan. 30, 2008.
PCT/US07/081568 Search rpt mailed Jun. 17, 2008.
PCT/US10/36484 Search Rpt & Written Opn. Mailed Feb. 21, 2011.
U.S. Office Action mailed Aug. 24, 2009 in U.S. Appl. No. 11/457,436.
U.S. Office Action mailed Jan. 6, 2010 in U.S. Appl. No. 11/457,436.
U.S. Appl. No. 13/204,423 Office Action dated Dec. 5, 2012.
U.S. Appl. No. 12/763,030 Office Action dated Dec. 12, 2012.

* cited by examiner

Note: Total weekly dose SX defined by dose and frequency of injection;
1.0 μg FP injected with each dose of SX

*p<0.05
**p<0.01

METHODS FOR ADMINISTRATION AND FORMULATIONS FOR THE TREATMENT OF REGIONAL ADIPOSE TISSUE

CROSS REFERENCE

This application claims the benefit under §120 of U.S. application Ser. No. 12/788,190 filed May 26, 2010, which claims benefit to U.S. Appl. No. 61/181,627 filed May 27, 2009, U.S. Appl. No. 61/251,624 filed Oct. 14, 2009, and U.S. Appl. No. 61/289,972 filed Dec. 23, 2009, each of which is hereby incorporated by reference in its entirety.

BACKGROUND OF THE INVENTION

Excess body fat is a significant health care issue in modern societies. Chronic health conditions promoted by excess body fat include, e.g., cardiovascular disease and diabetes mellitus type 2. Moreover, excess body fat greatly undermines personal appearance and self image.

Accumulation of fat stores can occur unevenly in the body. For example, some persons may accumulate fat predominantly in visceral areas while others predominately in the subcutaneous tissue. Gender differences may also be apparent with women accumulating fat in the thighs and lateral buttocks and males in the waist. Women may accumulate fatty deposits of the thighs, which have a rumpled or "peau-de-orange" appearance, resulting in a condition referred to as cellulite. Cellulite may be related to skin architecture which allows subdermal fat herniation, sometimes referred to as adipose papillae. Other factors that may be related to cellulite include altered and/or reduced connective tissue septae, vascular and lymph changes that lead to fluid accumulation and inflammation. Fat tissue may also accumulate in the form of a fibrous fatty deposit known as a lipoma. Utilization of fat stores may occur unevenly. Persons who have lost substantial weight may still have regional pockets of fat accumulation that are resistant to reduction unless unhealthy extremes of weight loss are achieved. Exercise may affect subcutaneous fat stores differently, with deeper tissues responding with lipolysis and superficial stores being more resistant. Cellulite may also still be present despite weight loss, and lipomas are typically not affected by weight loss.

SUMMARY OF THE INVENTION

Described herein are subcutaneous and transcutaneous pharmaceutical formulations and methods of treatment using the pharmaceutical formulations for the treatment of regional adipose tissue. It has been determined that therapeutic effectiveness of a lipophilic long-acting selective beta-2 adrenergic receptor agonist and/or glucocorticosteroid, as evidenced for example by the change in circumference of a patient's waist, is achieved when a relatively low dose is administered to a patient. For example, in clinical trials, it is been determined that patients that were administered the lowest dose produced the greatest therapeutic response as measured by reduction in adipose tissue. It has also been determined that greater therapeutic effectiveness is achieved with less frequent weekly administrations of a lipophilic long-acting beta-2 adrenergic receptor agonist. For example, greater efficacy is provided to a patient when an amount equal to or less than about 0.5 μg of a lipophilic long-acting selective beta-2 adrenergic receptor agonist is administered to a patient once per week when compared to situations where about 10 μg of a lipophilic long-acting selective beta-2 adrenergic receptor agonist is administered to a patient twice per week. See, e.g., FIG. 4. It has been further determined that therapeutic efficacy of the formulations provided herein does not necessarily require a reduction in weight of the patient or alteration in exercise routine by the patient, but rather the efficacy of the pharmaceutical formulations and methods of treatment described herein is independent of these factors and influences. Accordingly, provided herein, in certain embodiments, are pharmaceutical formulations in optimal dosage amounts that provide maximal therapeutic effect in a patient.

In one aspect, described herein are pharmaceutical formulations and compositions that are suitable for subcutaneous injection comprising: (a) less than about 20 μg of an adipose tissue-reducing lipophilic long-acting selective beta-2 adrenergic receptor agonist or a salt thereof; and (b) at least one subcutaneously acceptable inactive ingredient. In another aspect, provided herein is a method for providing cosmetic fat reduction of a human comprising subcutaneously administering at or near the waist or abdomen a composition comprising: (a) less than about 20 μg of an adipose tissue-reducing lipophilic long-acting selective beta-2 adrenergic receptor agonist or a salt thereof; and (b) at least one subcutaneously acceptable inactive ingredient. In yet another aspect, provided herein is a method for providing a cosmetic waist or abdomen reduction of at least two centimeters in a human, comprising subcutaneously administering at or near the waist of the human a composition comprising (a) less than about 20 μg of an adipose tissue-reducing lipophilic long-acting selective beta-2 adrenergic receptor agonist or a salt thereof; and at least one subcutaneously acceptable inactive ingredient.

Also provided herein are pharmaceutical formulations for, in certain situations, reducing regional fat deposits in a subject. Further provided herein are pharmaceutical formulations that are formulated to provide a single session dose of salmeterol xinafoate in an amount that is about 5 ng to about 20 μg. In other embodiments, the formulation comprises a single session dose of fluticasone propionate in an amount that is between about 1 μg and about 300 μg. In still further embodiments, the formulation comprises a weekly dose of salmeterol xinafoate in an amount that is between about 5 ng to about 20 μg. In still further embodiments, the formulation comprises a weekly dose of fluticasone propionate in an amount that is between about 50 ng and about 25 μg. Also provided herein is a formulation that comprises a sub-dose of salmeterol xinafoate in an amount that is between about 1 ng to about 20 μg. In another embodiment, the formulation comprises a sub-dose of fluticasone propionate in an amount that is between about 5 ng to about 25 μg.

Also described herein is a method for reducing adipose tissue in a patient comprising subcutaneously administering a pharmaceutical formulation suitable for subcutaneous injection comprising: (a) a lipophilic long-acting selective beta-2 adrenergic receptor agonist or glucocorticosteroid, or a salt, optical isomer, racemate, solvate, or polymorph thereof; and (b) at least one subcutaneously acceptable inactive ingredient.

Described herein is a method for reducing the circumference of a patient's abdomen comprising subcutaneously administering at or near the patient's abdominal region a pharmaceutical formulation suitable for subcutaneous injection comprising: (a) a lipophilic long-acting selective beta-2 adrenergic receptor agonist or glucocorticosteroid, or a salt, optical isomer, racemate, solvate, or polymorph thereof; and (b) at least one subcutaneously acceptable inactive ingredient. In a specific embodiment, the circumference of the patient's abdomen is reduced by at least two centimeters as assessed by tape measure. In some embodiments, the two centimeter reduction in the patient's waist or abdomen is evident at about 4 to 8 weeks from the first day of treatment. In further or additional embodiments, the patient experiences a change in body weight during a treatment period of less than about 5%, less than about 3%, less than about 2%, less than about 1%, or less than 0.5%.

Provided herein is a method for treating regional fat accumulation comprising subcutaneously administering a pharmaceutical formulation suitable for subcutaneous injection comprising: (a) a lipophilic long-acting selective beta-2 adrenergic receptor agonist or glucocorticosteroid, or a salt, optical isomer, racemate, solvate, or polymorph thereof; and (b) at least one subcutaneously acceptable inactive ingredient.

Described herein is a method for inducing lipolysis in adipose tissue comprising subcutaneously administering a pharmaceutical formulation suitable for subcutaneous injection comprising: (a) a lipophilic long-acting selective beta-2 adrenergic receptor agonist or glucocorticosteroid, or a salt, optical isomer, racemate, solvate, or polymorph thereof; and (b) at least one subcutaneously acceptable inactive ingredient.

Described herein is a pharmaceutical formulation comprising an active ingredient consisting essentially of an adipose tissue-reducing amount of a lipophilic long-acting selective beta-2 adrenergic receptor agonist or a salt, optical isomer, racemate, solvate, or polymorph thereof and at least one subcutaneously acceptable inactive ingredient. In one embodiment, the lipophilic long-acting selective beta-2 adrenergic receptor agonist selectively partitions into adipose tissue relative to plasma. In another embodiment, the lipophilic long-acting selective beta-2 adrenergic receptor agonist is salmeterol. In yet another embodiment, the salt of salmeterol is a xinafoate salt. In a further embodiment, the at least one subcutaneously acceptable inactive ingredient is selected from about 0.5 to about 40% polyethylene glycol. In yet a further embodiment, the at least one subcutaneously acceptable inactive ingredient is selected from about 0.1 to about 10% polysorbate. In one embodiment, the polysorbate is polysorbate 80.

In another aspect, provided herein is a pharmaceutical formulation comprising an adipose tissue-reducing amount of salmeterol or a salt, optical isomer, racemate, solvate, or polymorph thereof and at least one subcutaneously acceptable inactive ingredient, wherein the formulation provides a mean plasma $C_{max}$ equal to or less than about 300 pg/mL when administered subcutaneously. In one embodiment, salmeterol selectively partitions into adipose tissue relative to plasma. In another embodiment, the formulation further comprises a glucocorticosteroid or a salt or solvate thereof. In yet another embodiment, the glucocorticosteroid is fluticasone or a salt thereof. In a further embodiment, the glucocorticosteroid is fluticasone propionate.

In yet a further embodiment, the formulations provide a mean fluticasone propionate plasma $C_{max}$ of about 1 to about 100 pg/mL. In some embodiments, the formulations provide a mean fluticasone propionate plasma $C_{max}$ that is undetectable using conventional methodology. In another embodiment, salmeterol and fluticasone propionate are co-administered in a single subcutaneous formulation.

In another aspect, provided is a pharmaceutical formulation comprising an adipose tissue-reducing amount of salmeterol or a salt, optical isomer, racemate, solvate, or polymorph thereof and at least one subcutaneously acceptable inactive ingredient, wherein the formulation provides a salmeterol partition ratio of between about 0.01 to about 0.2 when administered subcutaneously. In one embodiment, salmeterol selectively partitions into adipose tissue relative to plasma. In another embodiment, the salmeterol partition ratio is about 0.1.

In yet another aspect, provided is a method for reducing adipose tissue in a subject comprising subcutaneously administering to the subject a pharmaceutical formulation comprising an active agent consisting essentially of an adipose tissue-reducing amount of a lipophilic long-acting selective beta-2 adrenergic receptor agonist or a salt, optical isomer, racemate, solvate, or polymorph thereof and at least one subcutaneously acceptable inactive ingredient. In one embodiment, the lipophilic long-acting selective beta-2 adrenergic receptor agonist selectively partitions into adipose tissue relative to plasma. In another embodiment, the lipophilic long-acting selective beta-2 adrenergic receptor agonist is salmeterol. In yet another embodiment, the salt of the lipophilic long-acting selective beta-2 adrenergic agonist is a xinafoate salt. In a further embodiment, the pharmaceutical formulation further comprises a glucocorticosteroid or a salt or solvate thereof. In yet a further embodiment, the glucocorticosteroid is fluticasone propionate. In another embodiment, the pharmaceutical formulation provides a mean plasma fluticasone propionate $C_{max}$ of about 100 pg/mL to levels that are undetectable using conventional methodology.

In yet another aspect is a method for treating regional fat accumulation comprising subcutaneously administering to a regional fat accumulation area a pharmaceutical formulation comprising an adipose tissue-reducing amount of salmeterol or a salt, optical isomer, racemate, solvate, or polymorph thereof and at least one subcutaneously acceptable inactive ingredient, wherein the formulation provides a mean plasma $C_{max}$ equal to or less than about 300 pg/mL (including $C_{max}$ levels that are undetectable using conventional methodology). In one embodiment, salmeterol selectively partitions into adipose tissue relative to plasma. In another embodiment, the salt is a xinafoate salt. In yet another embodiment, the formulation further comprises a glucocorticosteroid or a salt, optical isomer, racemate, solvate, or polymorph thereof. In another embodiment, the formulation comprises fluticasone or a salt thereof. In a further embodiment, is a method for treating regional fat accumulation wherein the glucocorticosteroid is fluticasone propionate. In one embodiment, the formulation provides a mean plasma fluticasone propionate $C_{max}$ of about 100 pg/mL to levels that are undetectable using conventional methodology.

In one aspect provided herein is a method for reducing a regional fat deposit in a subject in need thereof comprising administering to the subject, a parenteral formulation consisting essentially of a therapeutically effective amount of at least one compound for reducing desensitization of beta-adrenergic receptors and a long-acting beta-2 adrenergic receptor agonist. In some embodiments, the parenteral formulation is administered by subcutaneous administration. In some embodiments, the at least one compound comprises a glucocorticosteroid. In another embodiment, the formulation comprises fluticasone or a salt thereof. In a further embodiment, is a method for treating regional fat accumulation wherein the at least one compound is fluticasone propionate. In some embodiments, the therapeutically effective amount of the at least one compound is in a form suitable for subcutaneous administration.

In some embodiments, the method further comprises administering, in addition to the at least one compound for reducing desensitization of beta-adrenergic receptors, a therapeutically effective amount a lipophilic long-acting beta-adrenergic agonist that is selective for the beta-2 adrenergic receptor (e.g., salmeterol). In some embodiments, the at least one compound for reducing desensitization of beta-adrenergic receptors, for example, fluticasone propionate, is administered subcutaneously prior to administration of the afore-described composition comprising a therapeutically effective amount of a lipophilic long-acting beta-adrenergic agonist.

In another aspect provided herein is a method for performing liposuction, comprising performing liposuction on a subject in need thereof that has been administered a pharmaceutical formulation suitable for subcutaneous administration comprising a therapeutically effective amount of at least one compound for reducing desensitization of beta-adrenergic receptors and a therapeutically effective amount of an adipose tissue-reducing amount of a lipophilic long-acting beta-adrenergic agonist that is selective for the beta-2 adrenergic receptor. Conversely, in another aspect provided herein is a method for performing liposuction, comprising performing liposuction on a subject in need thereof followed by administration of a pharmaceutical formulation suitable for subcutaneous administration comprising a therapeutically effective amount of at least one compound for reducing desensitization of beta-adrenergic receptors and a therapeutically effective amount of an adipose tissue-reducing amount of a lipophilic long-acting beta-adrenergic agonist that is selective for the beta-2 adrenergic receptor.

In a further aspect provided herein is a method for reducing a regional fat deposit in a subject in need thereof comprising administering to the subject a therapeutically effective amount of one or more adrenergic receptor pathway-active compounds (e.g., a catecholamine, an alpha adrenergic antagonist, forskolin, aminophylline, analogs thereof, or any combination thereof) and a therapeutically effective amount of at least one compound for reducing beta-adrenergic receptor desensitization (e.g., fluticasone propionate) and a therapeutically effective amount of an adipose tissue-reducing amount of a lipophilic long-acting beta-adrenergic agonist that is selective for the beta-2 adrenergic receptor (e.g., salmeterol xinafoate) in a formulation suitable for subcutaneous administration. In some embodiments, the therapeutically effective amount of the one or more adrenergic receptor pathway-active compounds and the therapeutically effective amount of an adipose tissue-reducing amount of a lipophilic long-acting beta-adrenergic agonist that is selective for the beta-2 adrenergic receptor are co-administered in a formulation suitable for subcutaneous administration. In another embodiment, the therapeutically effective amount of an adipose tissue-reducing amount of a lipophilic long-acting beta-adrenergic agonist selectively partitions into adipose tissue relative to plasma. In a further embodiment, is a formulation suitable for subcutaneous administration comprising an adrenergic receptor pathway-active compound (e.g., a catecholamine, an alpha adrenergic antagonist, forskolin, aminophylline, analogs thereof, or any combination thereof) and a long-acting beta-2 receptor agonist, such as salmeterol. In another embodiment is a formulation comprising an alpha adrenergic receptor antagonist and a long-acting beta-2 receptor agonist, suitable for subcutaneous administration.

In some embodiments, provided herein is a method of treating a patient comprising administering the patient a formulation comprising a single session dose of salmeterol xinafoate that is administered to a patient in an amount that is between about 0.5 ng to about 20 µg during each week of a 4-8 week treatment period. In still further embodiments, provided herein is a method of treatment comprising the administration of a formulation to a patient that comprises a single session dose of fluticasone propionate in an amount that is between about 1 µg and about 30 µg during each week of a 4-8 week treatment period.

In a further aspect provided herein is a method for treating a dermal condition, such as for example, psoriasis, hypopigmentation, stria, wrinkles, rhytids, vitiligo, and atopic dermatitis, in a subject in need thereof, comprising administering to the subject a pharmaceutical formulation comprising an active ingredient consisting essentially of an adipose tissue-reducing amount of a lipophilic long-acting beta-adrenergic agonist; and a subcutaneously acceptable carrier or excipient thereof.

BRIEF DESCRIPTION OF THE DRAWINGS

The features of the embodiments described herein are set forth with particularity in the appended claims. A better understanding of the features and advantages presently described herein will be obtained by reference to the following detailed description that sets forth illustrative embodiments, in which the principles are utilized, and the accompanying drawings of which:

FIGS. 3A and 3B demonstrate a dose-response effect with the treatment group receiving the 0.5 µg of salmeterol and 1 µg of fluticasone once per week for four weeks evidencing the greatest change in full waist circumference of about 3.5 cm.

FIG. 4 demonstrates a dose-therapeutic efficacy (based on change in waist or abdomen circumference) response curve based on a weekly dose of salmeterol.

once per week pursuant to the study described herein in Example 3A with reference to the plasma levels of salmeterol for the orally inhaled ADVAIR DISKUS® 500/50 drug product.

Figure 5A:
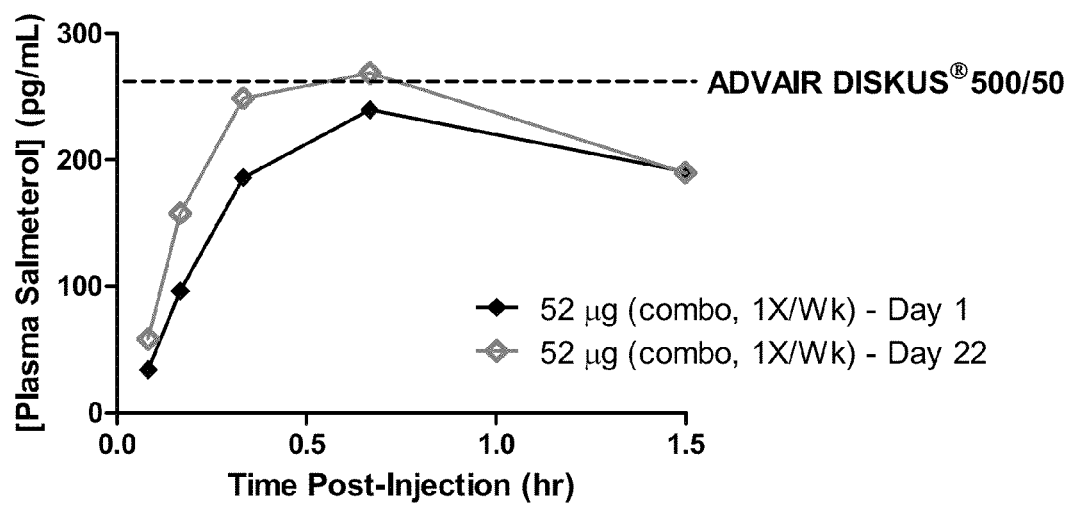
FIG. 5A is illustrative of a comparison of the plasma concentration (in pg/mL) at day 1 and day 22 of salmeterol xinafoate in human patients administered 52 µg salmeterol xinafoate (in combination with 22 µg fluticasone propionate)
Figure 5B:
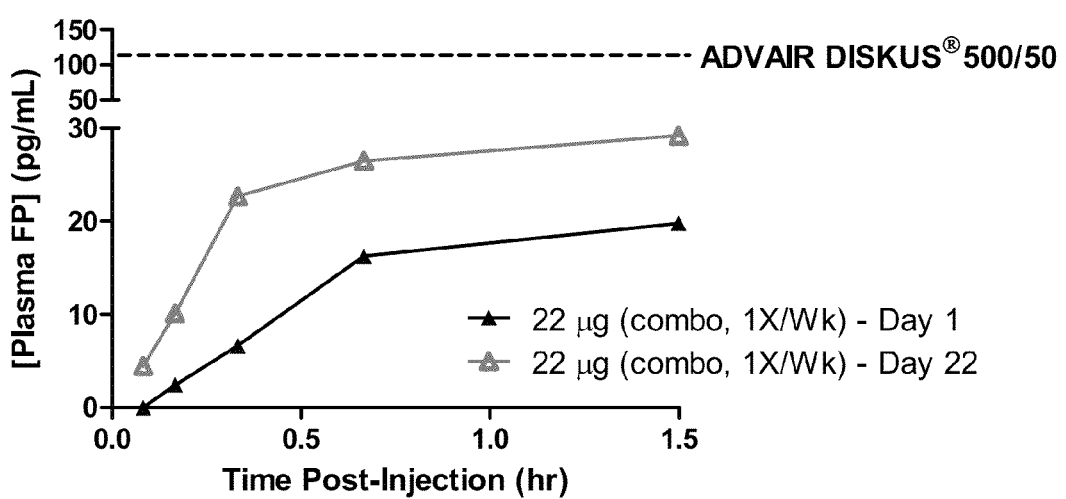

FIG. 5B is illustrative of the comparison of the plasma concentration (in pg/mL) at day 1 and day 22 of fluticasone propionate in human patients administered 22 μg fluticasone propionate (in combination with 52 μg salmeterol xinafoate) once per week pursuant to the study described herein in Example 3A with reference to the plasma levels of fluticasone for the orally inhaled ADVAIR DISKUS® 500/50 drug product. FIGS. 5A and 5B demonstrate that the systemic exposure limits of salmeterol xinafoate and fluticasone propionate will not exceed the pharmacokinetic limits of the commercially available ADVAIR DISKUS® 500/50 drug product. The increase in Cmax and AUC in the pharmacokinetic profiles depicted in FIGS. 5A and 5B is suggestive of tissue remodeling (resulting from a reduced amount of adipose tissue).

Figure 6:
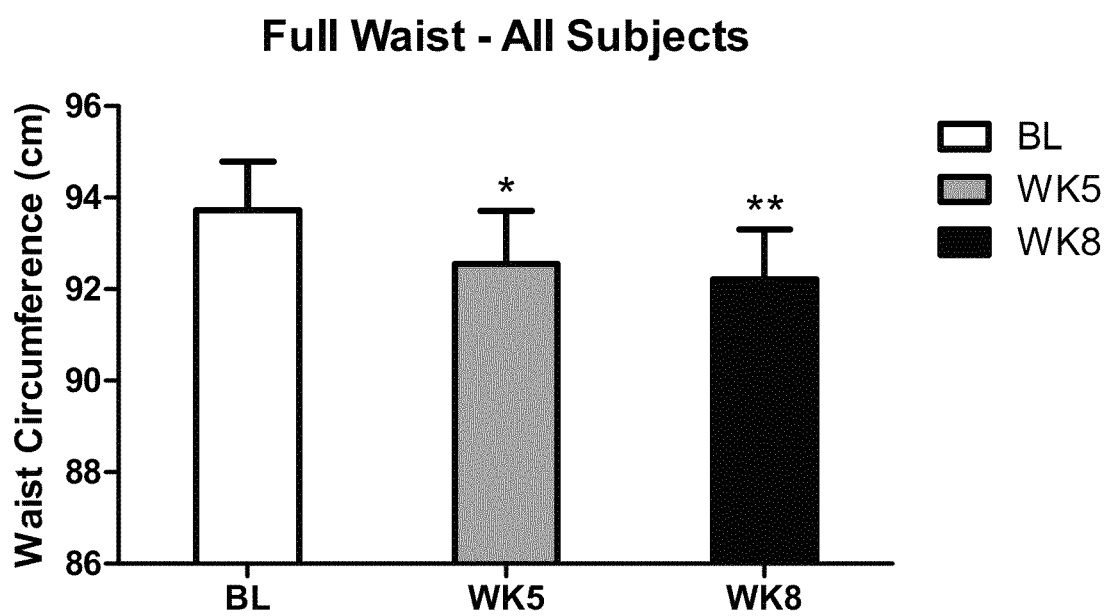
Figure 8:
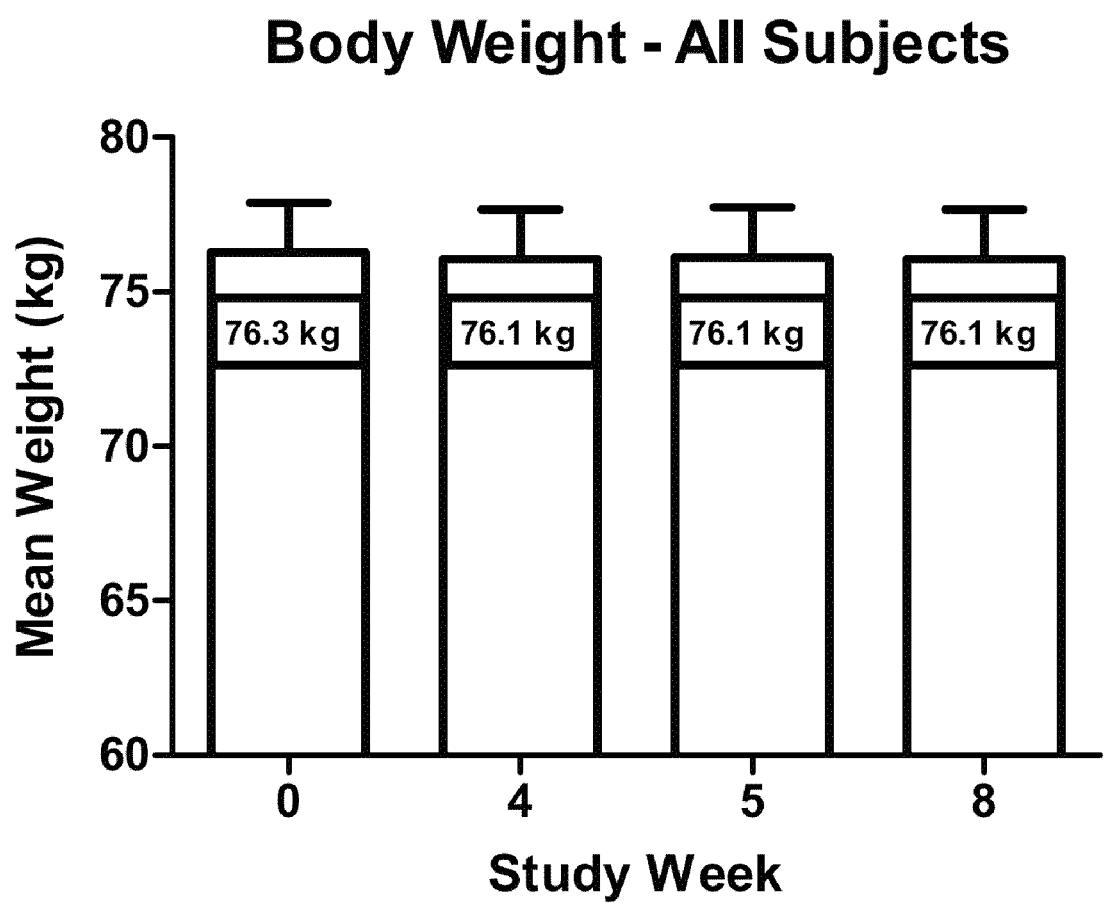

FIG. 6 is illustrative of the full waist circumference (in cm) for all patients at baseline, after 5 weeks, and after 8 weeks pursuant to the study described in Example 3B. FIG. 8 demonstrates that the mean waist or abdomen circumference was reduced in the patients enrolled in the study described in Example 3B.

Figure 7A:
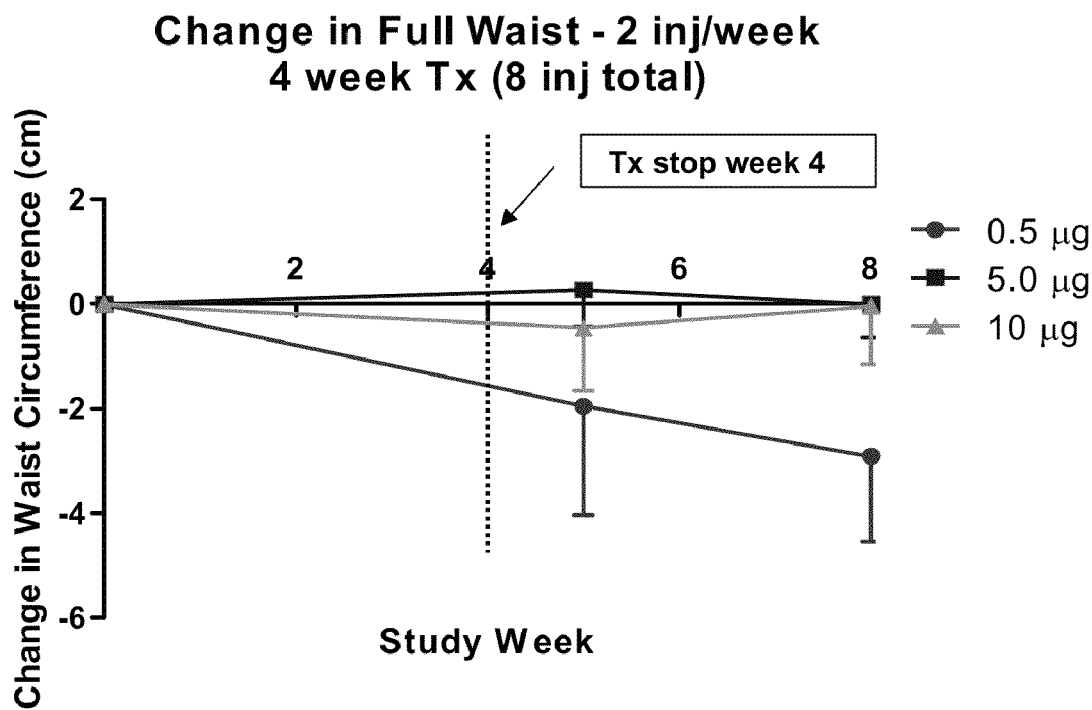

FIG. 7A is illustrative of the change in full waist circumference (in cm) from baseline over an 8 week period (including at time points of 1 week post-treatment and 4 weeks post-treatment) pursuant to the study described in Example 3B for patients in each of the following groups: (1) 0.5 μg of salmeterol and 1 μg of fluticasone twice per week for four weeks; (2) 5.0 μg of salmeterol and 1 μg of fluticasone twice per week for four weeks; and (3) 10 μg of salmeterol and 1 μg of fluticasone twice per week for four weeks.

Figure 7B:
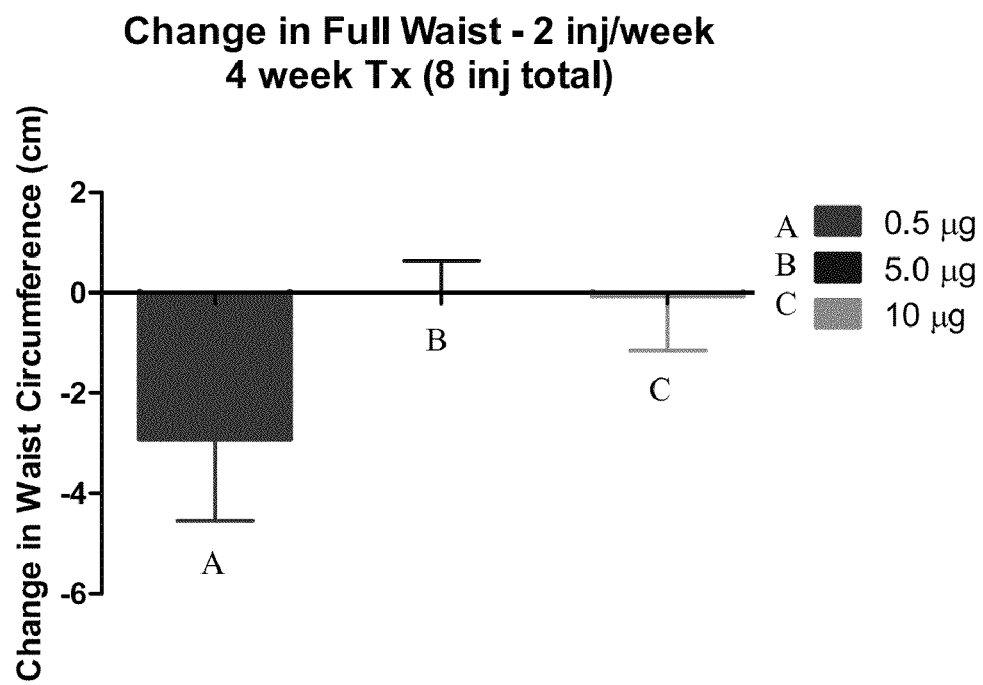

FIG. 7B is illustrative of the change in full waist circumference (in cm) from baseline after 8 weeks from the first day of treatment pursuant to the study described in Example 3B for patients in each of the following groups: (1) 0.5 μg of salmeterol and 1 μg of fluticasone twice per week for four weeks; (2) 5.0 μg of salmeterol and 1 μg of fluticasone twice per week for four weeks; and (3) 10 μg of salmeterol and 1 μg of fluticasone twice per week for four weeks. FIGS. 7A and 7B demonstrate a dose-related effect whereby the treatment group that received the 0.5 μg of salmeterol and 1 μg of fluticasone twice per week for four weeks evidenced the greatest change of about 2.9 cm with respect to patients receiving two injections per week.

FIG. 8 is illustrative of the mean body weight (in kg) at baseline, 4 weeks from start of treatment, 1 week post-treatment, and 4 weeks post-treatment, for all patients enrolled in the study described in Example 3B. FIG. 8 demonstrates that the patients enrolled in the study described in Example 3B did not evidence a significant change in weight during 8 weeks of study.

DETAILED DESCRIPTION OF THE INVENTION

Adipose tissue is the primary energy storage tissue of the body. Fat cells, or adipocytes, store this energy in the form of triglycerides. Triglycerides are mobilized from fat stores to provide caloric energy to the body through hormonal induction of triglyceride hydrolysis. This process releases free or non-esterified fatty acids and glycerol into the blood for use by other body tissues. The breakdown of triglycerides from fat store is referred to as lipolysis. Growth of new adipocytes also occurs, which is referred to as adipogenesis. One of the primary neurotransmitters that control lipolysis in the body are the catecholamines epinephrine and norepinephrine. Adipose tissue has beta-1, 2, and 3 adrenergic receptors and alpha-2 adrenergic receptors. Binding of beta-adrenergic receptor agonists ("beta-adrenergic agonists") to beta-adrenergic ("beta") receptors in adipose tissue results in adipocyte lipolysis. Beta-adrenergic receptor activation also inhibits adipogenesis. In humans, beta-2 receptors are the most abundant on fat cell surfaces and the primary mediator of beta-adrenergic receptor-stimulated lipolysis. Stimulation of lipolysis by beta-adrenergic agonists is mediated by adenylate cyclase and increased formation of cyclic adenosine monophosphate (cyclic AMP, cAMP).

Long-acting beta-2 adrenergic receptor agonists, such as salmeterol and formoterol, reduce regional fat deposits or adipose tissue regions by binding to beta receptors, resulting in adipocyte lipolysis. The use of long-acting beta-2 adrenergic receptor agonists, however, carries with it possible side effects that are potentially life-threatening. For example, use of long-acting beta-2 adrenergic receptor agonists may result in cardiovascular problems such as angina, hypertension or hypotension, tachycardia, palpitations, and arrhythmias. Thus, while long-acting beta-2 adrenergic receptor agonists may reduce regional fat deposits and adipose tissue regions they may also cause increased heart rate and palpitations.

It has been found that certain lipophilic long-acting selective beta-2 adrenergic agonists administered subcutaneously in appropriate amounts optionally with an appropriate amount of a certain glucocorticosteroid reduces regional fat deposits with limited systemic exposure compared to other long-acting beta-2 adrenergic agonists. One possible reason for this result is that the lipophilic nature of certain long-acting beta-2 adrenergic receptor agonists allows selective partitioning into the adipose tissue relative to plasma. The lipophilicity of certain long-acting beta-2 adrenergic receptor agonist contributes, in part, to providing relatively low levels of the agonist systemically. Combined with appropriately administered amounts via subcutaneous injection, certain lipophilic long-acting beta-2 adrenergic receptor agonists may provide therapeutic effectiveness in reducing regional fat deposits and/or adipose tissue with a reduced risk of producing cardiovascular side effects.

It has also been determined that of the doses of the formulations provided herein containing a lipophilic long-acting selective beta-2 adrenergic receptor agonist that have been administered to human patients, the lowest dose was the most effective. It has also been determined that greater therapeutic effectiveness is achieved with less frequent weekly administrations of a lipophilic long-acting beta-2 adrenergic receptor agonist. For example, it is been determined that greater efficacy is provided to a patient when about 10 μg of a lipophilic long-acting selective beta-2 adrenergic receptor agonist is administered to a patient once per week (and even greater therapeutic effect with administration of less than about 10 μg, for example an amount that is less than or equal to about 0.5 μg, when administered to the patient once per week) when compared to a dose of about 10 μg of a lipophilic long-acting selective beta-2 adrenergic receptor agonist that is administered twice per week. It has also been found that therapeutic efficacy, for example, as measured by a decrease in waist or abdomen circumference in patients administered a lipophilic long-acting selective beta-2 adrenergic receptor agonist and/or glucocorticosteroid does not necessarily require a reduction in weight or alteration in exercise routine of the patient.

Glossary of Certain Terminology

A "therapeutically effective amount," as used herein, refers to a sufficient amount of an agent (e.g., a long-acting beta-2 agonist) or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case can be determined using techniques, such as a dose escalation study. The term "therapeutically effective amount" includes, for example, a prophylactically effective amount. An "effective amount" of a compound disclosed herein, such as a selective beta-2 agonist used alone or in combination with other compounds (e.g., a compound for reducing beta-2 adrenergic receptor desensitization), is an amount effective to achieve a desired pharmacologic effect or therapeutic improvement without undue adverse side effects. It is to be understood that "an effect amount" or "a therapeutically effective amount" can vary from subject to subject, due to variation in metabolism of beta-2 agonists and compounds used in combination with beta-2 agonists (e.g., glucocorticosteroids), age, weight, general condition of the subject, the condition being treated, the severity of the condition being treated, and the judgment of the prescribing physician.

As used herein an "adipose tissue-reducing" amount refers to a sufficient amount of the lipophilic long-acting beta-2 adrenergic receptor agonist needed to reduce adipose tissue. It is to be understood that the amount sufficient to decrease the adipose tissue will vary from subject to subject due to variation in metabolism of the lipophilic long-acting beta-2 adrenergic receptor agonist, with age, weight, general condition of the subject, the severity of the condition being treated, and the judgment of the prescribing physician.

As described herein a "reduced or minimized risk of producing cardiovascular side effects" amount refers to an amount of the lipophilic long-acting beta-2 adrenergic receptor agonist used which does not result in clinically significant cardiovascular side effects. It is to be understood that the amount used will vary from subject to subject due to variation in metabolism of the lipophilic long-acting beta-2 adrenergic receptor agonist, with age, weight, general condition of the subject, the severity of the condition being treated, and the judgment of the prescribing physician.

"Plasma concentration" refers to the concentration of a substance such as a therapeutic agent, in blood plasma or blood plasma of a subject. It is understood that the plasma concentration of a therapeutic agent may vary many-fold between subjects, due to variability with respect to metabolism of therapeutic agents. In accordance with one aspect, the plasma concentration of a long-acting beta-2 adrenergic receptor agonist or a glucocorticosteroid varies from subject to subject. Likewise, in some embodiments, values such as maximum plasma concentration ($C_{max}$) or time to reach maximum plasma concentration ($T_{max}$), or total area under the plasma concentration time curve (AUC) varies from subject to subject. Due to this variability, the amount necessary to constitute "a therapeutically effective amount" of a lipophilic long-acting beta-2 adrenergic receptor agonist and/or a glucocorticosteroid is varies from subject to subject. It is understood that in some embodiments, when mean plasma concentrations are disclosed for a population of subjects, these mean values include substantial variation.

"Pharmacodynamics" refers to the factors that determine the biologic response observed relative to the concentration of drug at a site of action.

"Pharmacokinetics" refers to the factors that determine the attainment and maintenance of the appropriate concentration of drug at a site of action.

A "measurable plasma concentration" or "measurable plasma concentration" describes the blood plasma or blood plasma concentration, typically measured in mg, μg, or ng of therapeutic agent per mL, dL, or L of blood plasma, of a therapeutic agent that is absorbed into the bloodstream after administration. One in the field would be able to measure the plasma concentration or plasma concentration of a lipophilic long-acting beta-2 adrenergic receptor agonist or a glucocorticosteroid.

As used herein, the term "co-administered," refers to the administration of two or more therapeutic agents in a single formulation or separate formulations or routes of administration in any order for the purpose of treating the same health condition (e.g., a lipoma) in the same subject.

Some embodiments comprise optically pure isomers of the lipophilic beta-adrenergic agonist(s), which improve lipolysis and adipogenesis inhibition and reduce the risk of producing potential cardiovascular side effects. In some embodiments, these optically pure isomers allow formulations comprising larger loadings of an active ingredient, for example, by eliminating one or more isomers with no physiological effect, a lesser a physiological effect, a negative effect, and/or an undermined physiological effect. Removing the undesired bounds of a racemic mixture isolates the active isomer, or eutomer, thereby allowing more eutomer to be loaded in a give formulation by removing the inactive components.

Two stereogenic centers in a molecule generally generate two diastereomers, referred to herein as (R*,R*) and (R*,S*), and their enantiomers. Diastereomers are stereoisomers that are not enantiomers, that is, the mirror image of one diastereomer is not superimposable on another diastereomer. Enantiomers are stereoisomers that are mirror images of each other. A racemate is a 1:1 mixture of enantiomers. The enantiomers of the (R*,R*) diastereomers are referred to as the (R,R) and (S,S) enantiomers, which are mirror images of each other and therefore share some chemical and physical properties, for example melting points. Similarly, the (R,S) and (S,R) isomers are enantiomers of the (R*,S*) enantiomer. For example, some embodiments comprise optically pure isomers of other lipophilic beta-2 agonists, for example, (R)-salmeterol.

Additionally, in some embodiments, a lipophilic, long-acting selective beta-2 agonists is lipophilic, thereby providing a pharmaceutical formulation with activity in fat tissue. In some embodiments, the lipophilic agonist is salmeterol. In further embodiments, the lipophilicity of salmeterol provides prolonged exposure to the adipose tissue. In some embodiments, the agent is not salmeterol, but has a similar lipophilicity to salmeterol.

Salmeterol has high lipid solubility, compared to other long-acting beta-2 adrenergic receptor agonists, such as for example, formoterol, which extends its residence time in the adipose tissue and/or in one or more adipose cells. Some embodiments of the subcutaneous formulation comprise a highly lipophilic beta-adrenergic agonist, which reduces or eliminates the need for a sustained or controlled release carrier due to partitioning and sequestration in the adipose tissue thereby prolonging the treatment effect. In some embodiments, lipophilic beta-adrenergic agonists with an oil-water partition coefficient of at least about 1000 or at least about 10,000 to 1 are used. For example, salmeterol is at least 10,000 times more lipophilic than albuterol, a short-acting hydrophilic beta-adrenergic agonist.

A "treatment period" is defined as the period of time the patient is under a physician's care or direction, which may vary from patient to patient, and may be dependent on metabolism of the lipophilic long-acting beta-2 adrenergic receptor agonist, glucocorticosteroid, and/or other active ingredient administered to the patient, age, weight, general condition of the subject, the severity of the condition being treated, and the judgment of the prescribing physician. In some embodiments, the treatment period comprises between 1 week and 52 weeks, longer than 52 weeks, or any week in between 1 and 52.

A "weekly dose" is the total amount of active ingredient administered to a patient during a single week. For example, in situations with more than a single administration occurs during a week, the weekly dose is the total amount of active ingredient provided to the patient in each administration that occurs during the week.

A "periodic dose" is the frequency at which a dose is administered to a patient during a period.

A "single session dose" is the total amount of active ingredient administered to a patient during a single visit for treatment by a healthcare professional or, in situations of self-administration, a single session dose is the total amount of active ingredient administered to the patient by self-administration in a single session.

In some embodiments, a single session dose is divided into smaller amounts and administered to a patient in one or more "sub-doses." In some embodiments, each "sub-dose" is subcutaneously delivered to a patient by injection, e.g., using a syringe or is administered to the patient transcutaneously.

The phrases "patient" and "subject" are used interchangeably herein. In some embodiments, the patient or subject is a human. In further or additional embodiments, the patient or subject is an animal. In some embodiments, the animal is a human, a common household pet, including for example a cat or a dog, or a species of the animal kingdom. In some embodiments, the patient is a non-murine animal.

Active Ingredients

In one aspect, provided herein are pharmaceutical formulations suitable for subcutaneous or transcutaneous administration and methods of treatment comprising subcutaneously or transcutaneously administering to a patient a pharmaceutical formulation (including all of the methods of treatment described herein) wherein the pharmaceutical formulation comprises: (a) an adipose tissue-reducing amount of a lipophilic long-acting selective beta-2 adrenergic receptor agonist or glucocorticosteroid, or a salt, optical isomer, racemate, solvate, or polymorph thereof; and (b) at least one subcutaneously or transcutaneously acceptable inactive ingredient. In some embodiments, provided herein are pharmaceutical formulations, and methods of treatment, comprising administration of the pharmaceutical formulations to a patient, wherein the formulation is suitable for subcutaneous administration. In further or additional embodiments, the pharmaceutical formulation is suitable for transcutaneous administration.

In some embodiments, the pharmaceutical formulation comprises a lipophilic long-acting selective beta-2 adrenergic receptor agonist, or a salt, optical isomer, racemate, solvate, or polymorph thereof and a glucocorticosteroid, or a salt, optical isomer, racemate, solvate, or polymorph thereof. For example, in some embodiments, the lipophilic long-acting selective beta-2 adrenergic receptor agonist is salmeterol xinafoate and the glucocorticosteroid is fluticasone propionate.

In other embodiments, the pharmaceutical formulation consists essentially of a lipophilic long-acting selective beta-2 adrenergic receptor agonist, or a salt, optical isomer, racemate, solvate, or polymorph thereof. In still further embodiments, the pharmaceutical formulation consists essentially of a glucocorticosteroid, or a salt, optical isomer, racemate, solvate, or polymorph thereof. In additional embodiments, the pharmaceutical formulation consists essentially of a lipophilic long-acting selective beta-2 adrenergic receptor agonist and/or glucocorticosteroid, or a salt, optical isomer, racemate, solvate, or polymorph thereof.

Beta-2 Adrenergic Receptor Agonists

In one aspect, provided herein are pharmaceutical formulations suitable for subcutaneous or transcutaneous administration comprising a lipophilic long-acting selective beta-2 adrenergic receptor agonist, including, for example, salmeterol or 2-(hydroxymethyl)-4-{1-hydroxy-2-[6-(4-phenylbutoxy)hexylamino]ethyl}phenol, or its salts, optical isomers, racemates, solvates or polymorphs thereof and when used in the appropriate amounts and administered transcutaneously or subcutaneously, provides a therapeutic effect for reducing regional fat deposits and/or adipose tissue with limited systemic exposure, and consequently, a reduced risk of producing cardiovascular side effects. In one embodiment is a subcutaneous or transcutaneous preparation for the reduction of adipose tissue and/or the reduction in regional fat deposits comprising an adipose tissue-reducing amount of a lipophilic long-acting selective beta-2 adrenergic agonist wherein the formulation does not result in high systemic levels when administered subcutaneously or transcutaneously. In another embodiment, the lipophilic long-acting selective beta-2 adrenergic receptor agonist is salmeterol. In yet another embodiment, the agonist is a polymorph of salmeterol, such as for example, polymorph I and II. Such subcutaneous or transcutaneous preparations provide the required tissue concentration of salmeterol needed to reduce adipose tissue and/or reduce regional fat deposits with a minimized or reduced risk of producing the side effects typically associated with the administration of beta-2 adrenergic receptor agonists, including other long-acting beta-2 adrenergic receptor agonists. Additionally, the use of salmeterol in a subcutaneous or transcutaneous preparation provides therapeutically effective dosages without producing relatively high systemic levels found when using other long-acting beta-2 adrenergic receptor agonists, such as for example, formoterol.

In another aspect, provided herein are pharmaceutical formulations suitable for subcutaneous or transcutaneous administration and methods of treatment comprising subcutaneously or transcutaneously administering to a patient a pharmaceutical formulation (including all of the methods of treatment described herein) wherein the pharmaceutical formulation comprises a beta-2 adrenergic receptor agonist.

In some embodiments, provided herein are pharmaceutical formulations and methods of treatment comprising a beta-2 adrenergic receptor agonist, or a salt, optical isomer, racemate, solvate, or polymorph thereof, that is characterized by at least one of the following properties: lipophilic; selective for the beta-2 adrenergic receptor; and long-acting. In some embodiments, the beta-2 adrenergic receptor agonist is selective for the beta-2 adrenergic receptor. In further or additional embodiments, the beta-2 adrenergic receptor agonist is lipophilic. In further or additional embodiments, the beta-2 adrenergic receptor agonist is long-acting.

In some embodiments, the beta-2 adrenergic receptor agonist is bambuterol, bitolterol, broxaterol, carbuterol, carmoterol, clenbuterol, ibuterol, sulfonterol, isoproterenol, trimetoquinol, formoterol, desformoterol, hexoprenaline, ibuterol, indacaterol, isoetharine, isoprenaline, isoproterenol, levalbuterol, metaproterenol, picumeterol, pirbuterol, procaterol, reproterol, rimiterol, salbutamol, salmeterol; sulfonterol, terbutaline, trimetoquinol, tulobuterol, TA-2005 (8-hydroxy-5-((1R)-1-hydroxy-2-(N-((1R)-2-(4-methoxyphenyl)-1-methylethyl-)amino)ethyl)-carbostyril hydrochloride), QAB-149 (Novartis), TA-2005, GSK-159797, or GSK-642444, or a salt, optical isomer, racemate, solvate, or polymorph thereof.

In some embodiments, the beta-2 adrenergic receptor agonist is long-acting and is selected from salmeterol, formoterol, bambuterol, or clenbuterol. In further or additional embodiments, the beta-2 adrenergic receptor agonist is ultra long-acting. In some embodiments, the ultra long-acting beta-2 adrenergic receptor agonist is selected from indacaterol, carmoterol, QAB-149, CHF-4226, TA-2005, GSK-159797, and GSK-642444.

In some embodiments, provided herein are pharmaceutical formulations comprising an active ingredient consisting essentially of an adipose tissue-reducing amount of a lipophilic long-acting selective beta-2 adrenergic receptor agonist or a salt, optical isomer, racemate, solvate, or polymorph thereof and at least one subcutaneously or transcutaneously acceptable inactive ingredient. In one embodiment, the lipophilic long-acting selective beta-2 adrenergic receptor agonist selectively partitions into adipose tissue relative to plasma.

In another embodiment, the lipophilic long-acting selective beta-2 adrenergic receptor agonist is salmeterol(±2-(hydroxymethyl)-4-[1-hydroxy-2-[6-(4-phenylbutoxy)hexylamino]ethyl]-phenol, CAS Reg. No. 94749-08-3, shown below as compound 1).

and at least a second active ingredient, wherein the formulation is suitable for subcutaneous or transcutaneous administration.

Lipophilic, long-acting, selective beta-2 agonists, for example, salmeterol are used in some embodiments. In other embodiments, salts, optical isomers, racemates, polymorphs, and/or solvates of beta-2 agonists have the desired activity and are accordingly provided for herein. Unless otherwise specified, references to an active ingredient, for example, to salmeterol, include the compound itself as well as a physiologically acceptable analogs, salts, optical isomers, racemates, polymorphs, solvates, or combinations thereof.

In some embodiments, salmeterol is used in the compositions and methods described herein. Depending on the tissue, salmeterol may exhibit partial agonist activity, which is believed to reduce receptor desensitization and may limit arrestin signaling leading to less receptor down-regulation. In some embodiments, salmeterol is present as a physiologically acceptable salt, optical isomer, racemate, solvate, and/or polymorph thereof. Suitable physiologically acceptable salts of salmeterol include, but are not limited to acid addition salts derived from inorganic and organic acids, such as the hydrochloride, hydrobromide, sulfate, phosphate, maleate, tartrate, citrate, benzoate, 4-methoxybenzoate, 2-hydroxybenzoate, 4-hydroxybenzoate, 4-chlorobenzoate, p-toluenesulphonate, methanesulphonate, ascorbate, salicylate, acetate, fumarate, succinate, lactate, glutarate, gluconate, tricarballylate, hydroxynaphthalenecarboxylate, 1-hydroxy-2-naphthalenecarboxylate, 3-hydroxy-2-naphthalenecarboxylate, oleate,

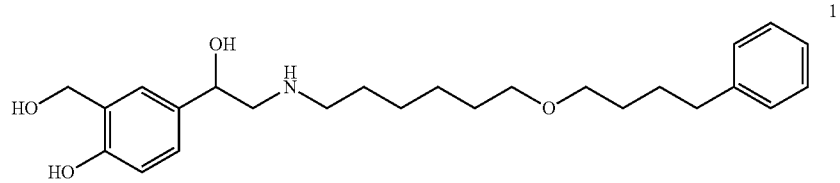 [SMILES: OCc1cc(C(O)CNCCCCCCOCCCCc2ccccc2)ccc1O]

combinations thereof, and the like. In some embodiments, salmeterol is provided as the 1-hydroxy-2-naphthalene carboxylate salt (hydroxynaphthoate, also known as xinafoate).

Agents for Reducing or Preventing Desensitization

Beta-adrenergic activity is enhanced by preventing or reducing desensitization (tachyphylaxis) that can occur with continuous exposure of adipocytes to adrenergic agonists as discussed above. "Compounds that reduce desensitization of beta-adrenergic receptors" (e.g., reduce desensitization of a target tissue to a beta-adrenergic agonist) include all suitable compounds that reduce tolerance of the target tissue to the beta-adrenergic receptor agonists, including glucocorticosteroids and suitable antihistamines, for example, ketotifen, and thyroid hormones, for example T3 and T4.

Glucocorticosteroids are also referred herein as "anti-inflammatory steroids," "glucocorticosteroids," and/or "corticosteroids." Glucocorticosteroids are believed to sensitize regional fat accumulations by increasing the number of surface beta-2 receptors, thereby favoring lipolysis or fat reduction over fat storage. It is also understood that glucocorticosteroids also decrease the number of alpha-2 receptors. Glucocorticosteroids also stabilize or reduce receptor down-regulation especially when given simultaneously with a beta-adrenergic agonist. Of note, estrogen can induce the expression of alpha-2 adrenergic receptors in subcutaneous adipose tissue in women resulting in a ratio of beta-2 receptor to alpha-2 receptor of less than 1. Thus, in one embodiment is a In other embodiments, the lipophilic, long-acting, selective beta-2 agonist is a polymorph of salmeterol. In a further embodiment, the polymorph is polymorph I or II. In further embodiments, the formulation uses a mixture of salmeterol polymorphs. In yet another embodiment, the salt of the lipophilic long-acting selective beta-2 adrenergic receptor agonist is a xinafoate salt. In some embodiments, the lipophilic long-acting selective beta-2 adrenergic receptor agonist is salmeterol xinafoate.

Some embodiments provide adrenergic modulation through the use of pharmaceutical compositions comprising an adipose tissue-reducing and lipophilic, long-acting selective beta-2 receptor agonist active ingredient administered subcutaneously or transcutaneously, either alone (as single agent therapy), or in combination with at least a second active ingredient (as a combination therapy). Thus, in some embodiments, the pharmaceutical formulations (and corresponding methods of treatment provided herein) consist essentially of a lipophilic, long-acting, selective beta-2 agonist, for example, salmeterol, physiologically acceptable salts, optical isomers, racemates, solvates, polymorphs, or combinations thereof, wherein the formulation is suitable for subcutaneous or transcutaneous administration. In further or additional embodiments, the pharmaceutical formulation comprises a lipophilic, long-acting, selective beta-2 agonist, for example, salmeterol, physiologically acceptable salts, optical isomers, racemates, solvates, polymorphs, or combinations thereof, pharmaceutical composition comprising a beta-2 receptor agonist in combination with an alpha-2 antagonist and a pharmaceutically acceptable excipient. In one embodiment, the composition is suitable for subcutaneous or transcutaneous administration.

Glucocorticosteroids

Some embodiments of the composition comprising one or more glucocorticosteroids are effective in treating regions of fat comprising a reduced number of beta-2 receptors and or an increased number of alpha-2 receptors, which are resistant to beta-adrenergic stimulation of lipolysis or inhibition of adipogenesis, for example, subcutaneous adipose tissue, especially in women.

Without wishing to be bound by theory, it is believed that glucocorticosteroids or other compounds for reducing desensitization of beta-adrenergic receptors increase lipolysis, adipogenesis inhibition, and/or regional fat reduction during beta-adrenergic agonist exposure. Thus, in some embodiments, a therapeutically effective amount of a compound (e.g., a glucocorticosteroid) for reducing desensitization of beta-adrenergic receptors is administered to increase lipolytic activity and/or increase the number of beta-receptors in the target tissue, and thereby increase fat deposit reduction. In some embodiments, a patient is administered a pharmaceutical formulation suitable for subcutaneous or transcutaneous administration comprising a therapeutically effective amount of a long-acting beta-2 adrenergic receptor agonist and a glucocorticosteroid. For example, the compound for reducing desensitization of beta-adrenergic receptors is formulated suitable for subcutaneous administration. In further or additional embodiments, the compound for reducing desensitization of beta-adrenergic receptors is formulated suitable for transcutaneous administration. In some embodiments, the pharmaceutical formulation further comprises a therapeutically effective amount of a lipophilic selective beta-2 adrenergic agonist that is selective for the beta-2 adrenergic receptor (e.g., salmeterol). In some embodiments, the lipophilic selective beta-adrenergic agonist is formulated as a subcutaneous or transcutaneous formulation.

In some embodiments, a compound for reducing desensitization of beta-adrenergic receptors is a glucocorticosteroid. Thus, in certain embodiments, provided herein are pharmaceutical formulations and methods of treatment comprising subcutaneously or transcutaneously administering to a patient a pharmaceutical formulation (including all of the methods of treatment described herein) wherein the pharmaceutical formulation comprises: (a) an adipose tissue-reducing amount of a lipophilic long-acting selective beta-2 adrenergic receptor agonist or glucocorticosteroid, or a salt, optical isomer, racemate, solvate, or polymorph thereof; and (b) at least one subcutaneously or transcutaneously acceptable inactive ingredient. In some embodiments, provided herein are pharmaceutical formulations, and corresponding methods of treatment, comprising administration of the pharmaceutical formulations to a patient, wherein the formulation is suitable for subcutaneous administration. In further or additional embodiments, the pharmaceutical formulation is suitable for transcutaneous administration.

In some embodiments, the pharmaceutical formulation comprises a lipophilic long-acting selective beta-2 adrenergic receptor agonist, or a salt, optical isomer, racemate, solvate, or polymorph thereof and a glucocorticosteroid, or a salt, optical isomer, racemate, solvate, or polymorph thereof. In certain embodiments, the glucocorticosteroid is selected from fluticasone, mometasone, beclomethasone, triamcinolone, fluniolide, ciclesonide, or budesonide, or a salt, optical isomer, racemate, solvate, or polymorph thereof.

In other embodiments, the glucocorticosteroid is fluticasone or a salt, optical isomer, racemate, solvate, or polymorph thereof. In specific embodiments, the lipophilic long-acting selective beta-2 adrenergic receptor agonist is salmeterol xinafoate and the glucocorticosteroid is fluticasone propionate. In yet another embodiment, the glucocorticosteroid is fluticasone furoate, or a salt, optical isomer, racemate, solvate, or polymorph thereof. In some embodiments, the glucocorticosteroid is fluticasone propionate (shown below as compound 2), or its analogs, prodrugs, metabolites, and isomers thereof.

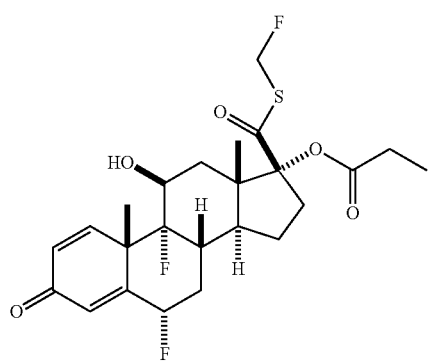

In one aspect, provided herein is an agent for reducing desensitization of beta-adrenergic receptors and thereby increasing lipolysis, adipogenesis inhibition, and/or regional fat reduction during beta-adrenergic agonist exposure. In some embodiments, provided herein is a pharmaceutical composition comprising at least one compound that reduces desensitization of beta-adrenergic receptors, including glucocorticosteroids, including for example fluticasone propionate or fluticasone furoate, whereby the compound is administered subcutaneously or transcutaneously, either alone (as single agent therapy), or in combination with at least a second active ingredient (as a combination therapy). Thus, in some embodiments, the pharmaceutical formulations (and corresponding methods of treatment provided herein) consist essentially of a glucocorticosteroid, for example, fluticasone, physiologically acceptable salts, optical isomers, racemates, solvates, polymorphs, or combinations thereof, wherein the formulation is suitable for subcutaneous or transcutaneous administration. In further or additional embodiments, the pharmaceutical formulation comprises a glucocorticosteroid, for example, fluticasone, physiologically acceptable salts, optical isomers, racemates, solvates, polymorphs, or combinations thereof, and at least a second active ingredient, wherein the formulation is suitable for subcutaneous or transcutaneous administration.

In various embodiments, the lipophilic, long-acting selective beta-2 adrenergic receptor agonists are administered separately or in combination with one or more compounds that reduce desensitization of the target tissue to the beta-adrenergic receptor agonist(s), for example, glucocorticosteroids or ketotifen, or analogs thereof. The term desensitization includes both short-term desensitization (tachyphylaxis), as well as long-term desensitization, as well as desensitization over other time periods. Beta-2 adrenergic receptor agonists are also referred to herein as "beta-2 agonists" and "beta-2 receptor agonists." Unless otherwise specified, references to beta-2 adrenergic receptor agonists also include their analogs, physiologically acceptable salts, optical isomers, racemates, solvates, and/or polymorphs thereof. Some embodiments of the subcutaneous formulation comprise from about 400:1 to about 1:400 lipophilic, long-acting selective beta-2 agonist to glucocorticosteroid. In further or additional embodiments, the subcutaneous formulation comprise from about 200:1 to about 1:200 lipophilic, long-acting selective beta-2 agonist to glucocorticosteroid.

In some embodiments, a formulation for use in the methods described herein comprises a combination of the lipophilic, long-acting selective beta-2 agonists, such as salmeterol and physiologic salts, optical isomers, racemates, solvates of polymorphs thereof and a glucocorticosteroid wherein the combination is suitable for subcutaneous administration. Without wishing to be bound by theory, it is believed that the combination of these compounds has an enhanced effect, by way of a non-limiting example, in improving the appearance of regional fat accumulations and cellulite. Accordingly, provided herein are synergistic pharmaceutical formulations that are suitable for subcutaneous and/or transcutaneous administration to a patient comprising a lipophilic, long-acting selective beta-2 agonists and compounds that reduce desensitization of beta-adrenergic receptors. In some embodiments, the combination of these two active ingredients provides a therapeutic effect when co-administered that is greater than the sum of the therapeutic effect when administered separately, i.e. when not co-administered.

Dosing of Active Ingredients

In some embodiments, long-term exposure of adipose tissue to adrenergic agents, particularly beta-adrenergic receptor agonists, results in receptor desensitization through receptor phosphorylation and sequestration. These effects limit the ability of an adrenergic modulating composition to treat adipose tissue and result in tachyphylaxis, a condition in which the body experiences a rapidly decreasing response to the agonist following administration of the initial doses, to the desired lipolytic and anti-adipogenesis effect. Consequently, in certain situations with long-term exposure of adipose tissue to beta-adrenergic receptor agonists, the therapeutic effect with the beta-adrenergic receptor agonists is short-lived.

Repeated administration of short-acting beta-2 agonists often result in tachyphylaxis, as discussed above. However, salmeterol, exhibits partial beta-2 receptor agonist activity in some systems that may reduce the desensitization that occurs with continuous exposure of adipocytes to full adrenergic receptor agonists. Compared with short-acting beta-2 agonists, lipolysis also occurs for a longer time after administration because lipophilic, long-acting selective beta-2 agonists have longer half-lives. The combination of longer half-lives and activities reduces the required frequency and total dosage of administration of the pharmaceutical compositions provided herein. Consequently, in some embodiments, daily administration or more than once daily administration of the composition is not required. In some embodiments, provided herein are subcutaneously or transcutaneously administered adipose tissue-reducing lipophilic, long-acting selective beta-2 agonists which exhibit greater selectivity for beta-2 receptors, permitting substantially similar therapeutic effects with less selective beta-2 agonists at a lower dosage and/or less frequent dosage. Further the more selective beta-2 activity can limit cardiac and other systemic side effects, which in the case of cardiac side effects, is often induced by beta-1 receptor stimulation in the heart. In some embodiments, provided are subcutaneous or transcutaneous formulations of lipophilic, long-acting beta-2 agonists which provide selectivity for beta-2 receptors while reducing the risk of producing cardiac or systemic side effects.

In some embodiments, beta-2 receptor activity or density increases in adipocytes within a regional fat deposit in response to glucocorticosteroid administration, particularly in the presence of a beta-adrenergic agonist. In some embodiments, increasing beta-2 receptor activity and/or density potentiates the effect of long- and short-acting beta-2 agonists. Thus, in some embodiments, the glucocorticosteroid sensitizes adipose tissue in a regional fat deposit to the effects of beta-2 receptor stimulation, e.g., lipolysis, inhibition of adipogenesis, and/or apoptosis, and/or increases the ratio of beta-2 adrenergic receptors to alpha-2 adrenergic receptors, thereby shifting the balance of the adipose tissue from fat accumulation to fat loss and resulting in reduction of the regional fat deposit. In some embodiments, beta-2 receptor number is increased or maintained especially with a glucocorticosteroid.

Provided herein are pharmaceutical formulations that are suitable for subcutaneous or transcutaneous administration. In some embodiments, the pharmaceutical formulations provided herein are suitable for subcutaneous injection, and provide for a volume of up to about 20 mL (including, e.g., about 0.1 mL, about 0.3 mL, about 0.5 mL, about 0.7 mL, about 1.0 mL, about 1.1 mL, about 1.5 mL, about 2 mL, about 2.5 mL, about 3 mL, about 3.5 mL, about 4 mL, about 5 mL, about 6 mL, about 7 mL, about 8 mL, about 9 mL, or any other volume from about 0.1 mL to about 20 mL) of an excipient compatible with subcutaneous administration. In some embodiments, the excipient concentration is kept below 1% (e.g., about 0.05%, about 0.2%, about 0.3%, about 0.4%, about 0.5%, about 0.6%, about 0.8%, or any other concentration from about 0.05% to less than about 1%.

Periodic Dosing Schedule

Another aspect of the formulations and methods of treatment provided herein is a periodic dosing schedule. It has been determined that once per week dosing of a lipophilic long-acting selective beta-2 adrenergic receptor agonist, e.g., salmeterol xinafoate, is more efficacious than twice per week dosing. For example, it has been shown in a human clinical trial that administering to a patient all of the active ingredient, including any sub-doses, in a single session dose that occurs once per week is more efficacious than administering to a patient the active ingredient in two session doses per week. See, e.g., FIGS. 3B and 7B.

A periodic dose is the frequency at which a single session dose is administered to a patient during a period. For example, in some embodiments, the periodic dose is once per week, and hence in these situations a patient will receive a single session dose once per week. In further or additional embodiments, the periodic dose is 2-7 times per week (including any interval between 2 and 7), 3-6 times per week (including any interval between 3 and 6), or 4-5 days per week. In some embodiments, the periodic dose is 1-4 times per month (including any interval between 1 and 4), 2-3 times per month, or once or twice per month. In some embodiments, the periodic dose is 1-52 times per year (including any interval between 1 and 52).

Because the single session doses provided herein are based on once per week dosing, in situations where the periodic dose is different than once per week, in certain situations the single session dose amount administered to the patient is normalized to account for this difference. For example, in some situations where the periodic dose is twice per week, the patient will receive the single session doses in two separate halves (that are about equal or unequal) during the week compared to what is provided herein. Similarly, in some situations where the periodic dose is seven times per week, the amount of active ingredient administered to the patient for each single session dose compared to what is provided herein is divided by seven. As another example, in certain situations where the periodic dose is once per month, the patient will receive a single single session dose per month at four times the amount that is provided herein.

Single Session Dose

An additional aspect of the formulations and methods of treatment provided herein is a single session dose. A single session dose is the total amount of active ingredient administered to a patient during a single visit for treatment by a healthcare professional or, in situations of self-administration, it is the amount of active ingredient administered to the patient by self-administration in a single session. The single session doses provided herein are based on a once per week periodic dose, and can be adjusted for a different periodic dose than once per week as provided herein. As discussed herein, in some embodiments a single session dose includes 20 or more sub-doses.

Figure 4:
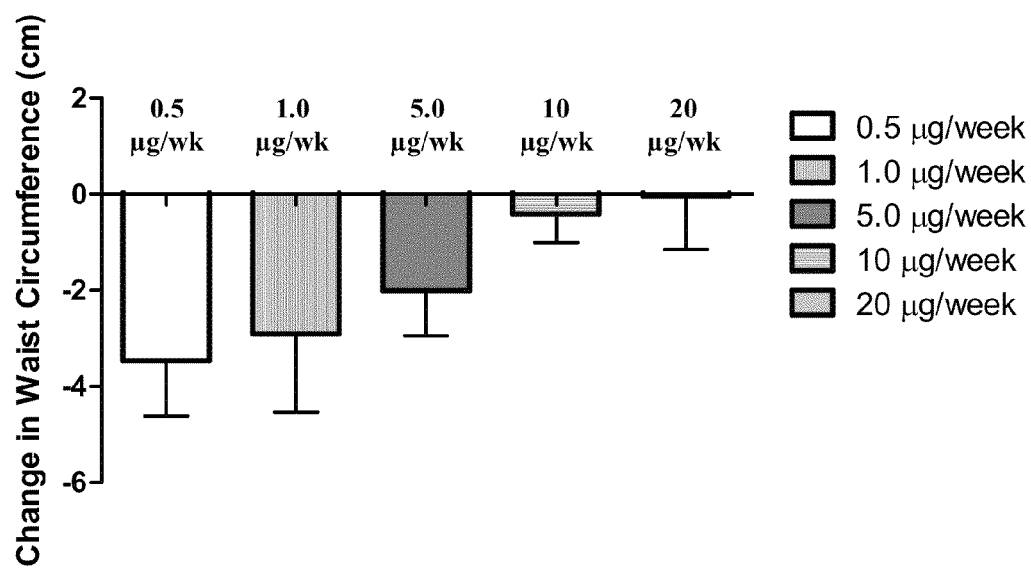
FIG. 4 is illustrative of the change in full waist circumference (in cm) from baseline in patients enrolled in the study described in Example 3B after 8 weeks of treatment with salmeterol in combination with fluticasone in human patients in the following treatment groups (with the indicated total weekly dose of salmeterol defined by dose and frequency of injection): (1) 0.5 µg of salmeterol per week; (2) 1.0 µg of salmeterol per week; (3) 5.0 µg of salmeterol per week; (4) 10 µg of salmeterol per week; and (5) 20 µg of salmeterol per week.

It has been determined that of the patients tested in a clinical trial, the greatest therapeutic effectiveness (e.g., as indicated by reduction in adipose tissue and/or reduction in waist or abdomen circumference) was achieved in patients that received the least amount of the lipophilic long-acting beta-2 adrenergic receptor agonist co-administered with a glucocorticosteroid. See FIG. 4. As shown in FIG. 4, of the cohorts tested, it has been determined that the greatest therapeutic efficacy was achieved in patients administered the lowest single session dose of 0.5 μg of salmeterol xinafoate once per week.

Salmeterol

Accordingly, in one aspect, including certain methods of treatment comprising administration of the pharmaceutical formulations described herein, provided are pharmaceutical formulations wherein a lipophilic long-acting selective beta-2 adrenergic receptor agonist, either alone (as single agent therapy) or in combination with one or more additional active ingredients, including glucocorticosteroids (as a combination therapy), is provided in a single session dose that is less than about 20 μg of the lipophilic long-acting selective beta-2 adrenergic receptor agonist, or a salt, optical isomer, racemate, solvate, or polymorph thereof. In some embodiments, the lipophilic, long-acting selective beta-2 agonist is salmeterol, or a salt, optical isomer, racemate, solvate, or polymorph thereof. In further embodiments, the lipophilic, long-acting selective beta-2 agonist is salmeterol xinafoate. In further or additional embodiments, the salmeterol xinafoate is administered in a periodic dose that is once per week, and is administered to a patient in single session dose as provided for herein.

In some embodiments, the single session dose of salmeterol xinafoate is administered once per week in an amount between about 20 μg and about 5 ng, between about 20 μg and about 25 ng, between about 20 μg and about 50 ng, between about 20 μg and about 75 ng, between about 20 μg and about 100 ng, between about 20 μg and about 125 ng, between about 20 μg and about 150 ng, between about between about 20 μg and about 175 ng, between about 20 μg and about 200 ng, between 20 μg and about 225 ng, between about 20 μg and about 250 ng, between about 20 μg and about 275 ng, between about 20 μg and about 300 ng, between about 20 μg and about 325 ng, between about 19 μg and about 350 ng, between about 19 μg and about 375 ng, between about 18 μg and about 400 ng, between about 18 μg and about 425 ng, between about 18 μg and about 450 ng, between about 18 μg and about 475 ng, μg and about 450 ng, between about 18 μg and about 475 ng, between about 18 μg and about 500 ng, between about 17 μg and about 525 ng, between about 17 μg and about 550 ng, between about 17 μg and about 575 ng, between about 17 μg and about 600 ng, between about 17 μg and about 625 ng, between about 17 μg and about 650 ng, between about 16 μg and about 675 ng, between about 15 μg and about 700 ng, between about 14 μg and about 725 ng, between about 13 μg and about 750 ng, between about 13 μg and about 775 ng, between about 13 μg and about 800 ng, between about 12 μg and about 825 ng, between about 11 μg and about 850 ng, between about 10 μg and about 875 ng, between about 9 μg and about 900 ng, between about 8 μg and about 920 ng, between about 7 μg and about 940 ng, between about 6 μg and about 950 ng, between about 5 μg and about 960 ng, between about 4 μg and about 980 ng, or between about 3 μg and about 1 μg.

In still further embodiments, provided are pharmaceutical formulations that are formulated to provide a daily dose of a lipophilic, long-acting selective beta-2 agonist. In some embodiments, a lipophilic, long-acting selective beta-2 agonist to be administered is salmeterol and an adipose tissue-reducing amount of salmeterol to be administered is about 0.001 μg/day to about 1000 μg/day, e.g., about 0.1 μg/day to about 100 μg/day, about 1 μg/day to about 100 μg/day, about 10 μg/day to about 100 μg/day, about 50 μg/day to about 100 μg/day, or any other dose of salmeterol from about 0.001 μg/day to about 1000 μg/day.

Fluticasone

Also provided herein, in further or additional embodiments, including certain methods of treatment comprising administration of the pharmaceutical formulations described herein, are pharmaceutical formulations wherein a glucocorticosteroid, either alone (as single agent therapy) or in combination with one or more additional active ingredients, for example a lipophilic, long-acting selective beta-2 agonist (as a combination therapy), is provided for in a single session dose that is less than about 25 μg of the glucocorticosteroid, or a salt, optical isomer, racemate, solvate, or polymorph thereof. In some embodiments, the glucocorticosteroid is fluticasone, or a salt, optical isomer, racemate, solvate, or polymorph thereof. In further embodiments, the glucocorticosteroid is fluticasone propionate or fluticasone furoate.

In certain embodiments, provided are pharmaceutical formulations that are formulated to provide a single session dose of fluticasone propionate between about 25 μg and about 5 ng. In some embodiments, the pharmaceutical formulations provided herein comprise a single session dose that is an amount of fluticasone that is equal to or less than about 25 μg (including, e.g., about 5 ng, about 50 ng, about 500 ng, about 1 μg, about 10 μg, about 25 μg, or any other amount between about 25 μg and about 5 ng).

In still further embodiments, provided are pharmaceutical formulations that are formulated to provide a daily dose of a glucocorticosteroid. In some embodiments, a glucocorticosteroid to be administered is fluticasone and an adipose tissue-reducing amount of fluticasone to be administered is about 0.001 μg/day to about 1000 μg/day, e.g., about 0.1 μg/day to about 100 μg/day, about 1 μg/day to about 100 μg/day, about 10 μg/day to about 100 μg/day, about 50 μg/day to about 100 μg/day, or any other dose of fluticasone from about 0.001 μg/day to about 1000 μg/day.

In some embodiments, the glucocorticosteroid to be subcutaneously or transcutaneously administered is fluticasone propionate and the therapeutically effective amount of fluticasone propionate is from about 0.05 μg/day to about 500 μg/day, e.g., about 0.05 μg/day to about 400 μg/day, about 0.1 μg/day to about 300 μg/day, about 0.05 μg/day to about 200

μg/day, about 1 μg/day to about 100 μg/day, about 2 μg/day to about 50 μg/day, about 3 μg/day to about 20 μg/day, about 4 μg/day to about 10 μg/day, about 5 μg/day to about 7 μg/day, about 1 μg/day to about 10 μg/day, or about 2 μg/day to about 5 μg/day of fluticasone propionate, or any other dose of fluticasone propionate from about 0.05 μg/day to about 500 μg/day. Other embodiments comprise the use of fluticasone or a salt, optical isomer, racemate, solvate or polymorph thereof, such as, by way of example only, the furoate salt of fluticasone. Still other embodiments comprise the fluticasone furoate subcutaneously or transcutaneously administered from about 0.05 μg/day to about 500 μg/day, e.g., about 0.05 μg/day to about 400 μg/day, about 0.1 μg/day to about 300 μg/day, about 0.05 μg/day to about 200 μg/day, about 1 μg/day to about 100 μg/day, about 2 μg/day to about 50 μg/day, about 3 μg/day to about 20 μg/day, about 4 μg/day to about 10 μg/day, about 5 μg/day to about 7 μg/day, about 1 μg/day to about 10 μg/day, or about 2 μg/day to about 5 μg/day of fluticasone furoate, or any other dose of fluticasone furoate from about 0.05 μg/day to about 500 μg/day.

Salmeterol and Fluticasone

In an embodiment, provided herein is a subcutaneous injectable formulation that comprises a single session dose of salmeterol xinafoate between about 20 μg and about 5 ng, as described herein, including any other amount of salmeterol xinafoate between about 20 μg and about 5 ng and between about 25 μg and about 50 ng of fluticasone propionate as described herein, including any other amount of fluticasone propionate between about 25 μg and about 50 ng.

In still further embodiments, provided are pharmaceutical formulations that are formulated to provide a daily dose of a lipophilic, long-acting selective beta-2 agonist and glucocorticosteroid. In some embodiments, a lipophilic, long-acting selective beta-2 agonist to be administered is salmeterol and an adipose tissue-reducing amount of salmeterol to be administered is about 0.001 μg/day to about 1000 μg/day (including any dose of salmeterol from about 0.001 μg/day to about 1000 μg/day) and an adipose tissue-reducing amount of fluticasone to be administered is about 0.001 μg/day to about 1000 μg/day (including any dose of fluticasone from about 0.001 μg/day to about 1000 μg/day).

Sub-Dosing

In certain situations, the single session dose is administered to the patient in sub-doses (e.g., by subcutaneous injection, transcutaneous application, or otherwise). Accordingly, in another aspect, including certain methods of treatment comprising administration of the pharmaceutical formulations described herein, provided are pharmaceutical formulations wherein a lipophilic long-acting selective beta-2 adrenergic receptor agonist, either alone (as single agent therapy) or in combination with one or more additional active ingredients (as a combination therapy), is provided in at least two sub-doses. In some embodiments, all of the sub-doses are provided to a patient in a single single session during a single week. In further or additional embodiments, including certain methods of treatment comprising administration of the pharmaceutical formulations described herein, provided are pharmaceutical formulations wherein a glucocorticosteroid, either alone (as single agent therapy) or in combination with one or more additional active ingredients (as a combination therapy), is provided in at least two sub-doses whereby all of the sub-doses are provided to a patient in a single session during a single week. In still further embodiments, at least two sub-doses are provided to a patient.

In some embodiments, one or more sub-dose is provided to a patient wherein each sub-dose is a single injection of a fluid comprising a lipophilic long-acting selective beta-2 adrenergic receptor agonist and/or glucocorticosteroid. For example, in some embodiments, provided herein are pharmaceutical formulations and methods of treatment comprising administration of a pharmaceutical formulation wherein a lipophilic long-acting selective beta-2 adrenergic receptor agonist and/or glucocorticosteroid is provided to a patient in about a single sub-dose, at least about two sub-doses, at least about three sub-doses, at least about four sub-doses, at least about five sub-doses, at least about six sub-doses, at least about seven sub-doses, at least about eight sub-doses, at least about nine sub-doses, at least about 10 sub-doses, at least about 11 sub-doses, at least about 12 sub-doses, at least about 13 sub-doses, at least about 14 sub-doses, at least about 15 sub-doses, at least about 16 sub-doses, at least about 17 sub-doses, at least about 18 sub-doses, at least about 19 sub-doses, at least about 20 sub-doses, at least about 21 sub-doses, at least about 22 sub-doses, at least about 23 sub-doses, at least about 24 sub-doses, at least about 25 sub-doses, at least about 26 sub-doses, at least about 27 sub-doses, at least about 28 sub-doses, at least about 29 sub-doses, at least about 30 sub-doses, at least about 31 sub-doses, at least about 32 sub-doses, at least about 33 sub-doses, at least about 34 sub-doses, at least about 35 sub-doses, or more than about 35 sub-doses.

In some embodiments, each sub-dose is administered to a patient in an equal amount. For example, in some situations where the single session dose is about 20 μg of salmeterol xinafoate that is delivered to the patient in 22 sub-doses, each sub-dose contains about 1 μg of salmeterol xinafoate. In other situations, the single session dose is about 500 ng and is delivered to the patient in 22 sub-doses and each sub-dose contains about 22 or 23 ng of salmeterol xinafoate. Still in further situations, a prescribing physician may administer, or the patient may self-administer, sub-doses in amounts that are not equal but vary in amount with respect to each sub-dose that is administered.

In some embodiments, at least two sub-doses of salmeterol xinafoate or fluticasone propionate, as described herein, are administered to a patient in a single session dose via subcutaneous injection to the abdominal region of the patient. In some of these embodiments, each sub-dose is applied to a patient about 2-6 cm away from a closest second sub-dose. In further embodiments, each sub-dose is applied to a patient about 4 cm away from a closest second sub-dose. See, e.g., Example 3C.

In some embodiments, a sub-dose is administered, for example by subcutaneous or transcutaneous injection, to areas of non-visceral fat deposits on a subject, including for example subcutaneous fat. In some embodiments for which the formulations described herein are useful include, but are not limited to, the inside region of the knees, the middle to upper area of the upper arm, including the tricep area, the submental area, including the area under the chin, for example the wattle (which is understood to refer to the fleshy fold of skin in the submental area of a patient), the abdomen, the hips, the inner thigh, the outer thigh, the buttocks, the lower back, upper back and the chest.

Salmeterol

In certain embodiments, provided are pharmaceutical formulations and methods of treatment comprising the pharmaceutical formulations that are formulated to provide a sub-dose of salmeterol xinafoate between about 20 μg and about 1 ng, between about 20 μg and about 2 ng, between about 20

µg and about 3 ng, between about 20 µg and about 4 ng, between about 20 µg and about 5 ng between about 20 µg and about 6 ng, between about 20 µg and about 7 ng, between about 15 µg and about 8 ng, between about 10 µg and about 9 ng, between about 5 µg and about 10 ng, between about 1 µg and about 12 ng, between about 900 ng and about 14 ng, between about 800 ng and about 16 ng, between about 700 ng and about 18 ng, between about 600 ng and about 20 ng, between about 550 ng and about 22 ng, between about 500 ng and about 24 ng, between about 450 ng and about 26 ng, between about 400 ng and about 28 ng, between about 350 ng and about 30 ng, between about 300 ng and about 32 ng, between about 250 ng and about 34 ng, between about 200 ng and about 36 ng, between about 150 ng and about 38 ng, between about 125 ng and about 40 ng, between about 100 ng and about 42 ng, between about 90 ng and about 44 ng, between about 80 ng and about 46 ng, between about 75 ng and about 48 ng, between about 70 ng and about 50 ng, between about 69 ng and about 51 ng, between about 68 ng and about 52 ng, between about 67 ng and about 53 ng, between about 66 ng and about 54 ng, between about 65 ng and about 55 ng, between about 64 ng and about 56 ng, between about 63 ng and about 57 ng, between about 62 ng and about 58 ng, between about 61 ng and about 59 ng, or about 60 ng.

In some embodiments, provided herein are pharmaceutical formulations, and methods of treatment comprising administration of the pharmaceutical formulations, that are formulated to provide a sub-dose of salmeterol xinafoate that is equal to or less than about 20 µg, equal to or less than about 19 µg, equal to or less than about 18 µg, equal to or less than about 17 µg, equal to or less than about 16 µg, equal to or less than about 15 µg, equal to or less than about 14 µg, equal to or less than about 13 µg, equal to or less than about 12 µg, equal to or less than about 11 µg, equal to or less than about 10 µg, equal to or less than about 9 µg, equal to or less than about 8 µg, equal to or less than about 7 µg, equal to or less than about 6 µg, equal to or less than about 5 µg, equal to or less than about 4 µg, equal to or less than about 3 µg, equal to or less than about 2 µg, equal to or less than about 1 µg, equal to or less than about 975 ng, equal to or less than about 950 ng, equal to or less than about 925 ng, equal to or less than about 900 ng, equal to or less than about 875 ng, equal to or less than about 850 ng, equal to or less than about 825 ng, equal to or less than about 800 ng, equal to or less than about 775 ng, equal to or less than about 750 ng, equal to or less than about 725 ng, equal to or less than about 700 ng, equal to or less than about 675 ng, equal to or less than about 650 ng, equal to or less than about 625 ng, equal to or less than about 600 ng, equal to or less than about 575 ng, equal to or less than about 550 ng, equal to or less than about 525 ng, equal to or less than about 500 ng, equal to or less than about 475 ng, equal to or less than about 450 ng, equal to or less than about 425 ng, equal to or less than about 400 ng, equal to or less than about 375 ng, equal to or less than about 350 ng, equal to or less than about 325 ng, equal to or less than about 300 ng, equal to or less than about 275 ng equal to or less than about 250 ng, equal to or less than about 225 ng, equal to or less than about 200 ng, equal to or less than about 175 ng, equal to or less than about 150 ng, equal to or less than about 125 ng, equal to or less than about 100 ng, equal to or less than about 75 ng, or equal to or less than about 50 ng, or equal to or less than about 25 ng, equal to or less than about 20 ng, equal to or less than about 15 ng, equal to or less than about 10 ng, equal to or less than about 5 ng, or equal to or less than about 1 ng.

Suitable tissue concentration of salmeterol via subcutaneous administration for adipose tissue treatment include from about 1 pM to about 100 µM, e.g., about 0.01 µM to about 50 µM, 0.5 µM to about 50 µM, about 2.0 µM to about 50 µM, about 5 µM to about 50 µM, about 10 µM to about 50 µM, about 20 µM to about 75 µM, or any other tissue concentration of salmeterol from about 0.1 nM to about 100 µM.

Fluticasone

Also provided herein, in further or additional embodiments, including certain methods of treatment comprising administration of the pharmaceutical formulations described herein, are pharmaceutical formulations wherein a glucocorticosteroid, either alone (as single agent therapy) or in combination with one or more additional active ingredients, for example a lipophilic, long-acting selective beta-2 agonist (as a combination therapy), is formulated to be administered to a patient in a sub-dose that is between about 25 µg and about 5 ng. In some embodiments, the glucocorticosteroid is fluticasone, or a salt, optical isomer, racemate, solvate, or polymorph thereof. In further embodiments, the glucocorticosteroid is fluticasone propionate or fluticasone furoate.

In certain embodiments, provided are pharmaceutical formulations that are formulated to provide a sub-dose of fluticasone propionate that is equal to or less than about 25 µg (including, e.g., about 5 ng, about 50 ng, about 500 ng, about 1 µg, about 10 µg, about 25 µg, or any other amount between about 25 µg and about 5 ng).

Appropriate tissue concentrations of glucocorticosteroids used for the therapeutic methods described herein range from about 0.001 µM to about 5 µM, e.g., from about 1.0 µM to about 5 µM, from about 0.1 µM to about 2 µM, from about 0.1 µM to about 1 mM, from about 0.01 µM to about 0.1 µM or any other tissue concentration of the glucocorticosteroid from about 0.001 µM to about 5 µM.

Salmeterol and Fluticasone

In a specific embodiment, provided herein is a subcutaneous injectable formulation that comprises a sub-dose of salmeterol xinafoate between about 20 µg and about 1 ng, as described herein, including any other amount of salmeterol xinafoate between about 20 µg and about 1 ng and between about 25 µg and about 5 ng of fluticasone propionate as described herein, including any other amount of fluticasone propionate between about 25 µg and about 5 ng.

In one embodiment, a subcutaneous injectable formulation, or a transcutaneous formulation, that is formulated to be administered to a patient as a single session dose or a sub-dose that comprises from about 20 µg to about 1 ng of salmeterol xinafoate (e.g., about 1 ng, about 50 ng, about 250 ng, about 500 ng, about 750 ng, about 1 µg, about 5 µg, about 10 µg, about 15 µg, or about 20 µg, or any other amount of salmeterol xinafoate from about 20 µg to about 1 ng) and from about 300 µg to about 5 ng of fluticasone propionate (e.g., about 5 ng, about 500 ng, about 1 µg, about 5 µg, about 10 µg, about 15 µg, about 20 µg, about 25 µg, about 30 µg, about 35 µg, about 40 µg, about 45 µg, about 50 µg, about 60 µg, about 70 µg, about 80 µg, about 90 µg, about 100 µg, or any other amount of fluticasone propionate from about 300 µg to about 5 ng) formulated in a volume of up to about 10 mL (e.g., about 0.1 mL, about 0.3 mL, about 0.5 mL, about 0.7 mL, about 1.0 mL, about 1.1 mL, about 1.5 mL, about 2 mL, about 2.5 mL, about 3 mL, about 3.5 mL, about 4 mL, about 5 mL, about 6 mL, about 7 mL, about 8 mL, about 9 mL, or any other volume from about 0.1 mL to about 10 mL) of an excipient compatible with subcutaneous administration. In some embodiments, the excipient concentration is kept below 1% (e.g., about 0.05%, about 0.2%, about 0.3%, about 0.4%, about 0.5%, about 0.6%, about 0.8%, or any other concentration from about 0.05% to less than about 1%.

Pharmacokinetic Parameters

In another aspect is a pharmaceutical formulation, including certain methods of treatment comprising administration of the pharmaceutical formulations described herein, comprising an adipose tissue-reducing amount of salmeterol or a salt, optical isomer, racemate, solvate, or polymorph thereof and at least one subcutaneously acceptable inactive ingredient, wherein the formulation provides a mean plasma salmeterol $C_{max}$ equal to or less than about 300 pg/mL when administered subcutaneously. In one embodiment, the formulation provides a mean plasma salmeterol $C_{max}$ equal to or less than about 270 pg/mL. In one embodiment, the formulation provides a mean plasma salmeterol $C_{max}$ equal to or less than about 250, about 230, about 200, about 190, about 180, about 170, about 160, about 150, about 140, about 130, about 120, about 110, about 100, about 90, about 80, about 70, about 60, about 50, about 40, about 30, about 20, about 10, about 3, about 1 pg/mL, or is undetectable using conventional methodology. For purposes of this application, "undetectable using conventional methodology" or "undetectable using current methodology," means that the concentration is lower than the low limit of quantitation (LLOQ) using the Liquid Chromatography/Mass Spectrometry/Mass Spectrometry (LC/MS/MS) method, which is understood in the art to be a type of tandem mass spectrometry for determining $C_{max}$ levels.

In one embodiment, the pharmaceutical formulation further comprises a glucocorticosteroid or a salt, optical isomer, racemate, solvate, or polymorph thereof. In another embodiment, the glucocorticosteroid is fluticasone or a pharmaceutically acceptable salt, optical isomer, racemate, solvate, or polymorph thereof. In a further embodiment, the glucocorticosteroid is fluticasone propionate. In yet another embodiment, the glucocorticosteroid is fluticasone furoate. In one embodiment, the formulation provides a mean plasma fluticasone $C_{max}$ of about 1 to about 200 pg/mL. In a further embodiment, the formulation provides a mean plasma fluticasone propionate $C_{max}$ of about 1 to about 200 pg/mL. In yet a further embodiment, the mean plasma fluticasone propionate $C_{max}$ is about 100, about 90, about 80, about 70, about 60, about 50, about 40, about 30, about 20, about 10, about 3 pg/mL, about 1 pg/mL, or is undetectable using conventional methodology. In a further embodiment, the mean plasma fluticasone propionate $C_{max}$ is about 50 pg/mL. In another embodiment, the mean plasma fluticasone propionate $C_{max}$ results from subcutaneous administration. In another embodiment, salmeterol and fluticasone propionate are co-administered together in a formulation suitable for subcutaneous administration. In a further embodiment, salmeterol and fluticasone propionate are administered separately in formulations suitable for subcutaneous administration.

Partitioning into Adipose Tissue

In a further aspect is a pharmaceutical formulation comprising an adipose tissue-reducing amount of salmeterol or a salt, optical isomer, racemate, solvate, or polymorph thereof and at least one subcutaneously acceptable inactive ingredient, wherein the formulation provides a salmeterol plasma $C_{max}$ ratio of subcutaneous to intravenous administration of between about 0.01 to about 0.4 when administered subcutaneously (also known as the "salmeterol partition" ratio.) For purposes of this application, the ratio of plasma $C_{max}$ of a long-acting beta-2 adrenergic receptor agonist administered subcutaneously to the plasma $C_{max}$ of the same long-acting beta-2 adrenergic receptor agonist administered intravenously is known as the "partition" ratio. Thus, in one embodiment, the partition ratio of salmeterol is about 0.01 to about 0.4. In another embodiment, the salmeterol partition ratio is about 0.05 to about 0.3. In another embodiment, the salmeterol partition ratio is from about 0.1 to about 0.35. In a further embodiment, the salmeterol partition ratio is about 0.1. In another embodiment, the salmeterol partition ratio is between 0.05 to about 0.2. In a further embodiment, the salmeterol partition ratio is between about 0.1 to about 0.2. In yet another embodiment, the salmeterol partition ratio is about 0.01, about 0.02, about 0.03, about 0.04, about 0.05, about 0.06, about 0.07, about 0.08, about 0.09, about 0.1, about 0.11, about 0.12, about 0.13, about 0.14, about 0.015, about 0.16, about 0.17, about 0.18, about 0.19, about 0.2, about 0.21, about 0.22, about 0.23, about 0.24, about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, about 0.40. By way of a non-limiting example only, salmeterol xinafoate formulated in 5% PEG-400 in 0.9% saline USP, at various concentrations were administered to non-naive Gottingen minipigs via single intravenous injection or subcutaneous injection (see Example 1.) The salmeterol partition ratio was calculated as the average salmeterol plasma $C_{max}$ of subcutaneous administration ((403+575)/2) divided by the average salmeterol plasma $C_{max}$ of intravenous administration ((4950+4290)/2). Thus, in this non-limiting example, the salmeterol partition ratio was determined to be 0.1. In a further embodiment, is a subcutaneous formulation comprising of salmeterol or a salmeterol-like compound and a subcutaneously acceptable excipient wherein the formulation provides a partition ratio of between about 0.01 and about 0.4. As used herein, a salmeterol-like compound is a compound having a partition ratio of between about 0.01 and 0.4 and provides limited systemic exposure, and consequently, a reduced or minimized risk of producing cardiovascular side effects. Additionally, salmeterol-like compounds also selectively partition into the adipose tissue due to their lipophilic nature. In another embodiment, is a pharmaceutical formulation providing a salmeterol partition ratio of between about 0.01 to about 0.2 and further comprising a glucocorticosteroid or a salt or solvate thereof. In yet another embodiment, the glucocorticosteroid is fluticasone propionate. In one embodiment, the formulation provides a salmeterol partition ratio of between about 0.01 to about 0.3 and a mean plasma fluticasone propionate $C_{max}$ of about 1 to about 200 pg/mL. In yet a further embodiment, the formulation provides a salmeterol partition ratio of between about 0.01, about 0.02, about 0.03, about 0.04, about 0.05, about 0.06, about 0.07, about 0.08, about 0.09, about 0.1, about 0.11, about 0.12, about 0.13, about 0.14, about 0.015, about 0.16, about 0.17, about 0.18, about 0.19, about 0.2 and a mean plasma fluticasone propionate $C_{max}$ of about 190, about 180, about 170, about 160, about 150, about 130, about 120, about 110, about 100, about 90, about 80, about 70, about 60, about 50, about 40, about 30, about 20, about 10, about 1 pg/mL.

In another embodiment, the mean plasma fluticasone propionate $C_{max}$ results from subcutaneous administration. In a further embodiment, salmeterol and fluticasone propionate are co-administered together in a formulation suitable for subcutaneous administration such that the formulation provides a salmeterol plasma $C_{max}$ ratio of subcutaneous to intravenous administration of between about 0.01 to about 0.2 and a mean plasma fluticasone propionate $C_{max}$ of about 1 to about 200 pg/mL. In a further embodiment, salmeterol and fluticasone propionate are administered separately in formulations suitable for subcutaneous administration such that the formulations provide a salmeterol plasma $C_{max}$ ratio of subcutaneous to intravenous administration of between about 0.01 to about 0.2 and a mean plasma fluticasone propionate $C_{max}$ of about 1 to about 200 pg/mL. In other embodiments, fluticasone furoate is used as a glucocorticosteroid such that the formulation provides a salmeterol plasma $C_{max}$ ratio of subcutaneous to intravenous administration of between about 0.01 to about 0.2 and a mean plasma fluticasone furoate $C_{max}$ of about 1 to about 200 pg/mL.

In further embodiments, the pharmaceutical formulations provided herein that provide a salmeterol plasma $C_{max}$ ratio of subcutaneous to intravenous administration of between about 0.01 to about 0.4 when subcutaneously administered to a patient further provide a reduction in the circumference of the patient's waist or abdomen. In some embodiments, provided herein is a formulation that is formulated to provide a single session dose of salmeterol xinafoate in an amount that is about 5 ng to about 20 μg and that provides a salmeterol plasma $C_{max}$ ratio of subcutaneous to intravenous administration of between about 0.01 to about 0.4 when administered subcutaneously. In further or additional embodiments, provided herein is a pharmaceutical formulation comprising a single session dose of fluticasone propionate in an amount that is between about 1 μg and about 300 μg. In some embodiments, provided herein are pharmaceutical formulations comprising a weekly dose of salmeterol xinafoate that is between about 5 ng to about 150 μg. In further or additional embodiments, provided herein is a pharmaceutical formulation comprising a weekly dose of fluticasone propionate in an amount that is between about 50 ng and about 100 μg. In still further embodiments, provided herein is a pharmaceutical formulation comprising a sub-dose of salmeterol xinafoate in an amount that is between about 1 ng to about 50 μg. In other embodiments, provided herein is a pharmaceutical formulation comprising a sub-dose of fluticasone propionate in an amount that is between about 5 ng to about 20 μg.

In a further aspect is a subcutaneous formulation consisting essentially of a long-acting beta-2 receptor agonist and a subcutaneously acceptable excipient thereof, wherein the formulation provides a partition ratio lower than the partition ratio of a reference long-acting beta-2 receptor agonist. In one embodiment, the subcutaneous formulation provides a partition ratio of about four to six times lower than the partition ratio of a reference long-acting beta-2 receptor agonist. In one embodiment, the formulation described herein provides a partition ratio about five times lower than the partition ratio of a reference long-acting beta-2 receptor agonist. In another embodiment, the reference long-acting beta-2 receptor agonist has low lipophilicity. In yet another embodiment, the reference long-acting beta-2 receptor agonist is formoterol. By way a non-limiting example only, formoterol fumarate dehydrate and budesonide were formulated in about 2% PEG-400 in saline and administered via single intravenous injection or subcutaneous injection to non-naive Gottingen minipigs (see Example 2). The partition ratio was calculated as described above. Thus, in this non-limiting example, the salmeterol formulation has a partition ratio about five times lower than the partition ratio of formoterol (0.1 compared to 0.5). In another embodiment, the subcutaneous formulation further comprises a glucocorticosteroid or a salt or solvate thereof. In yet another embodiment, the glucocorticosteroid is fluticasone propionate. In a further embodiments, the glucocorticosteroid is fluticasone furoate. In yet a further embodiment, the salmeterol formulation provides a partition ratio about five times lower than a reference long-acting beta-2 receptor agonist, wherein the reference long-acting beta-2 adrenergic receptor agonist is formoterol, and a mean plasma fluticasone propionate $C_{max}$ of about 1 to about 200 pg/mL. In another embodiment, the mean plasma fluticasone propionate $C_{max}$ results from subcutaneous administration. In yet another embodiment, salmeterol and fluticasone propionate are co-administered together in a formulation suitable for subcutaneous administration such that the formulation provides a partition ratio of about five times lower than the partition ratio of formoterol and a mean plasma fluticasone propionate $C_{max}$ of about 1 to about 200 pg/mL. In some embodiments, the fluticasone propionate described in the formulations herein is substituted with fluticasone furoate such that, and by way of example only, the formulation provides a partition ratio about five times lower than the partition ratio of formoterol and/or a mean plasma fluticasone furoate $C_{max}$ of about 1 to about 200 pg/mL.

Methods of Reducing Adipose Tissue

In another aspect, provided herein are methods for reducing adipose tissue in a patient comprising administering to the patient a pharmaceutical formulation comprising a lipophilic long-acting selective beta-2 adrenergic receptor agonist, either alone (as single agent therapy) or in combination with one or more additional active ingredients, for example a glucocorticosteroid (as a combination therapy) and at least one subcutaneously acceptable inactive ingredient. In one aspect is a method for reducing adipose tissue in a subject comprising subcutaneously administering to the subject a pharmaceutical formulation comprising an active agent consisting essentially of an adipose tissue-reducing amount of a lipophilic long-acting selective beta-2 adrenergic receptor agonist or a salt, optical isomer, racemate, solvate, or polymorph thereof and at least one subcutaneously acceptable inactive ingredient wherein adipose tissue in the subject is reduced. In one embodiment, the lipophilic long-acting selective beta-2 adrenergic receptor agonist is salmeterol. In yet another embodiment, the salt of the lipophilic long-acting selective beta-2 adrenergic agonist is a xinafoate salt. In a further embodiment, provided is a method for reducing adipose tissue in a subject wherein the pharmaceutical formulation further comprises a glucocorticosteroid or a salt or solvate thereof. In another embodiment, the glucocorticosteroid is fluticasone or a salt or solvate thereof. In another embodiment, the salt is a propionate or furoate salt. In further embodiments, the salt is a furoate salt. In yet a further embodiment, the glucocorticosteroid is fluticasone propionate. In another embodiment, is a method for reducing adipose tissue in a subject wherein the pharmaceutical formulation provides a mean plasma fluticasone propionate $C_{max}$ between about 100 pg/mL and a level that is undetectable using current methodology. In a further embodiment, the subcutaneous administration results in a reduced or minimized risk of producing cardiovascular side effects.

In further embodiments, the pharmaceutical formulations provided herein that reduce adipose tissue when subcutaneously administered to a patient further provides a reduction in the circumference of the patient's waist or abdomen. In specific embodiments, the patient experiences a change in body weight that is less than about 5%, less than about 3%, less than about 2%, less than about 1%, or less than about 0.5% during a treatment period. In some embodiments, provided herein is a formulation that is formulated to provide a single session dose of salmeterol xinafoate in an amount that is about 5 ng to about 20 μg to a subject wherein adipose tissue in the subject is reduced. In further or additional embodiments, provided herein is a pharmaceutical formulation comprising a single session dose of fluticasone propionate in an amount that is between about 1 μg and about 300 μg. In some embodiments, provided herein are pharmaceutical formulations comprising a weekly dose of salmeterol xinafoate that is between about 5 ng to about 150 µg. In further or additional embodiments, provided herein is a pharmaceutical formulation comprising a weekly dose of fluticasone propionate in an amount that is between about 50 ng and about 100 µg. In still further embodiments, provided herein is a pharmaceutical formulation comprising a sub-dose of salmeterol xinafoate in an amount that is between about 1 ng to about 50 µg. In other embodiments, provided herein is a pharmaceutical formulation comprising a sub-dose of fluticasone propionate in an amount that is between about 5 ng to about 20 µg.

In yet a further embodiment, the subcutaneous administration results in a reduced or minimized risk of producing an increase in heart rate or a decrease in blood pressure or a combination thereof. In another embodiment, the subcutaneous administration provides a minimized risk of producing anaphylaxis related effects, such as, flushing, reddening, rapid heart rate, chest tightness, difficulty breathing, faintness, heart palpitations, hives, atrophy, pigmentation, nodularity, necrosis, irregular or abnormal heart rate, paroxysmal bronchoconstriction, and hypersensitivity reaction such as angioedema and urticaria. By way of a non-limiting example only, a subcutaneous formulation comprising salmeterol was administered to Gottingen minipigs. The salmeterol partition ratio is determined as described above. Thus, in this non-limiting example, the subcutaneous formulation administered to minipigs provides a salmeterol partition ratio of 0.1 and a reduced or minimized risk of producing cardiovascular side effects. It should be noted that the reduced or minimized risk described herein (due to limited systemic exposure) refers to a generalized population and may vary depending on the individual subject or patient. Subcutaneous formulations consisting essentially of salmeterol and fluticasone provide therapeutic effect to a regional fat deposit and a reduced or minimized risk of producing the side effects associated with the use of other long-acting beta-2 agonists or long-acting beta-2 agonists administered by other methods. Such side effects include paradoxical bronchospasm, high blood pressure, abnormal heart rhythm, abnormally low blood pressure, an increase in asthma related conditions, bronchospasm, inflammation of the lining of the stomach and intestines, involuntary quivering, fast heartbeat, chest pain, and giant hives.

Methods of Treating Regional Fat Accumulation

In yet another aspect, provided herein are methods for treating regional fat accumulation in a patient comprising administering to the patient a pharmaceutical formulation comprising a lipophilic long-acting selective beta-2 adrenergic receptor agonist, either alone (as single agent therapy) or in combination with one or more additional active ingredients, for example a glucocorticosteroid (as a combination therapy) and at least one subcutaneously acceptable inactive ingredient. In further embodiments, the method for treating regional fat accumulation in a subject comprises subcutaneously administering to a regional fat accumulation area a pharmaceutical formulation comprising a regional fat accumulation reducing amount of salmeterol or a salt, optical isomer, racemate, solvate, or polymorph thereof and at least one subcutaneously acceptable inactive ingredient. In further or additional embodiments, the formulation provides a mean plasma salmeterol $C_{max}$ equal that is in the range of about 300 pg/mL to levels that are undetectable using conventional methodology, wherein the regional fat accumulation in the subject is reduced. In one embodiment, salmeterol selectively partitions into adipose tissue of the regional fat accumulation relative to plasma.

In one embodiment, provided is a method for treating regional fat accumulation in a subject comprising administration of the pharmaceutical formulations provided herein that when subcutaneously administered to a patient, provides a reduction in the circumference of the patient's waist or abdomen. In further or additional embodiments, the patient experiences a change in body weight that is less than about 5%, less than about 3%, less than about 2%, less than about 1%, or less than about 0.5% during a treatment period. In yet another embodiment, provided is a method for treating regional fat accumulation in a subject comprising subcutaneously administering to a regional fat accumulation area, a pharmaceutical formulation comprising a regional fat accumulation reducing amount of salmeterol or a salt, optical isomer, solvate, or polymorph thereof and at least one subcutaneously acceptable inactive ingredient, wherein the formulation provides a mean plasma salmeterol $C_{max}$ equal that is in the range of about 300 pg/mL to levels that are undetectable using conventional methodology. In further or additional embodiments, the pharmaceutical formulation further comprises a glucocorticosteroid or a salt, optical isomer, racemate, solvate, or polymorph thereof wherein the regional fat accumulation in the subject is reduced. In one embodiment, the glucocorticosteroid is fluticasone or a salt or solvate thereof. In another embodiment, the glucocorticosteroid is fluticasone propionate. In a further embodiment the glucocorticosteroid is fluticasone furoate.

In further embodiments, the method for treating regional fat accumulation in a subject comprises subcutaneously administering to a regional fat accumulation area a pharmaceutical formulation comprising a regional fat accumulation reducing amount of salmeterol or a salt, optical isomer, racemate, solvate, or polymorph thereof and at least one subcutaneously acceptable inactive ingredient wherein the regional fat accumulation reducing amount is a single session dose of salmeterol xinafoate in an amount that is about 5 ng to about 20 µg. In further or additional embodiments, provided herein is a pharmaceutical formulation comprising a single session dose of fluticasone propionate in an amount that is between about 1 µg and about 300 µg. In some embodiments, provided herein are pharmaceutical formulations comprising a weekly dose of salmeterol xinafoate that is between about 5 ng to about 150 µg. In further or additional embodiments, provided herein is a pharmaceutical formulation comprising a weekly dose of fluticasone propionate in an amount that is between about 50 ng and about 100 µg. In still further embodiments, provided herein is a pharmaceutical formulation comprising a sub-dose of salmeterol xinafoate in an amount that is between about 1 ng to about 50 µg. In other embodiments, provided herein is a pharmaceutical formulation comprising a sub-dose of fluticasone propionate in an amount that is between about 5 ng to about 20 µg.

In yet another embodiment, provided is a method for treating regional fat accumulation in a subject comprising subcutaneously administering to a regional fat accumulation area a pharmaceutical formulation comprising a regional fat accumulation reducing amount of salmeterol or a salt, optical isomer, racemate, solvate, or polymorph thereof and further comprising fluticasone propionate, wherein the formulation provides a mean plasma salmeterol $C_{max}$ equal to or less than about 300 pg/mL (including $C_{max}$ levels that are undetectable using conventional methodology) and a mean plasma fluticasone propionate $C_{max}$ of about 1 to about 100 pg/mL (including $C_{max}$ levels that are undetectable using conventional methodology). In one embodiment, provided is a method for treating regional fat accumulation comprising subcutaneously administering to a regional fat accumulation area a pharmaceutical formulation comprising a regional fat accumulation reducing amount of salmeterol or a salt, optical isomer, racemate, solvate, or polymorph thereof and fluticasone propionate or a salt or solvate thereof wherein the formulation provides a mean plasma fluticasone propionate $C_{max}$ equal to or less than about 100, about 90, about 80, about 70, about 60, about 50, about 40, about 30, about 20, about 10, about 1 pg/mL, or is undetectable using conventional methodology. In other embodiments, provided are methods for treating regional fat accumulation comprising subcutaneously administering to a regional fat accumulation area a pharmaceutical formulation comprising a regional fat accumulation reducing amount of salmeterol or a salt, optical isomer, racemate, solvate, or polymorph thereof and fluticasone or a salt or solvate thereof wherein the formulation provides a mean plasma fluticasone $C_{max}$ equal to or less than about 100, about 90, about 80, about 70, about 60, about 50, about 40, about 30, about 20, about 10, about 1 pg/mL, or is undetectable using conventional methodology. In further embodiments, the fluticasone salt is a furoate salt. In further embodiments, the pharmaceutical formulations provided herein, when subcutaneously administered to a patient, provide a reduction in the circumference of the patient's waist. In specific embodiments, the patient experiences a change in body weight that is less than about 5%, less than about 3%, less than about 2%, less than about 1%, or less than about 0.5% during a treatment period.

Also described herein is a method for treating regional fat accumulation comprising subcutaneously administering to the subject a pharmaceutical formulation comprising an active agent consisting essentially of a regional fat accumulation reducing amount of a long-acting selective beta-2 adrenergic receptor agonist or a salt, optical isomer, racemate, solvate, or polymorph thereof and at least one subcutaneously acceptable inactive ingredient. In one embodiment, the lipophilic long-acting selective beta-2 adrenergic receptor agonist is salmeterol. In another embodiment, the salt of the lipophilic long-acting selective beta-2 adrenergic agonist is a xinafoate salt. In a further embodiment, the subcutaneous administration reduces or minimizes the risk of producing cardiovascular side effects (by minimizing systemic exposure). In yet a further embodiment, the subcutaneous administration reduces or minimizes the risk of producing an increase in heart rate or a decrease in blood pressure or a combination thereof. In another embodiment, the risks that are reduced or minimized as a result of subcutaneous administration include effects, such as, flushing, reddening, rapid heart rate, chest tightness, difficulty breathing, faintness, heart palpitations, hives, irregular or abnormal heart rate, paroxysmal bronchoconstriction, and hypersensitivity reaction such as angioedema and urticaria.

In yet another embodiment, provided is a method for treating regional fat accumulation comprising subcutaneously administering to the subject a pharmaceutical formulation comprising an adipose tissue-reducing amount of a lipophilic long-acting selective beta-2 adrenergic receptor agonist or a salt, optical isomer, racemate, solvate, or polymorph thereof and at least one subcutaneously acceptable inactive ingredient wherein the formulation provides a mean plasma lipophilic, long-acting selective beta-2 adrenergic receptor agonist $C_{max}$ equal to or less than about 300 pg/mL (including $C_{max}$ levels that are undetectable using conventional methodology). In another embodiment, the lipophilic, long-acting selective beta-2 adrenergic receptor agonist is not formoterol. In one embodiment, the lipophilic long-acting selective beta-2 adrenergic receptor agonist is salmeterol. In yet another embodiment, the salt of salmeterol is a xinafoate salt. In yet another embodiment, is a method for treating regional fat accumulation comprising subcutaneously administering to the subject a pharmaceutical formulation comprising an active agent consisting essentially of a regional fat accumulation reducing amount of a lipophilic long-acting selective beta-2 adrenergic receptor agonist or a salt, optical isomer, racemate, solvate, or polymorph thereof and at least one subcutaneously acceptable inactive ingredient wherein the formulation provides a mean plasma lipophilic, long-acting selective beta-2 adrenergic receptor agonist $C_{max}$ equal to or less than about 300 pg/mL (including $C_{max}$ levels that are undetectable using conventional methodology) and wherein the pharmaceutical formulation further comprises a glucocorticosteroid or a salt or solvate thereof. In one embodiment, the glucocorticosteroid is fluticasone propionate. In yet another embodiment, provided is a method for treating regional fat accumulation comprising subcutaneously administering to the subject a pharmaceutical formulation comprising a regional fat accumulation reducing amount of a lipophilic long-acting selective beta-2 adrenergic receptor agonist or a salt, optical isomer, racemate, solvate, or polymorph thereof and at least one pharmaceutically acceptable inactive ingredient and further comprising fluticasone propionate, wherein the pharmaceutical formulation provides a plasma lipophilic, long-acting selective beta-2 adrenergic receptor agonist $C_{max}$ equal to or less than about 300 pg/mL (including $C_{max}$ levels that are undetectable using conventional methodology) and a mean plasma fluticasone propionate $C_{max}$ equal to or less than about 100 pg/mL (including $C_{max}$ levels that are undetectable using conventional methodology). In one embodiment, is a method for treating regional fat accumulation comprising subcutaneously administering to the subject a pharmaceutical formulation comprising a lipophilic, long-acting selective beta-2 adrenergic receptor agonist or a salt, optical isomer, racemate, solvate, or polymorph thereof and fluticasone propionate wherein the formulation provides a mean plasma fluticasone propionate $C_{max}$ equal to or less than about 100, about 90, about 80, about 70, about 60, about 50, about 40, about 30, about 20, about 10, about 1 pg/mL, or is undetectable using conventional methodology. In one embodiment, the mean plasma fluticasone propionate $C_{max}$ results from systemic administration. In another embodiment, the mean plasma fluticasone propionate $C_{max}$ results from subcutaneous administration. In other embodiments, the formulation comprises a fluticasone salt, such as by way of example only, fluticasone furoate, such that the mean plasma fluticasone furoate $C_{max}$ results from systemic administration. In another embodiment, the mean plasma fluticasone furoate $C_{max}$ results from subcutaneous administration. In yet other embodiments, the mean plasma fluticasone results from fluticasone furoate.

Methods of Inducing Lipolysis in Adipose Tissue

As discussed herein, lipolysis and/or inhibition of adipogenesis are stimulated by the beta-1, 2, or 3 receptor subtypes. Thus, agonists to one, two and/or all three receptors are capable of stimulating lipolysis and/or inhibition of adipogenesis. In humans, beta-2 receptor activity is believed to be more important for stimulating lipolysis, particularly in the presence of a glucocorticosteroid. Lipolytic activity and adipocyte proliferation inhibition are believed to be mediated through modulation of adrenergic receptors in adipose tissue and/or on adipocytes.

In another aspect, provided herein is a method for inducing lipolysis in adipose tissue comprising subcutaneously administering a pharmaceutical formulation suitable for subcutaneous injection comprising: (a) a lipophilic long-acting selective beta-2 adrenergic receptor agonist or glucocorticosteroid, or a salt, optical isomer, racemate, solvate, or polymorph thereof and (b) at least one subcutaneously acceptable inactive ingredient. In one aspect is a method for inducing lipolysis in a subject comprising subcutaneously administering to the subject a pharmaceutical formulation comprising an active agent consisting essentially of an adipose tissue-reducing amount of a lipophilic long-acting selective beta-2 adrenergic receptor agonist or a salt, optical isomer, racemate, solvate, or polymorph thereof and at least one subcutaneously acceptable inactive ingredient that induced lipolysis in a patient, and reduces adipose tissue in the area treated. In one embodiment, the lipophilic long-acting selective beta-2 adrenergic receptor agonist is salmeterol. In yet another embodiment, the salt of the lipophilic long-acting selective beta-2 adrenergic agonist is a xinafoate salt. In a further embodiment, provided is a method for inducing lipolysis in a subject wherein the pharmaceutical formulation further comprises a glucocorticosteroid or a salt or solvate thereof In another embodiment, the glucocorticosteroid is fluticasone or a salt or solvate thereof In another embodiment, the salt is a propionate or furoate salt. In further embodiments, the pharmaceutical formulations provided herein, when subcutaneously administered to a patient, provide a reduction in the circumference of the patient's waist.

In further embodiments, the salt is a furoate salt. In yet a further embodiment, the glucocorticosteroid is fluticasone propionate. In another embodiment, is a method for reducing adipose tissue in a subject wherein the pharmaceutical formulation provides a mean plasma fluticasone propionate $C_{max}$ between about 100 pg/mL and a level that is undetectable using current methodology. In a further embodiment, the subcutaneous administration results in a reduced or minimized risk of producing cardiovascular side effects. In yet a further embodiment, the subcutaneous administration results in a reduced or minimized risk of producing an increase in heart rate or a decrease in blood pressure or a combination thereof. In another embodiment, the subcutaneous administration provides a minimized risk of producing effects, such as, flushing, reddening, rapid heart rate, chest tightness, difficulty breathing, faintness, heart palpitations, hives, irregular or abnormal heart rate, paroxysmal bronchoconstriction, and hypersensitivity reaction such as angioedema and urticaria. Other reduced or minimized risk side effects include paradoxical bronchospasm, high blood pressure, abnormal heart rhythm, abnormally low blood pressure, an increase in asthma related conditions, bronchospasm, inflammation of the lining of the stomach and intestines, involuntary quivering, fast heartbeat, chest pain, and giant hives.

In some embodiments, provided herein is a pharmaceutical formulation that comprises salmeterol or a salt, optical isomer, racemate, solvate, or polymorph thereof and at least one subcutaneously acceptable inactive ingredient wherein the salmeterol is formulated in a single session dose that is between about 5 ng to about 20 µg and when subcutaneously administered to a patient, induces lipolysis of adipose tissue. In further or additional embodiments, provided herein is a pharmaceutical formulation comprising a single session dose of fluticasone propionate in an amount that is between about 1 µg and about 300 µg. In some embodiments, provided herein are pharmaceutical formulations comprising a weekly dose of salmeterol xinafoate that is between about 5 ng to about 150 µg. In further or additional embodiments, provided herein is a pharmaceutical formulation comprising a weekly dose of fluticasone propionate in an amount that is between about 50 ng and about 100 µg. In still further embodiments, provided herein is a pharmaceutical formulation comprising a sub-dose of salmeterol xinafoate in an amount that is between about 1 ng to about 50 µg. In other provided herein is a pharmaceutical formulation comprising a sub-dose of fluticasone propionate in an amount that is between about 5 ng to about 20 µg.

In further or additional embodiments, the formulation provides a mean plasma lipophilic, long-acting selective beta-2 adrenergic receptor agonist $C_{max}$ equal to or less than about 300 pg/mL (including $C_{max}$ levels that are undetectable using conventional methodology). In one embodiment, the lipophilic, long-acting selective beta-2 adrenergic receptor agonist is not formoterol. In one embodiment, provided is a method for inducing lipolysis in adipose tissue comprising subcutaneously administering to the subject a pharmaceutical formulation comprising a lipophilic, long-acting selective beta-2 adrenergic receptor agonist or a salt, optical isomer, racemate, solvate, or polymorph thereof and fluticasone propionate wherein the formulation provides a mean plasma fluticasone propionate $C_{max}$ equal to or less than about 100, about 90, about 80, about 70, about 60, about 50, about 40, about 30, about 20, about 10, about 1 pg/mL, or is undetectable using conventional methodology. In one embodiment, the mean plasma fluticasone propionate $C_{max}$ results from systemic administration. In another embodiment, the mean plasma fluticasone propionate $C_{max}$ results from subcutaneous administration. In other embodiments, the formulation comprises a fluticasone salt, such as by way of example only, fluticasone furoate, such that the mean plasma fluticasone furoate $C_{max}$ results from systemic administration. In another embodiment, the mean plasma fluticasone furoate $C_{max}$ results from subcutaneous administration. In yet other embodiments, the mean plasma fluticasone results from fluticasone furoate.

Methods of Reducing the Circumference of a Patient's Abdomen

It has been discovered that the subcutaneous administration of a lipophilic long-acting selective beta-2 adrenergic receptor agonist, e.g., salmeterol xinafoate, to a patient provides for a reduction in the circumference of the patient's waist or abdomen. In specific embodiments, the patient experiences a change in body weight that is less than about 5%, less than about 3%, less than about 2%, less than about 1%, or less than about 0.5% during a treatment period. For example, FIG. 8 illustrates that the mean body weight (in kg) did not show any significant change when measured at baseline, 4 weeks from start of treatment (i.e., end of treatment), 1 week post-treatment, and 4 weeks post-treatment, for all patients enrolled in the study described in Example 3B. See FIG. 8.

Accordingly, in another aspect, provided herein is a method for reducing the circumference of a patient's waist comprising subcutaneously administering a pharmaceutical formulation suitable for subcutaneous injection comprising: (a) a lipophilic long-acting selective beta-2 adrenergic receptor agonist or glucocorticosteroid, or a salt, optical isomer, racemate, solvate, or polymorph thereof; and (b) at least one subcutaneously acceptable inactive ingredient wherein the patient experiences a change in body weight that is less than about 5%, less than about 3%, less than about 2%, less than about 1%, or less than about 0.5% during a treatment period. In some embodiments, the circumference of the patient's waist is reduced by at least about 1 centimeter, at least about 1.5 centimeters, at least about 2 centimeters, at least about 2.5 centimeters, at least about 3 centimeters, at least about 3.5 centimeters, at least about 4 centimeters, at least about 4.5 centimeters, or at least about 5 centimeters. In some embodiments, the circumference of the patient's waist is reduced by at least about two centimeters. In some embodiments, the circumference of the patient's waist is reduced by at least about 2.5 centimeters. In further or additional embodiments, the reduction in the patient's waist is evident at about 6 to 8 weeks from the first day of treatment. In some embodiments, the lipophilic long-acting selective beta-2 adrenergic receptor agonist is salmeterol xinafoate.

In another embodiment, provided herein is a method for reducing the circumference of a patient's waist or abdomen comprising the subcutaneous administration of a glucocorticosteroid that is fluticasone or a salt or solvate thereof. In another embodiment, the salt is a propionate or furoate salt. In further embodiments, the salt is a furoate salt. In yet a further embodiment, the glucocorticosteroid is fluticasone propionate. In another embodiment, is a method for reducing adipose tissue in a subject wherein the pharmaceutical formulation provides a mean plasma fluticasone propionate $C_{max}$ between about 100 pg/mL and a level that is undetectable using current methodology. In a further embodiment, the subcutaneous administration results in a reduced or minimized risk of producing cardiovascular side effects. In yet a further embodiment, the subcutaneous administration results in a reduced or minimized risk of producing an increase in heart rate or a decrease in blood pressure or a combination thereof. In another embodiment, the subcutaneous administration provides a minimized risk of producing anaphylaxis related effects, such as, flushing, reddening, rapid heart rate, chest tightness, difficulty breathing, faintness, heart palpitations, hives, irregular or abnormal heart rate, paroxysmal bronchoconstriction, and hypersensitivity reaction such as angioedema and urticaria. Other reduced or minimized risk side effects include paradoxical bronchospasm, high blood pressure, abnormal heart rhythm, abnormally low blood pressure, an increase in asthma related conditions, bronchospasm, inflammation of the lining of the stomach and intestines, involuntary quivering, fast heartbeat, chest pain, and giant hives.

In some embodiments, provided herein is a pharmaceutical formulation that comprises salmeterol or a salt, optical isomer, racemate, solvate, or polymorph thereof and at least one subcutaneously acceptable inactive ingredient wherein the salmeterol is formulated in a single session dose that is between about 5 ng to about 20 μg. In specific emboidments, when subcutaneously administered to a patient, the formulations provided herein provide a reduction in the circumference of the patient's waist and the patient experiences a change in body weight that is less than about 5%, less than about 3%, less than about 2%, less than about 1%, or less than about 0.5% during a treatment period. In further or additional embodiments, provided herein is a pharmaceutical formulation comprising a single session dose of fluticasone propionate in an amount that is between about 1 μg and about 300 μg. In some embodiments, provided herein are pharmaceutical formulations comprising a weekly dose of salmeterol xinafoate that is between about 5 ng to about 150 μg. In further or additional embodiments, provided herein is a pharmaceutical formulation comprising a weekly dose of fluticasone propionate in an amount that is between about 50 ng and about 100 μg. In still further embodiments, provided herein is a pharmaceutical formulation comprising a sub-dose of salmeterol xinafoate in an amount that is between about 1 ng to about 50 μg. In other embodiments, provided herein is a pharmaceutical formulation comprising a sub-dose of fluticasone propionate in an amount that is between about 5 ng to about 20 μg.

In further or additional embodiments, provided herein is a method for reducing the circumference of a patient's waist wherein the formulation provides a mean plasma lipophilic, long-acting selective beta-2 adrenergic receptor agonist $C_{max}$ equal to or less than about 300 pg/mL (including $C_{max}$ levels that are undetectable using conventional methodology). In another embodiment, the lipophilic, long-acting selective beta-2 adrenergic receptor agonist is not formoterol. In one embodiment, provided is a method for inducing lipolysis in adipose tissue comprising subcutaneously administering to the subject a pharmaceutical formulation comprising a lipophilic, long-acting selective beta-2 adrenergic receptor agonist or a salt, optical isomer, racemate, solvate, or polymorph thereof and fluticasone propionate wherein the formulation provides a mean plasma fluticasone propionate $C_{max}$ equal to or less than about 100, about 90, about 80, about 70, about 60, about 50, about 40, about 30, about 20, about 10, about 1 pg/mL, or is undetectable using conventional methodology. In one embodiment, the mean plasma fluticasone propionate $C_{max}$ results from systemic administration. In another embodiment, the mean plasma fluticasone propionate $C_{max}$ results from subcutaneous administration. In other embodiments, the formulation comprises a fluticasone salt, such as by way of example only, fluticasone furoate, such that the mean plasma fluticasone furoate $C_{max}$ results from systemic administration. In another embodiment, the mean plasma fluticasone furoate $C_{max}$ results from subcutaneous administration. In yet other embodiments, the mean plasma fluticasone results from fluticasone furoate.

Pharmaceutically Acceptable Excipients

In a further embodiment, the at least one subcutaneously acceptable inactive ingredient is a co-solvent. In further or additional embodiments, the co-solvent is selected from about 0.25 to about 40% polyethylene glycol. In further or additional embodiments, the polyethylene glycol is about 0.8- about 1%. In a further embodiment, the polyethylene glycol is PEG 400.

In yet a further embodiment, the at least one subcutaneously acceptable inactive ingredient is selected from about 0.01 to about 10% polysorbate. In some embodiments, the polysorbate is about 0.01- about 2% polysorbate. In still further embodiments, the polysorbate is about 0.04%. In one embodiment, the polysorbate is polysorbate 80.

Excipients used in the formulations described herein include, but are not limited to, suspending agents, surfactants, solubilizers such as, for example, PEG 400, stabilizers, diluents and the like, and should be selected on the basis of compatibility with the lipophilic long-acting beta-2 adrenergic receptor agonist and/or in cases of a combination formulation for subcutaneous administration, glucocorticosteroids. In some embodiments, a polyalkylene glycol or a mixture of different polyalkylene glycols is used as a solubilizer. Polyalkylene glycols from the group of polypropylene glycols or polyethylene glycols are particularly suitable in this connection because of the physiological tolerance. In this connection, the use of polyethylene glycols is utilized in some embodiments presented herein. In some embodiments, polyethylene glycols such as, for example, PEG 400, is contemplated herein.

Additives increasing the bioavailability of a lipophilic long-acting beta-2 adrenergic receptor agonist, such as, salmeterol are, in some embodiments, organic compounds, salts thereof, optical isomers or racemates thereof, emulsions or dispersions containing organic compounds or salts thereof, e.g. dispersions of polar lipids, or any combination. Organic compounds useful in the subcutaneous formulation are e.g. amino acids, peptides, proteins, and polysaccharides. Peptides include dipeptides, tripeptides, oligopeptides, such as collagen and gelatine. In some embodiments, the collagen and gelatine is hydrolyzed. Polysaccharides include e.g., chitosans, cyclodextrins, starch, hyaluronic acids, dextrans, cellulose, and any derivatives, combinations. In further embodiments, the starch is hydrolyzed. The emulsions include oil-in-water emulsions with oil as the dispersed phase and water-in-oil dispersions with oil as the continuous phase. In other embodiments, the oil is of vegetable or of animal origin or synthetically produced. In further embodiments, the polar liquids are one or more phospholipids or glycolipids or any combination thereof. In some other embodiments, the additives increasing the bioavailability of a lipophilic long-acting beta-2 adrenergic receptor agonist, such as, salmeterol are added to a stable solution or dispersion containing the lipophilic long-acting beta-2 adrenergic receptor agonist.

In further embodiments, before administration, one or more aqueous solutions or dispersions are added, in any mixture or sequence, to the lipophilic long-acting beta-2 adrenergic receptor agonist, such as, salmeterol, which is a stable aqueous solution. In other embodiments, the formulation is a stable aqueous solution ready for administration. In some embodiments, it is a dispersion, e.g. a suspension, a liposomal formulation or an emulsion. In yet other embodiments, the formulation also comprises a salt in order to give an isotonic solution, e.g., NaCl, KCl, and/or in further embodiments, it comprises one or more other isotonicity establishing compounds.

In yet other embodiments, an amino acid is used to buffer the system. In some embodiments, a suitable buffer is glycine, lysine, arginine, histidine or glycylglycine, in other embodiments, the buffer is glycylglycine.

In some other embodiments, a non-ionic surfactant is also present in the formulation. In some embodiments, the surfactant is chosen from block-copolymers, such as a poloxamer, e.g., poloxamer 188, or a polyoxyethylene sorbitan fatty acid ester, such as polyoxyethylene-(20)-sorbitan monolaurate or polyoxyethylene-(20)-sorbitan monooleate. Also disclosed herein are formulations using polyoxyethylene-(20)-sorbitan monolaurate (Tween 20). In one embodiment, the formulation described herein used polyoxyethylene-(20)-sorbitan monooleate (Tween 80). In other embodiments, the non-ionic surfactant, is present in an amount above the critical micelle concentration (CMC).

Also presented herein are mono- or disaccharides (e.g., sucrose), polysaccharides such as low molecular weight dextrins, or sugar alcohols (e.g., sorbitol, glycerol or mannitol) used in the subcutaneous formulations. In some embodiments, the formulation also comprises antioxidants such as bisulfate, ascorbate glutathione, acetylcystein, tocopherol, methionin, EDTA, citric acid, butyl hydroxy toluene and/or butyl hydroxy anisole. In other embodiments, complexing agents, such as EDTA and citric acid are also present in small concentrations for stabilizing the lipophilic long-acting beta-2 adrenergic receptor agonist, such as, salmeterol. Furthermore, in other embodiments, preservatives such as benzyl alcohol, phenol, sorbic acid, parabens, and chlorocresol are added.

Routes of Administration

Injectable formulations are administered using any method known in the art, for example, using a single needle, multiple needles, and/or using a needleless injection device. In some embodiments, a tissue loading dose of the active ingredients formulated in a suitable carrier delivered by injection. In some embodiments, delivery comprises single needle injection. In some embodiments, delivery comprises injection using a multi-needle array, which, in some embodiments, provides a wide dispersion of the formulation in the target tissue. In some embodiments, formulations are injected in a manner that allows dispersal into the appropriate layer of subcutaneous fat in or near regional fat areas.

Transcutaneous formulations, also contemplated as a route of delivery for the pharmaceutical formulations and methods of treatment provided herein, are administered using any known method in the art.

In some embodiments, the beta-2 agonist and the compound that reduces desensitization are administered in a non-inhalation manner, for example by injection. In some embodiments, the formulations provided herein are administered as separate formulations, or, alternatively, are administered by separate routes administered followed by injection of a lipophilic, long-acting beta-2 agonist. In some embodiments, the compound that reduces desensitization is administered prior to the beta-2 agonist. In other embodiments, the beta-2 agonist is administered prior to the compound that reduces desensitization.

Embodiments of the composition are formulated for administered by any suitable method, for example, as described in *Remington: The Science And Practice Of Pharmacy* (21st ed., Lippincott Williams & Wilkins). Exemplary routes of administration include, but are not limited to parenteral, subcutaneous, or intramuscular. In some embodiments, the composition is formulated for injection of an area at which treatment is desired, for example, in or near a regional fat deposit.

Any suitable pharmaceutically acceptable excipient appropriate for a particular route of administration can be used. Examples of pharmaceutically acceptable carriers include, but are not limited to, buffers, saline, or other aqueous media. The compounds described herein are in some embodiments, soluble in the carrier which is employed for their administration (e.g., subcutaneous). Some embodiments comprise any suitable lipophilic carrier, for example, modified oils (e.g., Cremophor® BASF, Germany), soybean oil, propylene glycol, polyethylene glycol, derivatized polyethers, combinations thereof, and the like. Some embodiments comprise one or more carriers or agents, suitable for subcutaneous administration. Some embodiments comprise excipients suitable for stable suspensions for beta-2 receptor agonists and glucocorticosteroids.

In some embodiments, the pharmaceutical formulations comprise polyethylene glycol in an amount of from about 0.5% to about 40%. In another embodiment, the formulation suitable for subcutaneous administration comprises polyethylene glycol in an amount from about 0.5%, about 1%, about 2%, about 3%, about 4%, about 5%, about 10%, about 15%, about 20%, about 25%, about 30%, about 35%, and about 40%. In a further embodiment, polyethylene glycol is in an amount of about 20%. In yet a further embodiment, polyethylene glycol is PEG 400. In yet another embodiment, the pharmaceutical formulations comprise polysorbate in an amount of from 0.01% to about 10%. In another embodiment, the formulation suitable for subcutaneous administration comprises polysorbate in an amount from about 0.01%, about 0.02%, about 0.03%, about 0.04%, about 0.05%, about, about 0.06%, about 0.07%, about 0.08%, about 0.09%, 0.1%, about 0.2%, about 0.3%, about 0.4%, about 0.5%, about, about 0.6%, about 0.7%, about 0.8%, about 0.9%, about 1%, about 2%, about 3%, about 4%, about 5%, about 6%, about 7%, about 8%, and about 9%. In a further embodiment, polysorbate is in an amount of about 10%. In yet a further embodiment, polysorbate is polysorbate 80.

In other embodiments, another delivery mode comprises a needless pressurized injection device. In some embodiments, of these devices, the formulation is pressurized mechanically or pneumatically, for example, using a gas such as helium or carbon dioxide, and then forced through a small orifice into the body tissues, thereby delivering the formulation subcutaneously. Suitable formulations for needless injections are known, for example, liquid, solutions, suspensions, gels, colloids, emulsions, and dry powders. An advantage of this system is a wide dispersal area compared with typical needle injection systems. Needless injection under the appropriate pressure forces the formulation into a more planar delivery pattern, with fingers of formulation spreading out radially following paths of least resistance. In contrast, delivery by a typical needle injection results in a globular delivery of the formulation. Needless injection also permits precise control of the depth of penetration by controlling the injection pressure and orifice size. Thus, needless injection is a delivery method for a sub-dermal injection contemplated herein of a formulation for treating superficial fat accumulations, which is useful, for example, for smoothing skin dimpling caused by fat. In other embodiments, needless injection is also used for deeper fat accumulations. In further embodiments, a needless device also provides easy and convenient multiple injections of the formulation over a defined region with a large lateral spread.

In some embodiments, the interval between administration of the compound that reduces desensitization and administration of the beta-2 agonist can be an interval from less than about 5 minutes, about 5 minutes to about 1 month, e.g., 10 minutes, 15 minutes, 20 minutes, 30 minutes, 1 hour, 6 hours, 12 hours, one day, 2 day, 3 days, 4 days, 5 days, 6 days, 7 days, 10 days, 2 weeks, 3 weeks, or any other time interval from about 5 minutes to about 1 month. In another embodiment, the compound that reduces desensitization (e.g., a glucocorticosteroid) is administered orally up to about 7 days, e.g., 3 days, 4 days, 5 days, 6 days, 7 days, 8 days, 9 days, or 10 days prior to administering the beta-2 agonist (e.g., by local injection into or near a fat deposit).

In other embodiments, the beta-2 agonist is co-administered concomitantly (e.g., as part of the same formulation) with the compound that reduces beta-adrenergic receptor desensitization (e.g., a glucocorticosteroid). In further or additional embodiments, co-administration is provided sequentially (e.g., separately but one agent administered after the other), or concurrently (e.g., at the same time but the agents are, e.g., in different formulations).

In some embodiments, the subject to be treated is provided a non-sustained release formulation. In some embodiments, the non-sustained release formulation, after a single dose, provides activity of one or more long-acting selective beta-2 agonists for a duration from about 4 hours to about 24 hours, e.g., about 6 hours, 8 hours, 10 hours, 12 hours, 16 hours, 18 hours, 21 hours, or any other duration of beta-2 agonist activity from about four hours to about 24 hours.

Treatment of Other Conditions

In some embodiments, the above-mentioned drugs and combinations are used for treating immune and inflammation-related dermal conditions including psoriasis, atopic dermatitis, vitiligo, hypopigmentation, stria, and wrinkles or rhytids. In one embodiment, a combination of lipophilic, long-acting selective beta-2 agonists and ketotifen is administered subcutaneously. In another embodiment, a combination of a beta agonist and a glucocorticoid are used for treating immune and inflammation-related dermal conditions. The principle of upregulating the beta-adrenergic receptor number and reducing the desensitization of the beta-adrenergic receptor through the use of ketotifen (or a glucocorticoid) in combination with a selective beta-2 agonist, such as salmeterol is useful in the treatment of dermal conditions such as dermatitis (e.g., atopic) and psoriasis. Other drugs which stabilize the beta-2 adrenergic receptor and/or up regulate the receptor for treating dermal conditions include, but are not limited to, thyroid hormone, 1,25-dihydroxy vitamin D3 or it analogue, and bioflavanoids such as quercetin or fisetin. In some embodiments, darkening of skin or hypopigmented areas, such as occurs in vitiligo, stria, or a lack of sunlight is treated with the proposed combinations and principles of beta-adrenergic receptor upregulation as described herein. In one embodiment, a combination of long-acting beta-adrenergic agonists with other drugs that stabilize and/or increase the beta-2 adrenergic receptor is used in a subcutaneous formulation to treat the afore-mentioned conditions. In some embodiments, a combination of long-acting beta-adrenergic agonists with other drugs that enhance the cAMP response to beta-2 adrenergic receptor stimulation is utilized. In one embodiment, a combination of salmeterol with ketotifen is used to treat psoriasis. In some embodiments, where the beta-2 adrenergic receptor has defective activity, forskolin is used in the combination. Antigen presentation by the Langerhans cells may incite the immune component of the disease. The pathogenesis of psoriasis includes overproliferation of keratinocytes and immune inflammatory reactions, including lymphocyte (such as T-cells) migration and activation in the psoriatic lesion. Psoriasis may be characterized by T-helper 1 (Th1) type responses. In some embodiments, subcutaneously administrable lipophilic, long-acting beta-andrenergic agonists are used to control the proliferation of the keratinocyte and lymphocytes including T-cells. In some embodiments, long-acting beta-adrenergic agonists are also used to inhibit Th1 responses. In some embodiments, subcutaneously administrable lipophilic, long-acting beta-adrenergic agonist treatment is used to decrease Langerhans cell migration and antigen presentation. In some embodiments, ketotifen can be used to stabilize and upregulate beta-2 adrenergic receptors on lymphocytes, keratinocytes, or dermal fibroblasts. In addition ketotifen inhibits the release of cytokines such as tumor necrosis factor alpha (TNF-alpha). TNF-alpha plays a role in the pathogenesis of psoriasis. Thus, blocking the action of this cytokine (e.g., with antibodies), or reducing the release of the cytokine reduces the severity of skin lesions. In some embodiments, ketotifen is administered to inhibit T-cell activity and thereby reduce inflammatory immune responses.

In another embodiment, long-acting beta-adrenergic agonists, such as salmeterol xinafoate, its stereoisomers, as physiologic salts, optical isomers, racemates, solvates or polymorphs thereof, are combined with 1,25-dihydroxy Vitamin D3 or its analogues. In some embodiments, 1,25-dihydroxy Vitamin D3 enhances beta-adrenergic adenylate cyclase responses in keratinocytes. In conditions, such as psoriasis, cAMP levels are low or cAMP formation is impaired. Accordingly, in some embodiments, where a subject is suffering from psoriasis, Vitamin D3 is administered in combination with a subcutaneous formulation consisting essentially of a long-acting beta-adrenergic agonist, such as salmeterol.

In some embodiments, beta-2 adrenergic receptor agonists are administered subcutaneously for the treatment of skin wrinkles and skin stria, or stretch marks. Cutaneous stria are characterized by a thinning of the dermis, with a loss of collagen and hypopigmention. Long-acting beta-adrenergic agonists promote the recruitment and proliferation and collagen production of dermal fibroblasts in the stria. In addition, they stimulate melanocytes to repigment the stria. Thus, in some embodiments a subcutaneous formulation consisting essentially of an adipose tissue-reducing amount of salmeterol or a salt, solvate, or polymorph thereof is used in combination with other drugs to stabilize and up regulate the beta-2 adrenergic receptor such as those disclosed above, including ketotifen, glucocorticoids, thyroid hormone, and bioflavanoids quercetin and fisetin. In some embodiments, forskolin is used with the lipophilic, long-acting beta-adrenergic agonist and in combination with the previously disclosed compounds (e.g. quercetin, fisetin, glucocorticoid, or ketotifen) to treat cutaneous stria and wrinkles.

The combination of a selective lipophilic long-acting beta-adrenergic agonist is also suitable for the treatment of cachexia. Ketotifen can cause weight gain, which may be due to increased food intake secondary to appetite or satiety effects. Hence, the combination may have pronounced effects on cachexia, or wasting syndromes, secondary to other medical conditions such as HIV infection, cancer, or heart failure. Additionally, as previously disclosed the combination of a long-acting beta-2 adrenergic receptor agonist and ketotifen in a formulation suitable for parenteral administration, such as subcutaneous administration, has enhanced effects by increasing beta-adrenergic receptor numbers and reducing receptor deactivation.

In some embodiments, beta-2 adrenergic receptor agonists are administered to increase skeletal muscle mass and cause hypertrophy and increased protein synthesis, effects which are mediated through intracellular in increases cAMP levels. Similar to adipocytes, exposure to beta-2 adrenergic receptor agonists results in receptor down-regulation. Thus, in the disclosed formulations, combinations are also used for treating skeletal muscle injury or conditions where increasing skeletal muscle mass is important. In some embodiments, the methods described herein are used to increase facial muscle tone and provide a more youthful appearance. In some embodiments, the methods described herein are used to treat strabismus or lazy eye by strengthening ocular muscles. In some embodiments, combinations include adipose tissue-reducing lipophilic, long-acting beta-adrenergic agonists, such as salmeterol xinafoate, and compounds that reduce desensitization of beta-2 adrenergic receptors, e.g., beta-2 adrenergic receptor stabilizers/upregulators glucocorticoids or ketotifen in a suitable formulation for subcutaneous administration. In some embodiments, bioflavanoids, such as quercetin or fisetin, are also used to decrease beta-2 adrenergic receptor desensitization. In some embodiments, glucocorticoids and adipose tissue-reducing lipophilic, long-acting beta-adrenergic agonists are co-administered to a subject to repair a muscle injury. In some embodiments, agents that increase cAMP such as forskolin are used for treating skeletal muscle injury or improving facial muscle tone.

In other embodiments, provided are methods for decreasing cellulite in a subject, also known as adiposis edematosa, dermopanniculosis deformans, status protrusus cutis, and gynoid lipodystrophy, comprising administering via subcutaneous methods, a subcutaneous formulation consisting essentially of a long-acting beta-2 adrenergic receptor agonist and a subcutaneously acceptable excipient thereof, wherein the formulation decreases cellulite in the subject.

Areas of fat deposits on a subject, such as for example a human patient, for which the formulations described herein are useful include, but are not limited to, the inside region of the knees, the middle to upper area of the upper arm, including the tricep area, the submental area, including the area under the chin, for example the wattle (which is understood to refer to the fleshy fold of skin in the submental area of a patient), the abdomen, the hips, the inner thigh, the outer thigh, the buttocks, the lower back and the chest.

In some embodiments, inducing lipolysis and inhibiting fat cell growth in regional fat accumulations, have additional health benefits through the shrinkage of the average fat cell diameter or volume. Large volume fat cells actively secrete pro-inflammatory and deleterious hormones such as TNF-alpha and interleukins ("adipokines"), which contribute to comorbidities associated with fat, such as diabetes. By reducing the size of these fat cells and therefore the deleterious adipokine secretion, improvements in fat-related comorbidities are realized.

In some embodiments, the disclosed formulations (e.g., subcutaneous and transcutaneous formulations), and combinations described herein are used for treating obstructive sleep apnea. Obstructive sleep apnea occurs when the airway is temporarily blocked during sleep, leading to hypoxia, high blood pressure, cardiac dysrhythmia, and a higher risk of death. Excessive fat in the pharynx and soft palate it believed to contribute to this blockage. Obese people have a higher incidence of sleep disorders and persons with sleep apnea have excessive fat in the palate and pharynx on MRI. Thus, in some embodiments, formulations described are administered to a subject to reduce the symptoms of sleep apnea. In some embodiments, the formulations are administered locally (e.g., by injection) into the palate or pharynx transorally. In some embodiments, the formulations are administered by subcutaneous into the region the neck to reduce the obstructive symptoms.

While certain embodiments have been described, these embodiments have been presented by way of example only, and are not intended to limit the scope of the disclosure. The formulations, methods, and systems described herein may be embodied in a variety of other forms. Furthermore, various omissions, substitutions and changes in the form of the formulations, methods, and systems described herein may be made without departing from the spirit of this disclosure. The accompanying claims and their equivalents are intended to cover such forms or modifications.

EXAMPLES

The following specific examples are to be construed as merely illustrative, and not limitative of the remainder of the disclosure in any way whatsoever. The examples described herein reference and provide non-limiting support to the various embodiments described in the preceding sections.

Example 1

Plasma Pharmacokinetics Following Single Intravenous and Subcutaneous Injections of Salmeterol Xinafoate Materials and Methods: Salmeterol xinafoate was formulated in 5% PEG-400 in 0.9% saline, USP, at concentrations of 0.1, 1, 10, and 100 µg/mL. 1 male and 1 female non-naive Gottingen minipigs (18.4 to 19.5 kg at the time of the IV dose) were utilized. The animals were housed individually. The dosing scheme is shown in Table 1 below:

| Injection # | Route | Dose (µg/kg) | No. Animals/sex |
|---|---|---|---|
| 1 | IV | 4 | 1 |
| 2 | SC | 4 | 1 |
| 3 | SC* | 4 | 1 |
| 4 | SC* | 0.004 | 1 |
| 5 | SC* | 0.04 | 1 |
| 6 | SC* | 0.4 | 1 |

*The dose volume was equally divided over 5 injection sites

Each minipig received a single IV injection followed by SC doses of the salmeterol formulation. The IV dose was administered by slow bolus (1 minute; 0.0167 hr) into the marginal ear vein, whereas the first SC dose was administered as a bolus injection along the back (neck-region) where there was a longitudinal fat depot. The second SC dose was distributed in 5 separate SC injection sites. The fourth, fifth, and sixth administrations were SC administrations divided over 5 injection sits of different graded concentrations (0.1, 1, and 10 μg/mL of salmeterol in 5% PEG). Each dose was separated by at least a 3-day washout period. Blood samples (approximately 4 mL) were collected via the branchiocephalic plexus at pre-dose and at 2.00, 5.00, 10.0, 20.0, 30.0 and 45.0 minutes, and at 1.00, 2.00, 4.00, 8.00 and 24.0 hr post-dose. Blood samples were placed in tubes containing $K_2$-EDTA as the anticoagulant. Samples were processed to plasma by centrifugation and stored frozen at approximately −70° C. (+/− 15° C.) until shipment for analysis.

Sample Analysis: Plasma samples were analyzed for salmeterol using a qualified liquid chromatography/mass spectrometry/mass mass spectrometry (LC/MS/MS) method. The lower limit of quantitation (LLOQ) was 2.50 pg/mL. Samples were analyzed within a maximum of 14.0 days of collection.

Data Analysis: Non-compartmental pharmacokinetic parameters were calculated using WinNonlin 5.2 software, NCA model 202, IV infusion input for the IV data and NCA model 200, extravascular input for the SC data. Individual plasma concentrations for each animal were used in the calculation of pharmacokinetic parameters. Nominal collection times and doses were used in the calculations. The area under the plasma concentration-time curve (AUC) was calculated using linear trapezoidal approximation (linear/log interpolation). Concentration values below the assay limit of quantitation were set to zero for calculations. The maximum plasma concentration ($C_{max}$) and the time of its occurrence ($T_{max}$) were verified by inspection. The half-life ($t_{1/2}$) values were calculated using the last 3 plasma concentrations with non-zero values, if data permitted.

Figure 1:
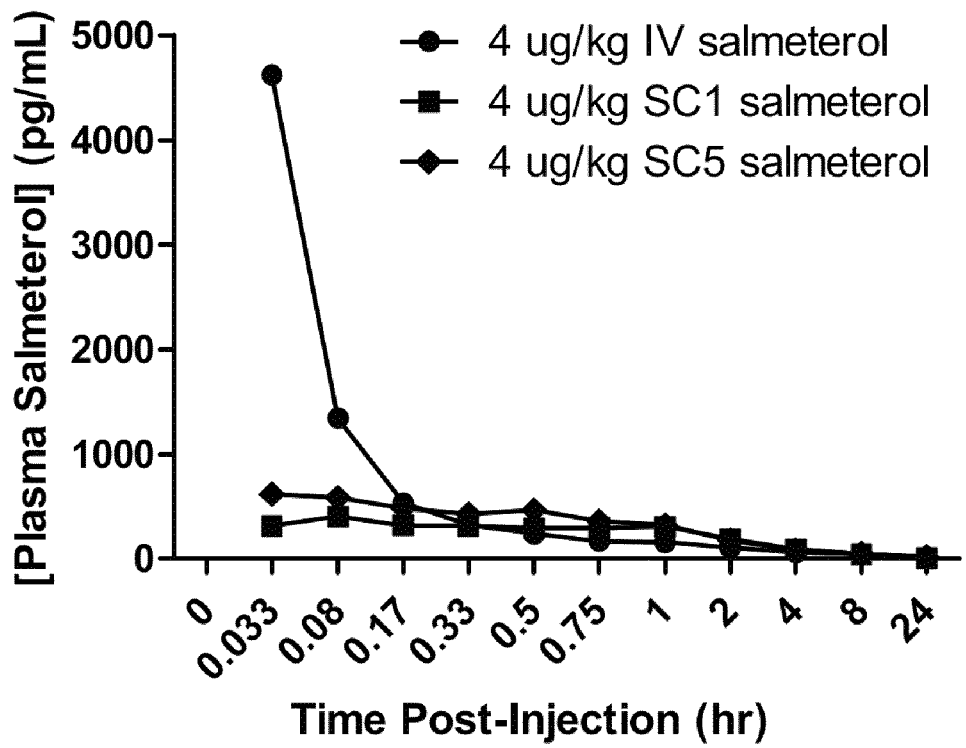
FIG. 1 is illustrative of the plasma concentrations of salmeterol and formoterol following intravenous and subcutaneous administration to Gottingen minipigs.
Figure 1:
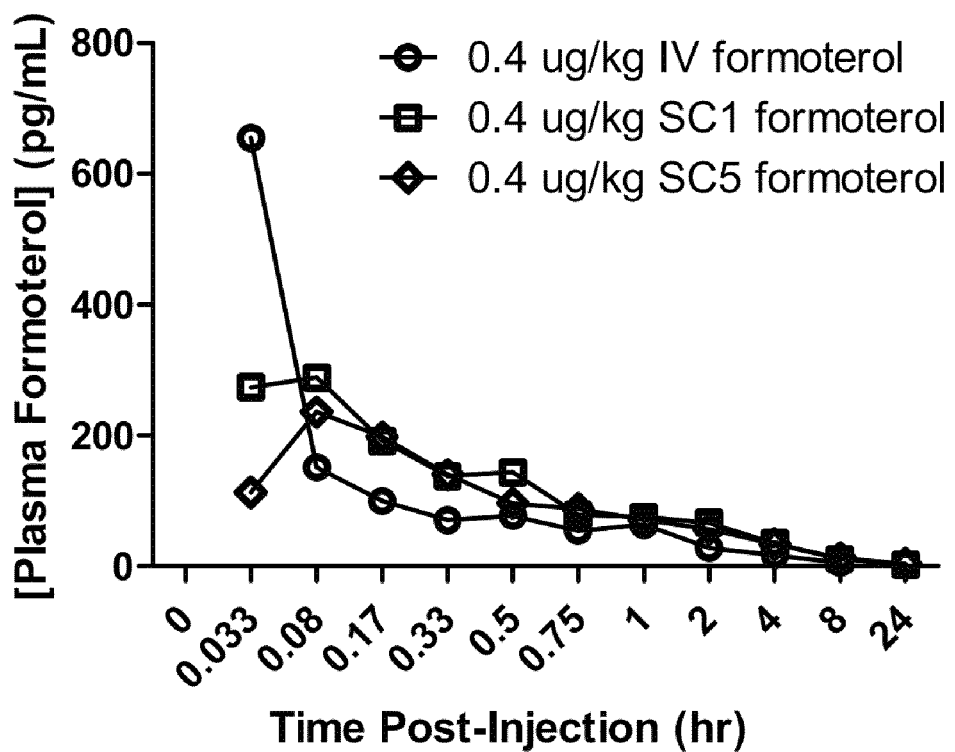

Results: The pharmacokinetic parameters are shown in Table 2. The plasma concentrations of salmeterol are shown in Table 3. The plasma concentrations of salmeterol and formoterol (via subcutaneous and intravenous administration) are shown in FIG. 1. Actual sampling times differed from nominal sampling times on occasion by more than 10%. Data in the apparent elimination phase were inadequate to calculate some pharmacokinetic parameters for some animals (indicated as ND for not determined or NA for not applicable). Bioavailability was likely poorly estimated due to scarcity of data in the apparent terminal elimination phase to calculate the apparent terminal elimination rate constant. This affected calculation of $AUC_{inf}$, $t_{1/2}$, CL, $V_{ss}$, and F. These departures are not believed to have significantly impacted the overall pharmacokinetic conclusions.

TABLE 2

Pharmacokinetic Parameters of Salmeterol Following IV and SC Administration to Gottingen Minipigs

| Route | Sex | Animal | $T_{max}$ (hr) | $C_{max}$ (Pg/mL) | $AUC_{inf}$ (pg · hr/mL) | $t_{1/2}$ (hr) | $t_{last}$ (hr) | CL (mL/hr/kg) | $V_{ss}$ (mL/kg) |
|---|---|---|---|---|---|---|---|---|---|
| IV | Female | 2-0623 | 0.0333 | 4950 | 1470 | 9.52 | 24.0 | 2730 | 22100 |
| IV | Male | 1-0771 | 0.0333 | 4290 | 1750 | 7.89 | 24.0 | 2280 | 17100 |

| Route | Dose (μg/kg) | Sex | Animal | $T_{max}$ (hr) | $C_{max}$ (Pg/mL) | $AUC_{inf}$ (pg · hr/mL) | $t_{1/2}$ (hr) | $t_{last}$ (hr) | F |
|---|---|---|---|---|---|---|---|---|---|
| SC1 | 4 | Female | 2-0623 | 1.00 | 403 | 1850 | 6.02 | 24.0 | 1.26 |
| SC5 | 4 | Female | 2-0623 | 0.0333 | 626 | 2010 | 8.58 | 24.0 | 1.37 |
| SC1 | 4 | Male | 1-0771 | 0.0833 | 575 | 1290 | 5.92 | 24.0 | 0.737 |
| SC5 | 4 | Male | 1-0771 | 0.0833 | 681 | 1510 | 6.84 | 24.0 | 0.863 |
| SC5 | 0.004 | Female | 2-0623 | 1.00 | 3.08 | ND | ND | 1.00 | ND |
| SC5 | 0.004 | Male | 1-0771 | NA | 0 | ND | ND | NA | ND |
| SC5 | 0.04 | Female | 2-0623 | 0.0333 | 8.31 | ND | ND | 0.0833 | ND |
| SC5 | 0.04 | Male | 1-0771 | 0.0833 | 2.77 | ND | ND | 0.0833 | ND |
| SC5 | 0.4 | Female | 2-0623 | 0.0333 | 113 | 164 | 2.88 | 8.00 | 1.12 |
| SC5 | 0.4 | Male | 1-0771 | 0.0833 | 64.5 | 138 | 2.94 | 8.00 | 0.789 |

$AUC_{inf}$ = area under the curve at infinite time. CL = plasma clearance. F = bioavailability; NA = not applicable; ND = not determined; SC1—single site injection; SC5 = SC injection split among 5 sites, $t_{last}$ = time of last measurable plasma concentration. $V_{ss}$ = volume of distribution at steady state
The IV dose was 4 μg/kg
The injection 4 SC5 0.004 μg/kg male showed no plasma concentrations > LLOQ of salmeterol at any time point.

TABLE 3

Plasma Concentrations of Salmeterol Following IV and SC Administration to Gottingen Minipigs (08-529)

| | | Dose | | | Time (hr) | | | | | | | | | | |
|---|---|---|---|---|---|---|---|---|---|---|---|---|---|---|---|
| Inj | Rte | (mg/kg) | Sx | 0 | 0.0333 | 0.0833 | 0.167 | 0.333 | 0.500 | 0.750 | 1.00 | 2.00 | 4.00 | 8.00 | 24.0 |
| 1 | IV | 4 | M | < | 4290 | 1380 | 502 | 326 | 240 | 177 | 161 | 121 | 70.6 | 53.6 | 12.5 |
| 1 | IV | 4 | F | < | 4950 | 1300 | 559 | 322 | 232 | 152 | 154 | 81.1 | 49.1 | 35.3 | 11.3 |
| 2 | SC | 4 | M | < | 495 | 575 | 423 | 284 | 278 | 236 | 212 | 168 | 74.5 | 30.6 | 6.23 |
| 2 | SC | 4 | F | < | 124 | 227 | 206 | 334 | 302 | 351 | 403 | 206 | 108 | 54.4 | 10.0 |
| 3 | SC5 | 4 | M | < | 604 | 681 | 519 | 449 | 483 | 278 | 251 | 148 | 75.6 | 36.1 | 8.92 |
| 3 | SC5 | 4 | F | < | 626 | 485 | 442 | 398 | 435 | 435 | 388 | 196 | 86.8 | 51.0 | 16.1 |

TABLE 3-continued

Plasma Concentrations of Salmeterol Following IV and SC Administration to Gottingen Minipigs (08-529)

| Inj | Rte | Dose (mg/kg) | Sx | 0 | 0.0333 | 0.0833 | 0.167 | 0.333 | 0.500 | 0.750 | 1.00 | 2.00 | 4.00 | 8.00 | 24.0 |
|---|---|---|---|---|---|---|---|---|---|---|---|---|---|---|---|
| 4 | SC5 | 0.004 | M | < | < | < | < | < | < | < | < | < | < | < | < |
| 4 | SC5 | 0.004 | F | < | < | < | < | < | < | < | 3.08 | < | < | < | < |
| 5 | SC5 | 0.04 | M | < | < | 2.77 | < | < | < | < | < | < | < | < | < |
| 5 | SC5 | 0.04 | F | < | 8.31 | 3.17 | < | < | < | < | < | < | < | < | < |
| 6 | SC5 | 0.4 | M | < | 32.0 | 64.5 | 57.0 | 43.3 | 53.8 | 26.5 | 28.7 | 19.5 | 8.46 | 4.41 | < |
| 6 | SC5 | 0.4 | F | < | 113 | 55.4 | 42.9 | 59.8 | 83.5 | 34.5 | 32.2 | 24.5 | 8.58 | 5.15 | < |

Plasma concentrations are reported in pg/mL. LLOQ = 2.50 pg/mL.
< = LLOQ; F = female; Inj = Injection number; M = male; Rte = route; SC1 = single site injection; SC5 = SC injection split among 5 sites; Sx = sex.
The male animal was number 1-0771 and the female animal number was number 2-0623

Overall there were no consistent, substantial differences in $C_{max}$ or $AUC_{inf}$ values between the male and female animal. Additionally, there was not a substantial difference in $C_{max}$ and $AUC_{inf}$ values between single site SC doses and multiple (5) site SC doses at the 4 µg/kg dose. The ratios (SC1/SC5) ranged from 0.644 to 0.844 for $C_{max}$ and 0.854 and 0.920 for $AUC_{inf}$. Salmeterol appeared to be well absorbed after SC administration at a single site at 4 µg/kg and after divided SC administration at 5 sites at the 4 and 0.4 µg/kg doses; bioavailability ranged from 0.737 to 0.863 for the male and 1.26 to 1.37 for the female for the 4 µg/kg dose regardless of the number of sites of administration and 0.789 for the male and 1.12 for the female for the 0.4 µg/kg dose at 5 divided SC sites. Scarce or no plasma concentrations were observed for the 0.04 and 0.004 divided SC doses.

Conclusion: In this single male and female Gottingen minipig study, salmeterol appeared to be well absorbed after subcutaneous administration at a single site and after divided SC administration at 5 sites at the 4 µg/kg dose and after divided SC administration of the 0.4 µg/kg dose. Overall there were no consistent, substantial differences in Cmax and $AUC_{inf}$ values between single site SC doses vs. multiple site SC doses. Overall there were no substantial differences in pharmacokinetic parameters between the male and female animals.

Example 2

Plasma Pharmacokinetics Following a Single Intravenous and Subcutaneous Injection of a Combination of Formoterol and Budesonide in Gottingen Minipigs Materials and Methods: Formoterol fumarate dehydrate and budesonide were formulated in 2% PEG-400 in saline. 1 male and 1 female non-naive Gottingen minipigs (8 to 12 kg upon receipt per protocol) were utilized. The animals were housed individually. The dosing scheme is shown in Table 4 below:

| Injection # | Route | Dose (µg/kg) Budesonide | Formoterol | No. Animals/sex |
|---|---|---|---|---|
| 1 | IV | 1.6 | 0.4 | 1 |
| 2 | SC | 1.6 | 0.4 | 1 |
| 3 | SC* | 1.6 | 0.4 | 1 |

*The dose volume was equally divided over 5 injection sites

Each minipig received a single IV injection of the combined formoterol and budesonide formulation followed by testing of the SC doses. Each dose was separated by at least a 3-day washout period. The IV dose was administered by slow bolus (1 minute; 0.017 hr) into the marginal ear vein, whereas the first SC dose was administered as a bolus injection along the back (neck-region) where there was a longitudinal fat depot. The second SC dose was distributed in 5 separate proximal SC injections separated by approximately 2 cm. Blood samples (approximately 4 mL) were collected via the branchiocephalic plexus at pre-dose and at 2, 5, 10, 20, 30 and 45 minutes, and at 1, 2, 4, 8 and 24 hr post-dose. Blood samples were placed in tubes containing $K_2$-EDTA as the anticoagulant. Samples were processed to plasma by centrifugation and stored frozen at approximately −70° C. (+/− 15° C.) until shipment for analysis.

Sample Analysis: Plasma samples were analyzed for formoterol and budesonide using a qualified liquid chromatography/mass spectrometry/mass mass spectrometry (LC/MS/MS) method. The lower limit of quantitation (LLOQ) was 1.00 pg/mL for formoterol and 25.0 pg/mL for budesonide.

Data Analysis: Non-compartmental pharmacokinetic parameters were calculated using WinNonlin 5.2 software, NCA model 202, IV infusion input for the IV data and NCA model 200, extravascular input for the SC data. Individual plasma concentrations for each animal were used in the calculation of pharmacokinetic parameters. Nominal collection times and doses were used in the calculations. The area under the plasma concentration-time curve (AUC) was calculated using linear trapezoidal approximation (linear/log interpolation). Concentration values below the assay limit of quantitation were set to zero for calculations. The maximum plasma concentration ($C_{max}$) and the time of its occurrence ($T_{max}$) were verified by inspection. The half-life ($t_{1/2}$) values were calculated using the last 3 plasma concentrations with non-zero values, if data permitted.

Results: The pharmacokinetic parameters are shown in Table 5. The plasma concentrations of formoterol and budesonide are shown in Table 6 and FIG. 1. The pre-dose period 1 IV sample of male animal 1-0771 showed a low, but measurable budesonide concentration and the pre-dose period 1 IV sample of female animal 2-0623 showed a low, but measurable formoterol concentration. Other occasional measurable pre-dose concentrations of formoterol or budesonide are explainable as carryover from previous doses. Actual sampling times differed from nominal sampling times on occasion by more than 10%. Data in the apparent elimination phase were inadequate to estimate the $t_{1/2}$ for the male animal 1-0771 for the SC1 group for budesonide.

TABLE 5

Pharmacokinetic Parameters for Formoterol and Budesonide Following IV
and SC Administration of the Combination to Gottingen Minipigs (08-522)

| Analyte | Route | Sex | Animal | $T_{max}$ (hr) | $C_{max}$ (pg/mL) | $AUC_{inf}$ (pg·hr/mL) | $t_{1/2}$ (hr) | $t_{last}$ (hr) | CL (mL/hr/kg) | $V_{ss}$ (mL/kg) |
|---|---|---|---|---|---|---|---|---|---|---|
| Formoterol | IV | Male | 1-0771 | 0.0333 | 410 | 264 | 2.54 | 8.00 | 1520 | 3940 |
| Formoterol | IV | Female | 2-0623 | 0.0333 | 900 | 328 | 2.86 | 8.00 | 1220 | 3170 |
| Budesonide | IV | Male | 1-0771 | 0.0333 | 760 | 781 | 2.73 | 4.00 | 2050 | 6290 |
| Budesonide | IV | Female | 2-0623 | 0.0333 | 1350 | 764 | 1.61 | 4.00 | 2090 | 3380 |

| Analyte | Route | Sex | Animal | $T_{max}$ (hr) | $C_{max}$ (pg/mL) | $AUC_{inf}$ (pg·hr/mL) | $t_{1/2}$ (hr) | $t_{last}$ (hr) | F |
|---|---|---|---|---|---|---|---|---|---|
| Formoterol | SC1 | Male | 1-0771 | 0.0333 | 378 | 627 | 5.51 | 24.0 | 2.38 |
| Formoterol | SC5 | Male | 1-0771 | 0.167 | 217 | 579 | 4.19 | 24.0 | 2.19 |
| Formoterol | SC1 | Female | 2-0623 | 0.0833 | 284 | 378 | 2.33 | 8.00 | 1.15 |
| Formoterol | SC5 | Female | 2-0623 | 0.0833 | 256 | 577 | 12.8 | 24.0 | 1.76 |
| Budesonide | SC1 | Male | 1-0771 | 0.0833 | 979 | 2020 | 18.8 | 24.0 | 2.59 |
| Budesonide | SC5 | Male | 1-0771 | 0.0833 | 1060 | 981 | 1.01 | 4.00 | 1.26 |
| Budesonide | SC1 | Female | 2-0623 | 0.167 | 798 | 992 | 1.41 | 4.00 | 1.30 |
| Budesonide | SC5 | Female | 2-0623 | 0.333 | 697 | 884 | 1.03 | 4.00 | 1.16 |

$AUC_{inf}$ = area under the curve at infinite time. CL = plasma clearance. F = bioavailability. SC1 = single site SC injection; SC5 = SC injection split among 5 sites. $t_{last}$ = time of last measurable plasma concentration. $V_{ss}$ = volume of distribution at steady state.

TABLE 6

Plasma Concentrations of Formoterol and Budesonide Following IV and
SC Administration of the Combination to Gottingen Minipigs (08-522)

| Route | Animal | Sex | 0 | 0.0333 | 0.0833 | 0.167 | 0.333 | 0.500 | 0.750 | 1.00 | 2.00 | 4.00 | 8.00 | 24.0 |
|---|---|---|---|---|---|---|---|---|---|---|---|---|---|---|
| | | | | | | Formoterol | | | | | | | | |
| IV | 1-0771 | Male | <LLOQ | 410 | 99.6 | 90.2 | 68.9 | 57.0 | 48.8 | 81.3 | 26.5 | 18.3 | 5.33 | <LLOQ |
| SC1 | 1-0771 | Male | 4.63 | 378 | 294 | 147 | 121 | 161 | 79.0 | 83.3 | 82.2 | 42.2 | 15.2 | 2.87 |
| SC5 | 1-0771 | Male | <LLOQ | 133 | 216 | 217 | 150 | 93.8 | 94.1 | 80.1 | 71.1 | 35.9 | 18.1 | 1.30 |
| IV | 2-0623 | Female | 3.53 | 900 | 204 | 110 | 73.5 | 98.4 | 61.4 | 45.4 | 31.3 | 18.4 | 7.26 | <LLOQ |
| SC1 | 2-0623 | Female | <LLOQ | 169 | 284 | 237 | 156 | 127 | 78.9 | 67.8 | 51.2 | 28.5 | 8.58 | <LLOQ |
| SC5 | 2-0623 | Female | <LLOQ | 94.6 | 256 | 178 | 131 | 100 | 82.6 | 62.8 | 44.4 | 26.0 | 10.3 | 6.95 |
| | | | | | | Budesonide | | | | | | | | |
| IV | 1-0771 | Male | 41.9 | 760 | 539 | 499 | 356 | 308 | 204 | 138 | 60.5 | 57.5 | <LLOQ | <LLOQ |
| SC1 | 1-0771 | Male | <LLOQ | 806 | 979 | 903 | 703 | 466 | 285 | 222 | 97.9 | 43.2 | <LLOQ | 31.6 |
| SC5 | 1-0771 | Male | <LLOQ | 902 | 1060 | 933 | 647 | 538 | 438 | 317 | 92.4 | 36.5 | <LLOQ | <LLOQ |
| IV | 2-0623 | Female | <LLOQ | 1350 | 939 | 592 | 335 | 307 | 285 | 169 | 69.8 | 42.4 | <LLOQ | <LLOQ |
| SC1 | 2-0623 | Female | <LLOQ | 250 | 559 | 798 | 784 | 598 | 431 | 238 | 117 | 51.9 | <LLOQ | <LLOQ |
| SC5 | 2-0623 | Female | <LLOQ | 249 | 637 | 434 | 697 | 535 | 382 | 328 | 100 | 39.5 | <LLOQ | <LLOQ |

Plasma concentrations are reported in pg/mL. LLOQ = 1.00 pg/mL for formoterol and 25.0 pg/mL for budesonide SC1 = single site SC injections; SC5 = SC injection split among 5 sites.

Overall there were no consistent, substantial differences in $C_{max}$ or $AUC_{inf}$ values between the male and female animal for formoterol or budesonide. Additionally, there were no consistent, substantial differences in $C_{max}$ and $AUC_{inf}$ values for formoterol or budesonide between single site SC doses and multiple (5) site SC doses. Both formoterol and budesonide appeared to be well absorbed after SC administration at a single site and after divided SC administration at 5 sites; however, bioavailability was likely poorly estimated due to scarcity of data in the apparent terminal elimination phase to calculate the apparent terminal elimination rate constant This affected calculation of $AUC_{inf}$, $t_{1/2}$, CL, $V_{ss}$, and F.

Conclusion: In this single male and female Gottingen minipig study, both formoterol and budesonide appeared to be well absorbed after subcutaneous administration at a single site and after divided SC administration at 5 sites at the 4 μg/kg dose and after divided SC administration of the 0.4 μg/kg dose. Overall there were no consistent, substantial differences in Cmax and $AUC_{inf}$ values between single site SC doses vs. multiple site SC doses. Overall there were no substantial differences in pharmacokinetic parameters between the male and female animals.

Example 3

Clinical Trials

Example 3A

Figure 2A:
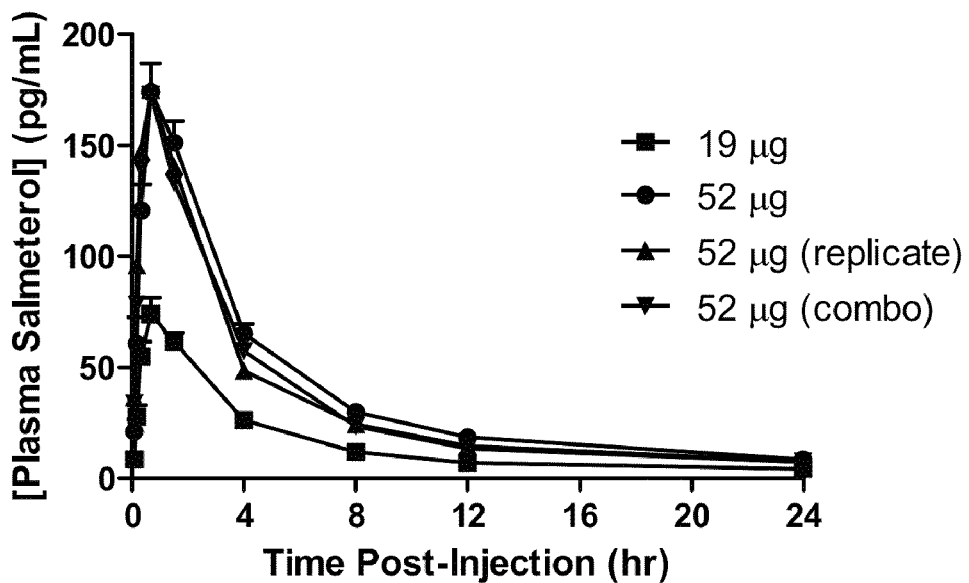
FIG. 2A is illustrative of the plasma concentrations of two different concentrations of salmeterol xinafoate as well as a combination of salmeterol xinafoate and fluticasone propionate following subcutaneous administration to subjects.
Figure 2B:
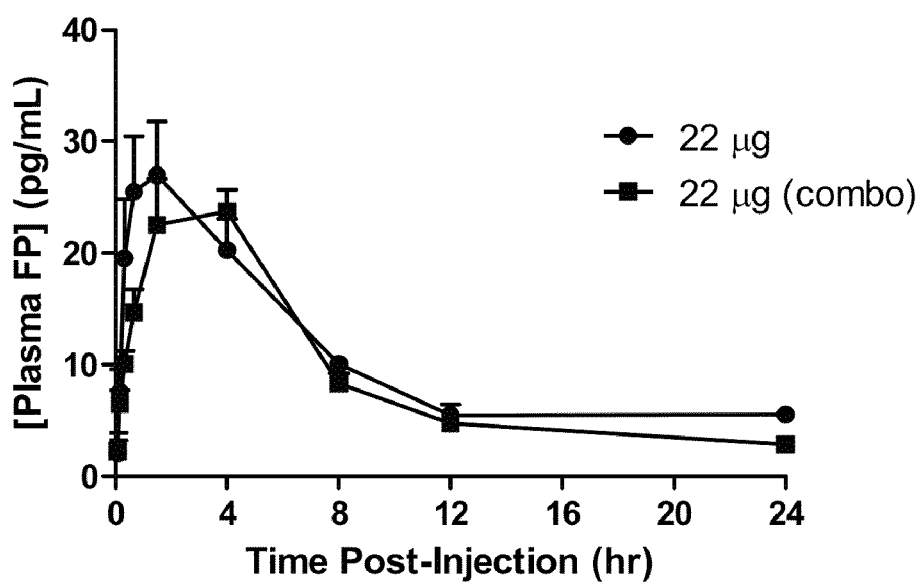
FIG. 2B is illustrative of the plasma concentration of fluticasone propionate and a combination of fluticasone propionate and salmeterol xinafoate following subcutaneous administration to subjects.

Phase 1—Open-Label Evaluation of the
Pharmacokinetics and Safety of Salmeterol
Xinafoate and Fluticasone Propionate
Co-Administered Subcutaneously in Healthy
Volunteers Objectives: To evaluate the pharmacokinetics and safety of increasing single doses of salmeterol xinafoate (SX) administered by subcutaneous injection to healthy volunteers (HV). To also evaluate the pharmacokinetics and safety of a single dose of fluticasone propionate (FP) administered by subcutaneous injection to healthy volunteers whereby the single dose of FP yields a mean systemic $C_{max}$ not exceeding 100 pg/mL. The objective of this study is to also evaluate the pharmacokinetics and safety of a single dose of the selected SX dose and selected FP dose co-administered as a single subcutaneous injection to healthy volunteers. Additionally, the objective of this study is to evaluate the pharmacokinetics and safety following multiple doses of the selected SX+FP combined dose administered by subcutaneous injection to healthy volunteers (either 1 time per week for 4 weeks or 3 times per week for 4 weeks).

Study Design: Part I: An open-label, sequential dose-escalation pharmacokinetic study of single doses of SX administered subcutaneously in ten (10) healthy volunteers. Part II: An open-label, fixed sequence, cross-over pharmacokinetic study to investigate potential interactions between the selected FP dose and the selected SX dose administered subcutaneously in eight (8) healthy volunteers. Part III: An open-label, multiple-dose pharmacokinetic study of the selected SX+FP combined dose administered subcutaneously either 1 time per week for 4 weeks or 3 times per week for 4 weeks in twelve (12) healthy volunteers.

Study Drug: A 400 μg/mL sterile, preservative-free, clear, aqueous solution for injection of SX is contained in a 5 mL single-use glass vial. Each 5 mL single-use glass vial contains 2.6 mL of SX solution (400 μg/mL) which is stored frozen (−15° C. to −25° C.) and protected from light until dose preparation. A 25 mg/mL sterile, preservative free, clear, aqueous solution for injection of FP is contained in a 2 mL single-use glass vial. Each 2 mL single-use glass vial contains 1.0 mL of FP solution (25 μg/mL) which is stored frozen (−15° C. to −25° C.) and protected from light until dose preparation. Diluent: A sterile, preservative free, clear, aqueous solution of 20% PEG 400, 1% polysorbate 80, and sterile water for injection contained in a 10 mL single-use glass vial. Each 10 mL single-use glass vial contains 5.0 mL of diluent solution which should be stored at room temperature (15° C. to 25° C.). Prior to administration, the drug products are thawed, mixed, and if necessary diluted with sterile diluent to provide the target concentrations for dose administration. Study drug is subcutaneously administered to subjects using a sterile, disposable single-use syringe with an appropriate gauge needle. Instructions for study drug storage, preparation, and administration comply with <USP> 797 guidance for Compounding Sterile Preparations.

Study Population: Healthy male and female subjects, 18 to 55 years of age.

Inclusion Criteria:

a. Male and female subjects, 18 to 55 years of age, in good health and free of any disease or physical condition which might, in the investigator's opinion, expose the subject to an unacceptable risk by study participation;
b. Written, informed consent prior to any study procedures (including screening) being performed;
c. BMI≧18 kg/$m^2$ and ≦30 kg/$m^2$;
d. Minimum 2 cm abdominal skin fold on vertical pinch 2 cm lateral to umbilicus as determined by the site using Accu-Measure calipers;
e. History of a stable exercise routine over the last 3 months or a sedentary lifestyle (less than 60 minutes of exercise per week);
f. Agreement to adhere to the study requirements and restrictions including all required assessments and visits.

Exclusion Criteria:

a. Women of childbearing potential who are pregnant, lactating, and/or who are not using adequate birth control methods;
b. Known hypersensitivity to the study drugs or any of their components;
c. Deemed by the investigator to be unreliable and unlikely to comply with protocol procedures or adhere to the study visit schedule;
d. Any medical condition that in the opinion of the investigator might jeopardize the subject's safety or interfere with the absorption, distribution, metabolism, or excretion of the study drug, including:
   i. Major surgery within 30 days prior to day 0 or planned surgery during the study period;
   ii. Seropositive for HIV, hepatitis B surface antigen or hepatitis C, or previously diagnosed disease(s) of immune function where absolute neutrophil count <1000 $mm^3$;
   iii. Any clinically significant abnormal laboratory, ECG (including cardiac arrhythmia) and/or physical exam findings during screening and/or day 0;
   iv. Skin disease or any other condition which is the opinion of the investigator might interfere with clinical assessment of the injection site area at screening or day 1;
   v. Hemoglobin level below 12 g/dL at screening;
   vi. History of diabetes mellitus or cardiovascular disease (subjects with well-controlled hypertension will not be excluded);
   vii. A consistently abnormal pulse rate, abnormal resting supine blood pressure, and/or a predisposition to orthostatic hypotension if considered clinically significant;
e. Recent history of drug or alcohol abuse within 90 days prior to screening;
f. Use of any tobacco products within 90 days prior to screening;
g. Donation of blood/plasma and/or any significant blood loss for any reason greater than 450 mL with 60 days prior to screening;
h. Use of tricyclic antidepressants or monoamine oxidase inhibitors medications within 14 days prior to day 0 or during the study;
i. Other exclusion criteria such as use of other systemic prescription medications, use of any oral herbal or dietary supplement, use of alcohol-, caffeine-, or xanthine-containing products.

Pharmacokinetic Parameters: The following parameters will be measured/determined: $AUC_{0-t}$, $AUC_{0-inf}$, $C_{max}$, $T_{max}$, $k_{el}$, $A_{UCt/inf}$, and $t_{1/2el}$.

Results—Single dose Pharmacokinetics: FIG. 2A shows the plasma concentration of 2 doses of salmeterol xinafoate (19 μg and 52 μg) following a 1 mL subcutaneous injection into abdominal fat of a group of 10 subjects. Plasma concentration of salmeterol xinafoate (52 μg) following a 1 mL subcutaneous injection into abdominal fat of a second group of 8 subjects is also shown in FIG. 2A. This group of subjects also received a 1 mL subcutaneous injection of fluticasone propionate (22 μg) (FIG. 2B). Finally, this group of 8 subjects received a 1 mL subcutaneous injection of a combination of salmeterol xinafoate (52 μg) and fluticasone propionate (22 μg) into abdominal fat; the plasma concentrations of each are shown in FIGS. 2A and 2B (combo).

Results—Multiple dose Pharmacokinetics: FIG. 2A shows the pharmacokinetic profile for 52 μg of salmeterol xinafoate administered to the patient group that received 1 subcutaneous injection per week for 4 consecutive weeks. FIG. 2B shows the pharmacokinetic profile for 22 μg of fluticasone propionate administered to the patient group that received 1 subcutaneous injection per week for 4 consecutive weeks. The profiles demonstrate that the systemic exposure limits for salmeterol xinafoate and fluticasone propionate will not exceed those of the commercially available ADVAIR DISKUS® 500/50 drug product. Each profile depicted in FIGS. 2A and 2B demonstrates an increase in Cmax and AUC at day 22 compared to day 1, which is suggestive of tissue remodeling (based on a reduced amount of adipose tissue at day 22).

Results—Safety Assessments: No serious adverse events were observed in the patients studied. Specifically, no adverse cardiovascular events were observed and no significant skin changes (e.g., atrophy, pigmentation, nodularity, or necrosis) were observed. Only minimal skin reactions (transient pain and irritation) were observed.

Example 3B

Phase 2a—A Dose-Ranging Frequency Evaluation of the Safety and Efficacy of Salmeterol Xinafoate and Fluticasone Propionate Co-Administered for Subcutaneous Injection for the Reduction of Abdominal Subcutaneous Adipose Tissue Objectives: To evaluate in a single masked, placebo-controlled design, the safety and exploratory efficacy measures of subcutaneous injections of three different doses of the combination of salmeterol xinafoate (SX) and fluticasone propionate (FP) administered by subcutaneous injection 1 or 2 times per week for 4 weeks to subjects with measurable abdominal subcutaneous adipose tissue.

Study Design: A single-masked, placebo-controlled multiple-dose study of the safety and efficacy of three different doses of the combination of salmeterol xinafoate (SX) and fluticasone propionate (FP) administered by subcutaneous injection 1 or 2 times per week for 4 weeks in 60 subjects with measurable abdominal subcutaneous adipose tissue. The three selected doses were chosen to yield a systemic exposure ranging from approximately 10-fold to 100-fold lower than the reference-listed ADVAIR DISKUS® 500/50 drug product.

Study Drug—Active Ingredient: A 400 μg/mL sterile, preservative-free, clear, aqueous solution for injection of SX is contained in a 5 mL single-use glass vial. Each 5 mL single-use glass vial contains 2.6 mL of SX solution (400 μg/mL) which is stored frozen (−15° C. or below) and protected from light until dose preparation. A 25 mg/mL sterile, preservative free, clear, aqueous solution for injection of FP is contained in a 2 mL single-use glass vial. Each 2 mL clear glass vial contains 1.0 mL of FP solution (25 μg/mL) which is stored frozen (−15° C. or below) and protected from light until dose preparation. Diluent: A sterile, preservative free, clear, aqueous solution of 20% PEG 400, 1% polysorbate 80, and sterile water for injection contained in a 10 mL clear glass vial. Each 10 mL single-use glass vial contains 5.0 mL of diluent solution which should be stored at room temperature (15° C. to 25° C.). Diluent or a version of the Diluent further diluted with sterile water for injection (SWFI) served as the placebo.

The supplies are provided in nested bulk packaging. Prior to administration, the drug products will be thawed, mixed, and if necessary, diluted under ascetic conditions with sterile Diluent or sterile water for injection to provide the target concentrations for dose administration. Study drug a placebo will be administered subcutaneously at the marked injection sites using a sterile, disposable single-use appropriately sized Luer Lock syringe with a 30 gauge 0.5 inch needle.

Treatment Cohorts: A single-masked, multiple-dose study of different doses and dosing frequencies of SX and FP injected subcutaneously on one side of the abdomen 1 or 2 times per week for 4 weeks to subjects with measurable abdominal subcutaneous adipose tissue. Placebo injections on the contra-lateral side of the abdomen will serve as control. The SX and FP dose will be administered as 1 mL injections 1 or 2 times per week to the injection site, either on the right or left of the umbilicus according to randomization. The corresponding control injection site on the contra-lateral side of the umbilicus will be injected with 1 mL of placebo in the identical sequence on the designated injection days. The sequence of injections will continue until for 4 consecutive weeks for a total of 4 or 8 subcutaneous injections of study drug and 4 or 8 subcutaneous injections of placebo, depending on randomization. Comprehensive safety assessments will be performed at each subject visit through the end of the study at week 8. Eligible subjects will be randomized to one of the following six treatment cohorts (n=10 per group) for the 4 consecutive week treatment period.

1.0 μg FP and 0.5 μg SX and placebo injections once or twice per week 1.0 μg FP and 5.0 μg SX and placebo injections once or twice per week 1.0 μg FP and 10.0 μg SX and placebo injections once or twice per week Duration of Treatment: The study duration lasted 8 weeks: 4 week treatment period followed by 1 week and 4 week post-therapy assessment follow-up visit for safety and efficacy.

Study Population: Healthy male and female subjects, 18 to 55 years of age. A total number of 60 subjects will be enrolled into 6 treatment cohorts. Subjects who provided informed consent in writing but who do not receive study drug for any reason will be considered screen failures and will be replaced.

Inclusion Criteria:
a. Male and female subjects, 18 to 55 years of age, in good health and free of any disease or physical condition which might, in the investigator's opinion, expose the subject to an unacceptable risk by study participation;
b. Anterior abdominal skin fold thickness of between 30 mm to 50 mm, inclusive, at 2 cm to the right and left of the umbilicus measured with pinch calipers at screening day 0, and a subcutaneous adipose tissue thickness of greater than or equal to 2.5 cm and less than or equal to 5.0 cm on 2-dimensional ultrasound at day 0;
c. BMI greater than or equal to 22 kg/m$^2$ and less than or equal to 30 kg/m$^2$ and a history of stable weight in the last 3 months at screening;
d. History of stable exercise routine over the last 3 months (at least 120 minutes per week of moderate exercise, e.g., brisk walking) at screening;
e. Written, informed consent prior to any study procedures (including pre-treatment and screening) being performed; agreement to adhere to the study requirements and restrictions including all required assessments and visits.

Exclusion Criteria:
a. Women of childbearing potential who are pregnant, lactating, and/or who are not using adequate birth control methods;
b. Known hypersensitivity to the study drugs or any of their components;

c. Deemed by the investigator to be unreliable and unlikely to comply with protocol procedures or adhere to the study visit schedule;

d. Any medical condition that in the opinion of the investigator might jeopardize the subject's safety or interfere with the absorption, distribution, metabolism, or excretion of the study drug, including:

i. Major surgery within 30 days prior to day 0 or planned surgery during the study period;

ii. Any clinically significant abnormal laboratory result at screening;

iii. Skin disease or any other conditions in the area of injection sites at screening or day 0 which in the opinion of the investigator might interfere with clinical assessment of the injection site area;

iv. History of diabetes or cardiovascular disease (subjects with well-controlled hypertension will not be excluded);

v. An abnormal pulse rate, abnormal resting supine blood pressure, and/or a predisposition to orthostatic hypotension if considered clinically significant;

e. Recent history of drug or alcohol abuse within 90 days prior to screening;

f. Donation of blood/plasma and/or any significant blood loss for any reason greater than 450 mL with 60 days prior to screening (or during study period);

g. Prior enrollment in any SX and FP for injection study;

h. Concurrent enrollment in another investigational drug or device study; or use of any experimental or investigational drug or device within 30 days, or for drugs within 6 times the elimination half-life prior to day 0 if that is longer;

i. Use of systemic, inhaled, or topical corticosteroids, immunodulators, anti-metabolites, beta 2-andrenergic receptor agonists, beta 2-andrenergic receptor blockers, or nonpotassium-sparing diuretics within 28 days prior to day 0, or during the study;

j. Use of tricyclic antidepressants or monoamine oxidase inhibitor medications within 14 days prior to day 0, or during the study.

Efficacy Assessments: Assessments include (a) abdominal subcutaneous adipose tissue layer thickness using 2-diminseional ultrasound; (b) abdominal skin fold thickness measurements using commercial pinch calipers to measure the vertical skin folds directly over the separate injection sites (2 cm to the right and left of the umbilicus); and (c) waist measurements taken at the level of the umbilicus/injection sites.

(a) 2-Dimensional Ultrasound

Procedure: Ultrasound assessment of the designated injection sites (2 cm to the right and left of the umbilicus) were undertaken at specified time points. All study ultrasound recordings were performed using the same model of ultrasound machine and the same probe (a 12 MHz linear probe). Ultrasound gel was applied to the skin, and the thickness of the gel was sufficient to obtain a clear image without applying pressure to the skin. To ensure valid capture data, the B-mode image was used to aid the capture process to obtain good image quality. The ultrasound transducer was held vertical to the skin and using the skin markings for guidance, gently positioned in the sagittal plane with the mid-point of the transducer immediately above the marked injection site (bilateral sites on the right and left of the umbilicus). The transducer was held vertical to the skin (at an angle incidence of 90°), the ultrasonographer used digital calipers positioned in the center of the scan image and clicked on the pixel that marks the skin surface and the pixel represents the fat-fascial boundary. The distance between the pixels was recorded as the subcutaneous adipose tissue layer thickness. All images were produced by the same ultrasonographer. The change in mean subcutis thickness (in cm) from baseline as determined using 2D-ultrasound was measured at 4 weeks, 5 weeks, and 8 weeks from the first day of treatment.

(b) Abdominal Skin Fold Measurement

Procedure: Abdominal skin fold measurements utilizing a commercially available pinch caliper were used per manufacturer instructions included with the caliper device. Abdominal skin fold measurements were made by vertical pinch 2 cm lateral to the umbilicus at screening day and day 0 to confirm subject eligibility. Abdominal skin fold measurements were also performed throughout the study at specified times. Abdominal skin fold thickness measurements were taken directly over the separate injection sites (2 cm to the right and left of the umbilicus). Measurements at the injection sites were compared against baseline. Contra-lateral control area was also used to confirm that body fat remains relatively stable over the study duration.

(c) Waist Measurements

Procedure: Measurements of waist were taken at specified time points. At day 0 when the injection sites were marked, the tip of the spinous process of the corresponding lumbar vertebra at the level of the umbilicus were also marked. Waist measurements were taken at the level of the umbilicus in line with the two marked injection sites, and the posterior mark over the lumbar vertebral spinous process. The full waist circumference, and the right and the left hemi-circumferences were recorded.

Figure 3A:
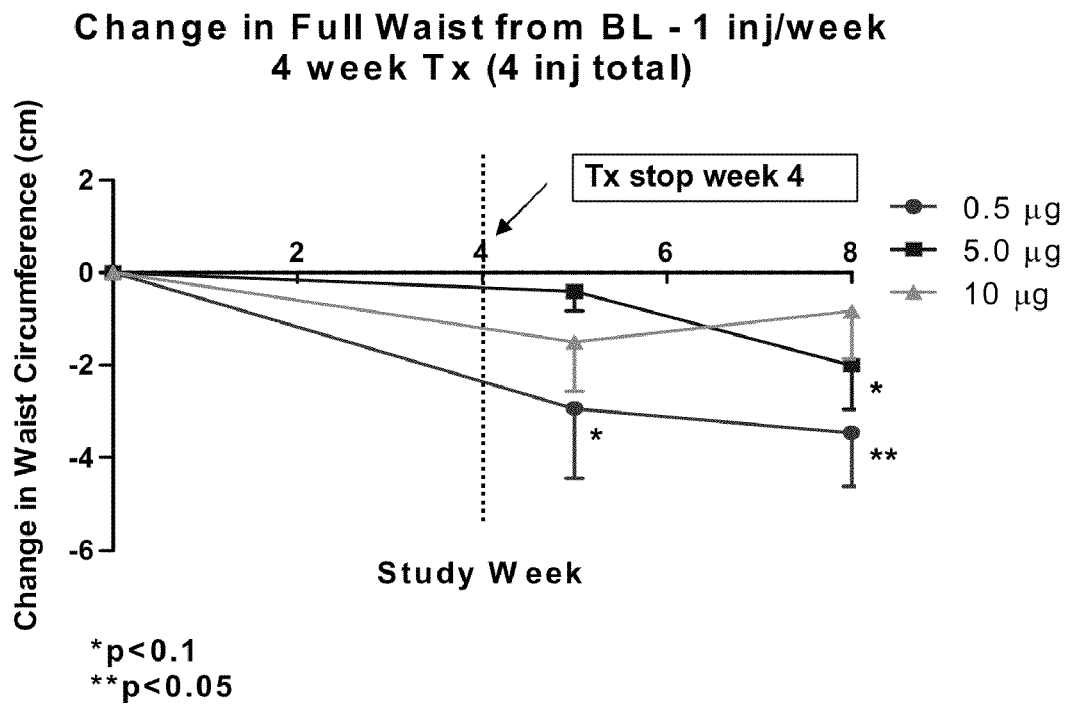
FIG. 3A is illustrative of the change in full waist circumference from baseline over an 8 week period in human patients in the following treatment groups: (1) 0.5 µg of salmeterol and 1 µg of fluticasone once per week for four weeks; (2) 5.0 µg of salmeterol and 1 µg of fluticasone once per week for four weeks; and (3) 10 µg of salmeterol and 1 µg of fluticasone once per week for four weeks.
Figure 3B:
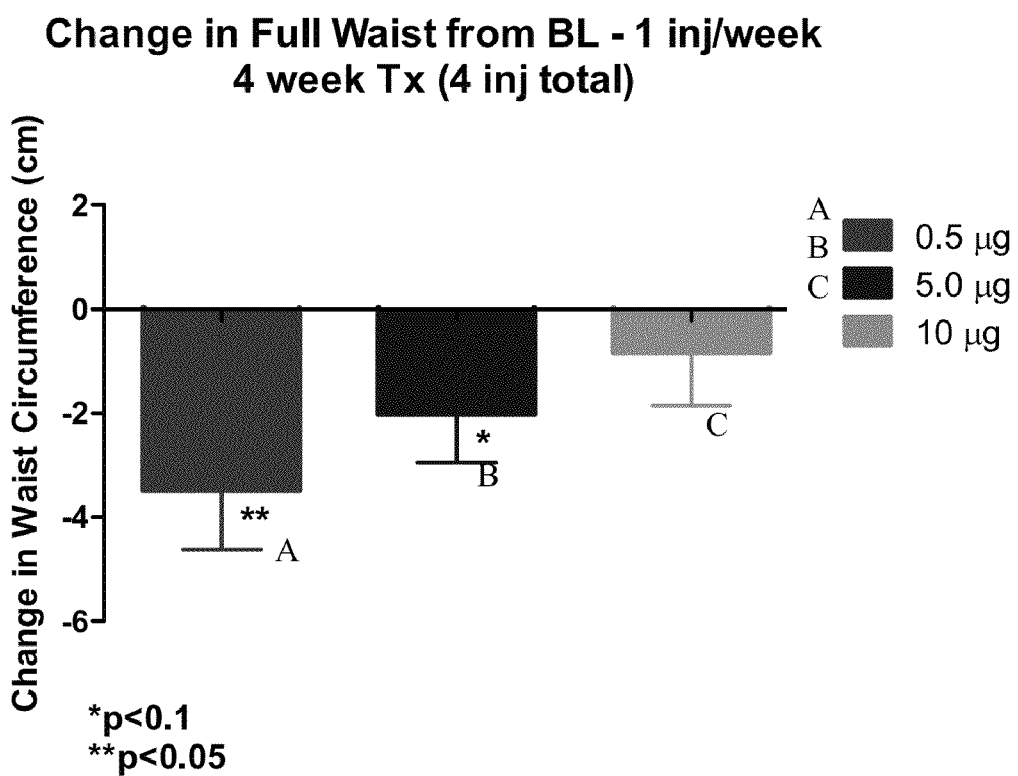
FIG. 3B is illustrative of the change in full waist circumference from baseline in human patients after 8 weeks of treatment in the following treatment groups: (1) 0.5 µg of salmeterol and 1 µg of fluticasone once per week for four weeks; (2) 5.0 µg of salmeterol and 1 µg of fluticasone once per week for four weeks; and (3) 10 µg of salmeterol and 1 µg of fluticasone once per week for four weeks.

Results: FIG. 3A shows the mean change in full waist circumference from baseline over an 8 week period at specified time points in all patients receiving one injection per week of test drug for 4 weeks. FIG. 3B shows the mean change in full waist circumference from baseline in these patients after 8 weeks. FIGS. 3A and 3B demonstrate a dose-related treatment effect with the group of patients receiving the 0.5 µg of salmeterol xinafoate and 1 µg of fluticasone propionate once per week for four weeks evidencing a change in waist circumference of about 3.5 cm at 8 weeks. Thus, the greatest change in full waist circumference was evidenced by the patients receiving the least amount of active ingredient.

FIG. 4 demonstrates a weekly total dose-therapeutic efficacy response curve (based on change in waist circumference) for salmeterol xinafoate. The weekly dose with the greatest therapeutic efficacy was evidenced in patients who received the lowest dose of 0.5 µg of salmeterol xinafoate at the lowest frequency (once per week for 4 weeks).

FIG. 8 demonstrates that the patients evidenced no significant change in mean weight during 8 weeks of study.

Safety Assessments: Safety assessments were conducted at all time points. No serious adverse events were observed in patients studied. Specifically, no adverse cardiovascular events were observed, and no significant skin changes (e.g., atrophy, pigmentation, nodularity, or necrosis) were observed. Only minimal skin reactions (transient pain and irritation) were observed.

Example 3C

Phase 2—A Double-Masked Evaluation of the Safety and Efficacy of Salmeterol Xinafoate and Fluticasone Propionate Co-Administered for Subcutaneous Injection for the Reduction of Subcutaneous Abdominal Adiposity Objectives: A Phase 2 study to examine the potential of selected doses of salmeterol xinafoate (SX) and fluticasone propionate (FP) co-administered to reduce abdominal subcutaneous adipose tissue, which is an interim surrogate to guide studies in subjects with symptomatic exophthalmos associated with thyroid-related eye disease (TED). The study also evaluated the safety and efficacy of subcutaneous injections of salmeterol xinafoate (SX) and fluticasone propionate (FP) for the reduction of abdominal (peri- and infra-umbilical) adiposity. The study compared the efficacy and safety of salmeterol xinafoate (SX) and fluticasone propionate (FP) at 1.0 µg FP and 0.05 µg SX once weekly to 1 mL placebo once weekly for 8 weeks for the reduction of measurable, abdominal subcutaneous adipose tissue. Additionally, the study evaluated in a double-masked, placebo-controlled design, the pharmacokinetics following multiple injected doses of salmeterol xinafoate (SX) and fluticasone propionate (FP) once weekly for 8 weeks. Other objectives of the study included exploration of a number of secondary efficacy endpoints, and evaluation of potential biomarkers.

Study Design: A double-masked, multiple-dose study of the safety and efficacy of 0.05/1.0 or 0.5/1.0 µg/mL doses of salmeterol xinafoate (SX) and fluticasone propionate (FP) compared to placebo administered as twenty two 1 mL regional subcutaneous injections once a week for 8 weeks in 60 subjects with measurable abdominal subcutaneous adipose tissue.

Study Drug—Active Ingredient: A 400 µg/mL sterile, preservative-free, clear, aqueous solution for injection of SX is contained in a 5 mL single-use glass vial. Each 5 mL single-use glass vial contains 2.6 mL of SX solution (of 400 µg/mL). A 25 mg/mL sterile, preservative free, clear, aqueous solution for injection of FP is contained in a 2 mL single-use glass vial. Each 2 mL clear glass vial contains 1.0 mL of FP solution (25 mg/mL). Immediately prior to administration, a volume of SX (2.6 mL fill of 400 µg/mL in a 5.0 mL vial) was mixed with FP (1.0 mL fill of 25 mg/mL in a 5.0 mL vial). The SX and FP should be stored frozen (−15° C. or below) and protected from light until dose preparation. The mixed SX and FP should be protected form light until administration. The SX and FP drug products are provided in nested drug packaging.

Placebo—Sterile saline, USP (0.9% sodium chloride) was used as the placebo.

The mixed SX and FP combination and placebo was administered as twenty-two 1 mL (for a total volume of 22 mL) into the abdominal subcutaneous adipose tissue using a sterile, disposable, syringe with 27 gauge and 3/8 inch needle.

Treatment Groups: Eligible subjects in this multiple dose study were randomized in a 1:1:1 ratio to receive twenty-two 1 mL subcutaneous injections of either 1.0 µg/mL of FP+0.05 µg/mL SX or 1.0 µg/mL of FP+0.5 µg/mL SX or placebo. The twenty-two subcutaneous injections were spaced 4 cm apart and treated a pre-marked midline abdominal area of adiposity that was approximately 16×14 cm². The sequence of once weekly subcutaneous injections continued for 8 consecutive weeks for a total of 176 injections administered into the marked abdominal area. Comprehensive safety assessments were performed at each subject visit through the end of study on day 57+/−2 days.

Duration of Treatment: The screening period lasted 30 days. The expected study duration was 9 weeks: 8 weeks of a treatment period and 1 week post-therapy follow-up visit for assessment of safety and efficacy.

Study Population: Qualified male and female patients, 18 to 65 years of age, inclusive. A qualified subject had a localized, measurable abdominal subcutaneous adipose tissue that was reported to be exercise-resistant and diet-resistant.

Inclusion Criteria:
a. Male and female subjects, 18 to 55 years of age, having provided informed written consent;
b. Subjects reporting dissatisfaction with their abdominal (peri and infra-umbilical) subcutaneous adipose tissue, or who are considering, or are in the process of seeking cosmetic reduction of their abdominal adiposity;
c. BMI greater than or equal to 18.5 kg/m² and less than or equal to 28 kg/m² and a history of stable weight in the last 3 months, and a variance of less than or equal to 5% between screening at day 1.
d. History of a stable diet and exercise routine in the 3 months prior to screening, and a willingness to adhere strictly to this established routine during the period of study;
e. Female subjects who have a negative urine pregnancy test at screening and day 1, and who agree to use adequate birth control methods (abstinence, female partner, stabilized on oral contraceptives for at least 2 months, implant, injection, IUD, patch, NuvaRing®, condom and spermicidal, diaphragm and spermicidal) throughout the study until completion of post-treatment procedures for all.

Exclusion Criteria:
a. Females who are pregnant, lactating, and/or who are childbearing but are not using adequate birth control methods;
b. Female subjects who are not within 12 months post-partum;
c. History of treatment of abdominal subcutaneous adipose tissue including procedures (e.g. caesarean section, abdominoplasty, liposuction), ablative contouring devices, mesotherapy or lipolytic agents;
d. Subjects planning to embark on a weight loss or exercise program during participation;
e. Subjects who partake of abdominal massaging and who are unwilling to this therapy during the study;
f. Known hypersensitivity to the study drugs and/or any of their components;
g. Prior or current enrollment in any Lithera study;
h. Concurrent enrollment in another investigational drug or device study; or experimental or investigational drug or device within 30 days, or for drugs times the elimination half-life prior to day 1 if that is longer;
i. Any medical condition that in the opinion of the investigator might jeopardize subject's safety or complicate study procedures or assessments, including, but not limited to:
  i. any bleeding, or connective tissue disorders;
  ii. diabetes (Type I and II) or cardiovascular disease (subjects with well-hypertension will not be excluded);
  iii. history of major surgery within 30 days prior to day 1, or planned surgery during the study period;
  iv. any clinically-significant physical exam findings, as determined by the investigator, at Screening or day 1;
  v. lymphatic disease causing lymph edema, or other skin conditions (e.g. eczema, tattoos, striae, keloids, hypertrophic scars, or piercings) in the areas;
  vi. abdominal asymmetry due to musculoskeletal abnormalities, prior surgery, hernias or abdominal organomegaly;
  vii. history of any DSM-IV psychiatric disorder related to body image (such anorexia nervosa, bulimia, body dysmorphic disorder, etc.);
  viii. any clinically-significant abnormal laboratory result during Screening Day 1, as determined by the investigator.

j. Use of systemic, inhaled or topical corticosteroids, drugs with anticoagulant activity (including chronic use of NSAIDs), immunomodulators, anti-metabolites, β-adrenergic receptor agonists or β-adrenergic receptor blockers, nonpotassium-sparing diuretics (e.g. loop or thiazide diuretics), or potent CYP 3A4 inhibitor drugs within 28 days prior to day 1, or during the study;

k. Use of tricyclic antidepressants or monoamine oxidase inhibitor medications within 14 days prior to day 1, or during the study;

l. 12) Subjects unlikely or unable to comply with protocol procedures or adhere to the study visit schedule.

Procedures: All injections were performed in an outpatient setting. At each visit, subjects received a total of 22 subcutaneous injections (1 mL) to infiltrate an area of approximately 16×14 $cm^2$. The study subjects had blood collected for PK assessments at day 1, and day 50: on these days subjects remained at the clinic for 12 hours before being discharged. Once the study was completed and unmasked, only the serum samples collected from subjects receiving the higher combination dose were analyzed. Subjects maintained their usual diet and exercise routine during the study: any fat treatment, including but not limited to liposuction, mesotherapy and abdominal massaging was not allowed. Subjects underwent screening procedures at the Screening Visit. This visit occurred within 30 days (day −30 to day 0) prior to study randomization at Day 1. Study procedures were explained to each subject and written, informed consent was obtained prior to initiating any study-related procedures, including screening procedures. Qualified subjects, who meet all Inclusion/Exclusion criteria, with baseline screening laboratory tests results within normal limits as defined per protocol, were scheduled for the Randomization Visit on Day 1. It was required that all Randomization Visits (Day 1) be scheduled to ensure that over the 8 week treatment period, weekly study drug administration for each subject occurs in a regular cycle, with doses of study drug administered on the same day each week (±2 days).

Safety Assessments: The following safety assessments were performed at the designated time points as specified in the protocol: (1) vital signs (systolic and diastolic blood pressure, heart rate, breathing rate and body temperature); (2) clinical assessment of injection site reactions (local tolerability using the Injection Site Reaction Severity Scale); (3) clinical laboratory tests (hematology, serum chemistry, lipid panel including FFAs, and urine dipstick analysis); (4) and adverse events. Safety parameters monitored during this study were compared within each treatment group (i.e., changes from baseline) and between treatment groups.

Efficacy Assessments: Efficacy assessments included: (1) circumferential measurements of the abdominal treatment area; (2) standardized digital images of the treatment area to assess volumetric changes using a validated methodology and software; (3) Changes in the Patient Global Impression of Severity, and the Patient Global Impression of Change questions evaluating the overall treatment using 'Before' and 'After' photographs; (4) Changes in the Clinician Global Impression of Severity, and the Clinician Global Impression of Change questions evaluating the overall treatment using 'Before' and 'After' photographs (5) the Abdominal Appearance Questionnaire, a Patient Reported Outcome assessing change from baseline; and (6) caliper measurements of skin-fold thickness in the abdominal treatment area.

PK Sample Collections: A total of approximately 16 blood samples (5 mL each) were collected per subject during the study.

PK Parameters: AUC 0-t, AUC 0-inf, C max, t max and t 1/2el.

Analytical Methods: All SX and FP plasma samples were analyzed at the completion of the study using validated LC/MS/MS methods.

Study Endpoints: The study endpoints included both safety assessments and evaluations of efficacy. The primary efficacy endpoint was the change from baseline in circumferential abdominal measurements. Secondary endpoints included the change from baseline in 3-D photographic assessments of volumetric changes of the treatment area as assessed by a masked, central reader; skin-fold caliper measurements of the abdomen in the treatment area; and Patient and Clinician Global Impression of Severity questions, and Patient and Clinician Global Impression of Change questions; and the Abdominal Appearance Questionnaire, a patient-reported outcome instrument assessing the treatment response. 'Before' and 'After' digital photographs (lateral and frontal) of the treatment areas taken at Baseline (day 1), at day 57±2 were used by the subjects in completing their Patient Global Impression of Change questions, and were also used by the site PI who completed the Clinician Global Impression of Change questions assessing each subject. A total of approximately 16 blood samples (5 mL each) were collected per subject during the study.

Results: The results of this study show that the subcutaneous salmeterol and fluticasone formulations provide reductions in computer analyzed 3-dimensional abdominal circumference and volume when administered once weekly for 8 weeks. The 0.05 µg SX+1.0 µg FP treatment group (total weekly SX/FP dose of 1.1 µg/22 µg) experienced the greatest reductions in abdominal circumference (−1.23 cm vs. −0.1 cm for Placebo; p=0.048) and abdominal volume (−183 cc vs. +24 cc for Placebo; p=0.023) as assessed by the Canfield Vectra™ 3D system. In this treatment group, 32% of subjects lost >2 cm in abdominal circumference (vs. 5% for Placebo). Consistent with greater lipolytic responsiveness of younger subjects, a subgroup analysis showed that subjects less than 40 years of age had greater abdominal circumference changes (−2.2 cm; p=0.004) and greater volumetric changes (−360 cc; p=0.004) than subjects older than 40. Similarly, a subgroup analysis showed that thinner subjects (skin-fold thickness less than 13.3 mm (study median)) had greater abdominal circumference changes (−1.8 cm; F=0.053) and greater volumetric changes (−309 cc; p=0.005) than subjects with more abdominal fat (skin-fold thickness less than 13.3 mm). Anterior abdominal flattening was observed in 2D images and was recognized as a reduction in grade of severity of the adiposity in treated subjects. No significant change in weight was observed in any treatment group over the 8-week trial. In the non-treatment study extension, reductions in abdominal circumference and volume in the 0.05 µg SX+1.0 µg FP treatment group (total weekly SX/FP dose of 1.1 µg/22 µg) persisted for 12 weeks post-treatment. The dosage formulations were well-tolerated when injected weekly into the abdominal subcutaneous fat of healthy subjects with the most commonly reported adverse events being mild, transient injection site pain and irritation. There was no difference in injection site reactions between the subcutaneous salmeterol and fluticasone formulations and Placebo-treated groups. There was no inflammation, nodularity or skin atrophy on physical examination of the treatment area. There were also no clinically significant changes in blood pressure, heart rate, respiratory rate or temperature measurements. Plasma salmeterol and FP levels produced by the total weekly SX/FP dose of 11 µg/22 µg were ~⅓-⅕ those of 505(b)(2) reference levels produced by an FDA-approved drug.

Example 4

Pharmaceutical Formulations

Subcutaneous Formulation

To prepare a parenteral pharmaceutical composition suitable for subcutaneous administration, a salt of salmeterol, such as salmeterol xinafoate, is dissolved in PEG 400 which is stabilized with polysorbate 80. Water is then added. This solution is stored in a single-use glass vial which is stored frozen and protected from light until dose preparation. Fluticasone propionate is dissolved in PEG 400 which is also stabilized by the addition of polysorbate 80. Water is then added to the solution. This solution is stored in a single-use glass vial which is stored frozen and protected from light until dose preparation. The salmeterol and/or fluticasone propionate solutions are then diluted to a suitable concentration for subcutaneous administration using a diluent made of an aqueous solution of 20% PEG 400, 1% polysorbate 80, and sterile water for injection.

Transcutaneous Formulation

Also provided herein is a transcutaneous formulation for administration to a patient, and methods of treatment provided herein, including for example methods for the reduction of adipose tissue, using the transcutaneous formulations provided herein. In some embodiments, the transcutaneous formulation contains about 0.01 to about 0.1% by weight fluticasone propionate, about 0.5% to about 10% by weight salmeterol xinafoate or formoterol fumarate, about 1% to about 75% propylene glycol or isopropyl alcohol, and optionally other excipients including but not limited to transcutol, propyl gallate, water, and ethanol, wherein the total percent by weight is 100%.

The following transcutaneous formulations were topically administered to human cadaver skin ex vivo: (1) a transcutaneous formulation comprising fluticasone propionate is in an amount of about 0.05% by weight, salmeterol xinafoate is in an amount of about 1% by weight, propylene glycol is in an amount of about 5% by weight, transcutol is in an amount of about 15% by weight, propyl gallate is in an amount of about 0.025% by weight, water is in an amount of about 15% by weight, and ethanol is in an amount of about 64% by weight; and (2) a transcutaneous formulation comprising about 0.05% by weight fluticasone propionate, 1% by weight formoterol fumarate, propylene glycol in an amount of about 50% by weight, and isopropyl alcohol in an amount of about 48.95% by weight.

The examples and embodiments described herein are for illustrative purposes only and various modifications or changes are included within the spirit and purview of this application and scope of the appended claims. All publications, patents, and patent applications cited herein are hereby incorporated by reference for all purposes.

What is claimed is:

1. A method of reducing adipose tissue in a patient in need thereof comprising subcutaneously administering to said patient a non-sustained release pharmaceutical formulation that is suitable for subcutaneous injection, the formulation comprising:
   (a) an adipose tissue-reducing lipophilic long-acting selective beta-2 adrenergic receptor agonist or a salt thereof; and
   (b) at least one subcutaneously acceptable inactive ingredient;
   wherein the formulation is administered at a dose of less than about 5 μg per week.

2. The method of claim 1 wherein said method is effective to provide cosmetic fat reduction in the patient.

3. The method of claim 1 wherein said method is effective to provide therapeutic fat reduction in the patient.

4. The method of claim 1 wherein the lipophilic long-acting selective beta-2 adrenergic receptor agonist is administered to the patient in a total weekly dose that is between about 5 ng to about 5 μg.

5. The method of claim 1 wherein the lipophilic long-acting selective beta-2 adrenergic receptor agonist is salmeterol, formoterol, or a salt or a combination thereof.

6. The method of claim 1 wherein the circumference of the patient's abdomen is reduced by at least one centimeter when assessed by tape measure.

7. The method of claim 6 wherein the one centimeter reduction in the patient's waist is evident at anytime within 8 weeks from the first day of treatment.

8. A pharmaceutical formulation suitable for subcutaneous injection comprising:
   (a) an adipose tissue-reducing lipophilic long-acting selective beta-2 adrenergic receptor agonist or a salt thereof; and
   (b) at least one subcutaneously acceptable inactive ingredient;
   wherein the formulation is formulated to be administered into a layer of subcutaneous fat in a human in need at a weekly dose of less than about 5 μg of the beta-2 adrenergic receptor agonist or salt thereof.

9. The formulation of claim 8 wherein the lipophilic long-acting selective beta-2 adrenergic receptor agonist is salmeterol, formoterol, or a salt or combination thereof.

10. The formulation of claim 9 wherein the lipophilic long-acting selective beta-2 adrenergic receptor agonist is salmeterol xinafoate.

11. The formulation of claim 10 that is formulated to provide a session dose of salmeterol xinafoate in an amount that is about 5 ng to about 5 μg.

12. The formulation of claim 8 wherein the formulation further comprises a glucocorticosteroid or a salt thereof.

13. The formulation of claim 12 wherein the glucocorticosteroid is dexamethasone, prednisolone, or a salt or a combination thereof.

14. The formulation of claim 13 wherein the glucocorticosteroid is in an amount of less than about 1,000 μm.

15. The formulation of claim 12 wherein the glucocorticosteroid is fluticasone, budesonide, or a salt or a combination thereof.

16. The formulation of claim 15 wherein the glucocorticosteroid is in an amount of less than about 25 μg.

17. The formulation of claim 16 wherein the glucocorticosteroid is fluticasone or a salt thereof.

18. The formulation of claim 8 wherein the lipophilic long-acting selective beta-2 adrenergic receptor agonist selectively partitions into adipose tissue relative to blood plasma when administered subcutaneously to a patient, and wherein said partition has a ratio of between about 0.01 to about 0.2.

19. The method of claim 5 wherein the lipophilic long-acting selective beta-2 adrenergic receptor agonist is salmeterol or a salt thereof.

20. The method of claim 5 wherein the lipophilic long-acting selective beta-2 adrenergic receptor agonist is salmeterol xinafoate.

21. The method of claim 5 wherein the lipophilic long-acting selective beta-2 adrenergic receptor agonist is formoterol or a salt thereof.

22. The method of claim 5 wherein the lipophilic long-acting selective beta-2 adrenergic receptor agonist is formoterol fumarate.

* * * * *

(12) EX PARTE REEXAMINATION CERTIFICATE (10690th)
United States Patent
Dobak et al.

(10) Number: US 8,404,750 C1
(45) Certificate Issued: *Aug. 19, 2015

(54) METHODS FOR ADMINISTRATION AND FORMULATIONS FOR THE TREATMENT OF REGIONAL ADIPOSE TISSUE

(75) Inventors: John Daniel Dobak, La Jolla, CA (US); Kenneth Walter Locke, Carlsbad, CA (US)

(73) Assignee: NEOTHETICS, INC., San Diego, CA (US)

Reexamination Request:
No. 90/013,348, Sep. 19, 2014

Reexamination Certificate for:
Patent No.: 8,404,750
Issued: Mar. 26, 2013
Appl. No.: 13/284,741
Filed: Oct. 28, 2011

( * ) Notice: This patent is subject to a terminal disclaimer.

Related U.S. Application Data

(63) Continuation of application No. 12/788,190, filed on May 26, 2010.

(60) Provisional application No. 61/181,627, filed on May 27, 2009, provisional application No. 61/251,624, filed on Oct. 14, 2009, provisional application No. 61/289,972, filed on Dec. 23, 2009.

(51) Int. Cl.
*A61K 31/137* (2006.01)
*A61K 31/167* (2006.01)
*A61K 31/56* (2006.01)
*A61K 9/00* (2006.01)
*A61K 31/573* (2006.01)
*A61K 31/58* (2006.01)

(52) U.S. Cl.
CPC .............. *A61K 9/0019* (2013.01); *A61K 31/137* (2013.01); *A61K 31/167* (2013.01); *A61K 31/56* (2013.01); *A61K 31/573* (2013.01); *A61K 31/58* (2013.01); *A61K 2300/00* (2013.01)

(58) Field of Classification Search
None
See application file for complete search history.

(56) References Cited

To view the complete listing of prior art documents cited during the proceeding for Reexamination Control Number 90/013,348, please refer to the USPTO's public Patent Application Information Retrieval (PAIR) system under the Display References tab.

*Primary Examiner* — Johnny F Railey

(57) ABSTRACT

Provided herein are pharmaceutical formulations, methods, and systems for treating regional fat deposits and fat-related conditions and indications. Methods comprise administering a pharmaceutical formulation consisting essentially of a long-acting beta-2 adrenergic receptor agonist, for example, salmeterol, suitable for subcutaneous administration. Methods further comprise administering a pharmaceutical formulation that is suitable for subcutaneous injection comprising: (a) a lipophilic long-acting selective beta-2 adrenergic receptor agonist and/or glucocorticosteroid, or a salt, optical isomer, racemate, solvate, or polymorph thereof; and (b) at least one subcutaneously acceptable inactive ingredient.

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-22 is confirmed.

\* \* \* \* \*